(12) United States Patent
Nir et al.

(10) Patent No.: US 11,116,383 B2
(45) Date of Patent: Sep. 14, 2021

(54) ARTICULATED STRUCTURED LIGHT BASED-LAPAROSCOPE

(71) Applicant: Asensus Surgical Europe S.à.R.L., Lugano (CH)

(72) Inventors: Tal Nir, Haifa (IL); Motti Frimer, Zichron Yaakov (IL); Gal Atarot, Kfar Saba (IL)

(73) Assignee: Asensus Surgical Europe S.à.R.L., Lugano (CH)

( * ) Notice: Subject to any disclaimer, the term of this patent is extended or adjusted under 35 U.S.C. 154(b) by 501 days.

(21) Appl. No.: 15/129,925

(22) PCT Filed: Mar. 31, 2015

(86) PCT No.: PCT/IL2015/050349
§ 371 (c)(1),
(2) Date: Sep. 28, 2016

(87) PCT Pub. No.: WO2015/151098
PCT Pub. Date: Oct. 8, 2015

(65) Prior Publication Data
US 2017/0172382 A1    Jun. 22, 2017

Related U.S. Application Data

(60) Provisional application No. 62/130,641, filed on Mar. 10, 2015, provisional application No. 61/973,899, filed on Apr. 2, 2014.

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00006* (2013.01); *A61B 1/008* (2013.01);
(Continued)

(58) Field of Classification Search
CPC ............ A61B 1/00009; A61B 1/00006; A61B 1/00045; A61B 1/008; A61B 1/042;
(Continued)

(56) References Cited

U.S. PATENT DOCUMENTS 6,019,724 A * 2/2000 Gronningsaeter ... A61B 8/0833
600/439
6,387,044 B1 5/2002 Tachibana et al.
(Continued)

FOREIGN PATENT DOCUMENTS

CN        203042209 U    7/2013
JP        6063003 A      3/1994
(Continued)

OTHER PUBLICATIONS

International Search Report of PCT/IL2015/050349, dated Nov. 4, 2015.
(Continued)

*Primary Examiner* — Timothy J Neal
*Assistant Examiner* — William B Chou

(57) ABSTRACT

The present invention provides a structured-light based system for providing a 3D image of at least one object within a field of view within a body cavity, comprising: a. An endoscope; b. at least one camera located in the endoscope's proximal end, configured to real-time provide at least one 2D image of at least a portion of said field of view by means of said at least one lens; c. a light source, configured to real-time illuminate at least a portion of said at least one object within at least a portion of said field of view with at least one time and space varying predetermined light pattern; and, d. a sensor configured to detect light reflected from said field of view; e. a computer program which, when executed by data processing apparatus, is configured to generate a 3D image of said field of view.

45 Claims, 43 Drawing Sheets

(51) Int. Cl.
  *A61B 1/06* (2006.01)
  *A61B 34/20* (2016.01)
  *G06T 7/33* (2017.01)
  *A61B 1/008* (2006.01)
  *A61B 1/313* (2006.01)
  *A61B 18/22* (2006.01)
  *G06T 15/20* (2011.01)
  *A61B 90/00* (2016.01)
  *A61B 34/00* (2016.01)
  *A61B 34/30* (2016.01)

(52) U.S. Cl.
  CPC .......... *A61B 1/00045* (2013.01); *A61B 1/042* (2013.01); *A61B 1/0676* (2013.01); *A61B 1/313* (2013.01); *A61B 1/3132* (2013.01); *A61B 18/22* (2013.01); *A61B 34/20* (2016.02); *G06T 7/337* (2017.01); *G06T 15/205* (2013.01); *A61B 1/00* (2013.01); *A61B 2034/2048* (2016.02); *A61B 2034/2065* (2016.02); *A61B 2034/301* (2016.02); *A61B 2034/742* (2016.02); *A61B 2090/367* (2016.02); *A61B 2090/373* (2016.02); *G06T 2207/10021* (2013.01); *G06T 2207/10081* (2013.01); *G06T 2207/10104* (2013.01); *G06T 2207/10136* (2013.01)

(58) Field of Classification Search
  CPC ..... A61B 1/0676; A61B 1/313; A61B 1/3132; A61B 34/20; A61B 18/22; G06T 7/337; G06T 15/205
  USPC ........................................................ 600/111
  See application file for complete search history.

(56) References Cited

U.S. PATENT DOCUMENTS

| | | | |
|---|---|---|---|
| 6,503,195 | B1 | 1/2003 | Keller et al. |
| 8,911,358 | B2 | 12/2014 | Koninckx et al. |
| 9,659,345 | B2 | 5/2017 | Razzaque et al. |
| 2002/0097332 | A1 | 7/2002 | Martin et al. |
| 2002/0167422 | A1 | 11/2002 | Andre et al. |
| 2004/0106916 | A1* | 6/2004 | Quaid .................... G06F 3/0346 606/1 |
| 2005/0123189 | A1 | 6/2005 | Bayer et al. |
| 2007/0173861 | A1* | 7/2007 | Strommer ................ A61B 6/12 606/108 |
| 2007/0197896 | A1* | 8/2007 | Moll .................... A61B 1/00039 600/407 |
| 2008/0287805 | A1* | 11/2008 | Li .......................... A61B 8/0833 600/471 |
| 2009/0018465 | A1* | 1/2009 | Hessel .................... A61B 5/064 600/559 |
| 2009/0177032 | A1 | 7/2009 | Garibaldi et al. |
| 2009/0182224 | A1* | 7/2009 | Shmarak .............. A61B 5/7275 600/424 |
| 2011/0057930 | A1 | 3/2011 | Keller et al. |
| 2011/0069160 | A1 | 3/2011 | Ning |
| 2012/0190923 | A1 | 7/2012 | Kunz et al. |
| 2013/0060146 | A1* | 3/2013 | Yang ....................... A61B 5/055 600/476 |
| 2014/0052005 | A1 | 2/2014 | Yokota |
| 2014/0336461 | A1 | 11/2014 | Reiter et al. |
| 2015/0238276 | A1* | 8/2015 | Atarot ................ A61B 1/00009 600/424 |
| 2016/0302747 | A1* | 10/2016 | Averbuch ............... A61B 6/547 |
| 2017/0188011 | A1* | 6/2017 | Panescu ............. A61B 1/00009 |

FOREIGN PATENT DOCUMENTS

| | | |
|---|---|---|
| KR | 1020090123260 B1 | 12/2009 |
| WO | 2010081094 A2 | 7/2010 |
| WO | 2013/128457 A1 | 9/2013 |
| WO | 2015/151098 A2 | 10/2015 |

OTHER PUBLICATIONS

Written Opinion of the International Search Authority of PCT/IL2015/050349, dated Nov. 4, 2015.
Christoph Schmalz et al., "An endoscopic 3D scanner based on structured light" Medical Image Analysis, vol. 16, pp. 1063-1072 (2012).
Jason Geng "Structured-light 3D surface imaging: a tutorial" Advances in Optics and Photonics, vol. 3, pp. 128-160 (2011).

* cited by examiner

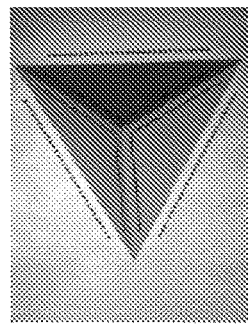 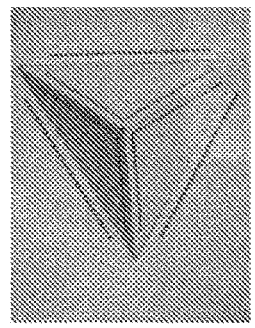 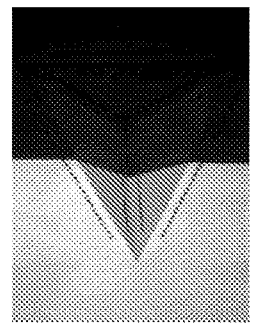 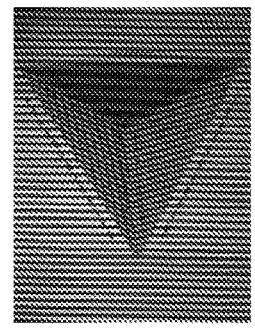
Fig. 6A    Fig. 6B    Fig. 6C    Fig. 6D
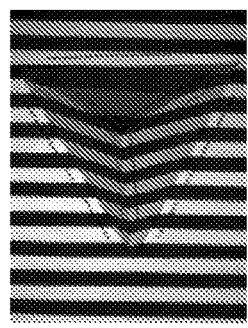 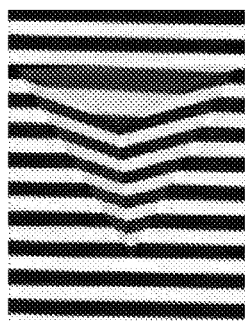 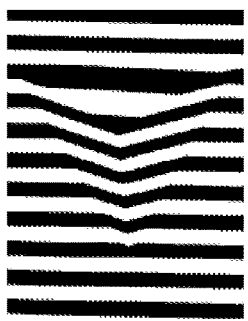 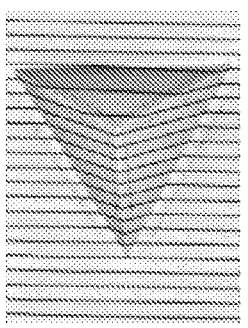
Fig. 7A    Fig. 7B    Fig. 7C    Fig. 7D
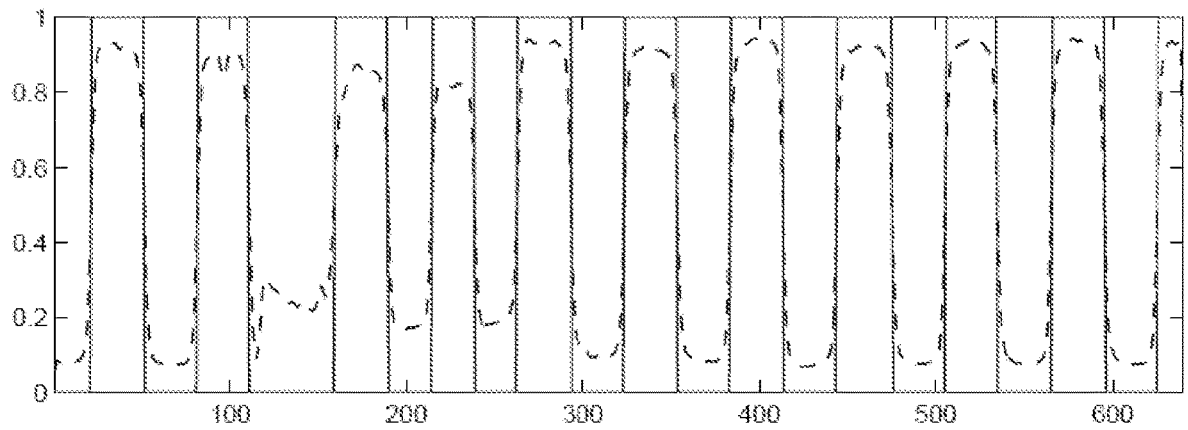
Fig. 7E

A

B

C

D

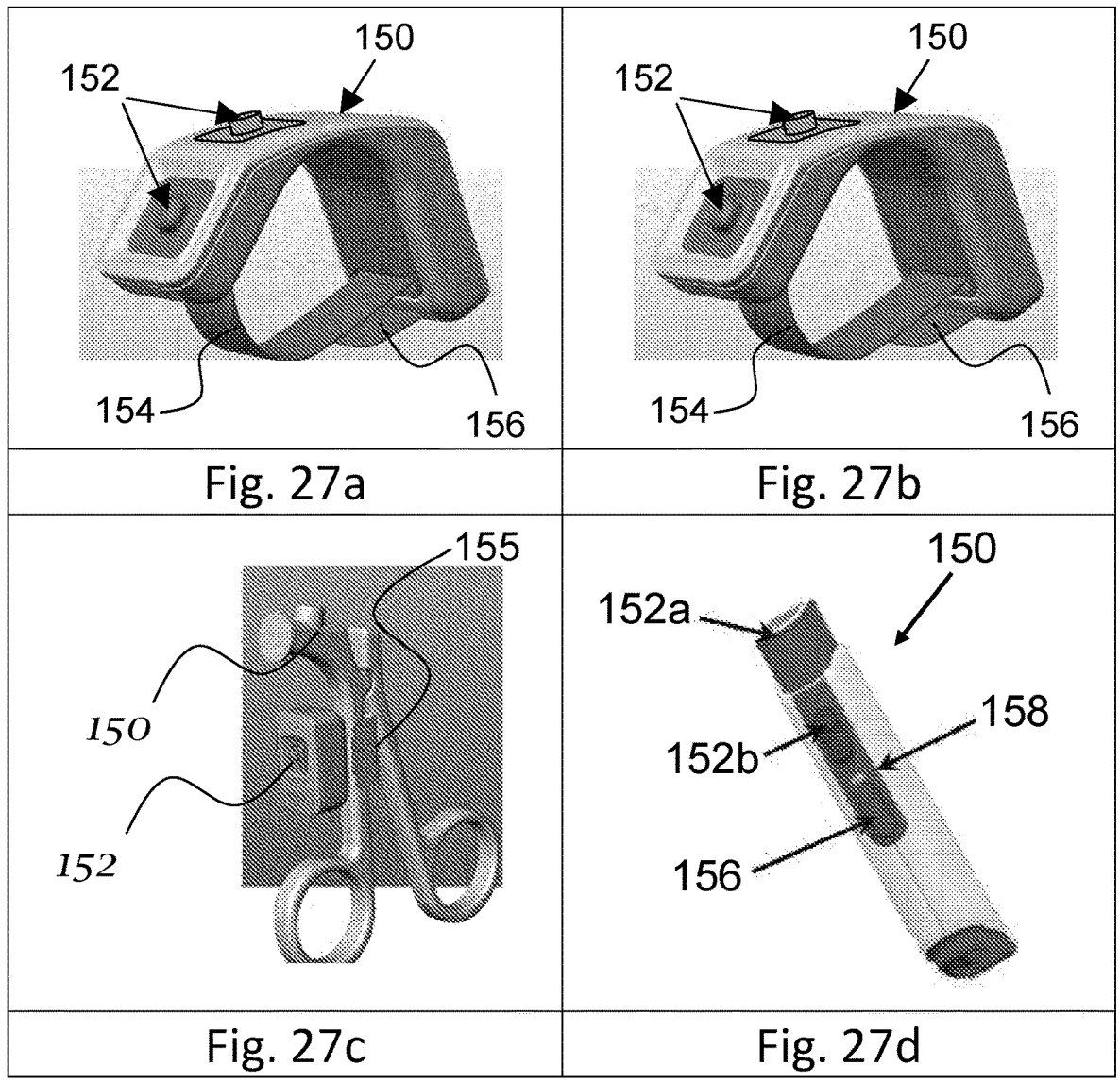

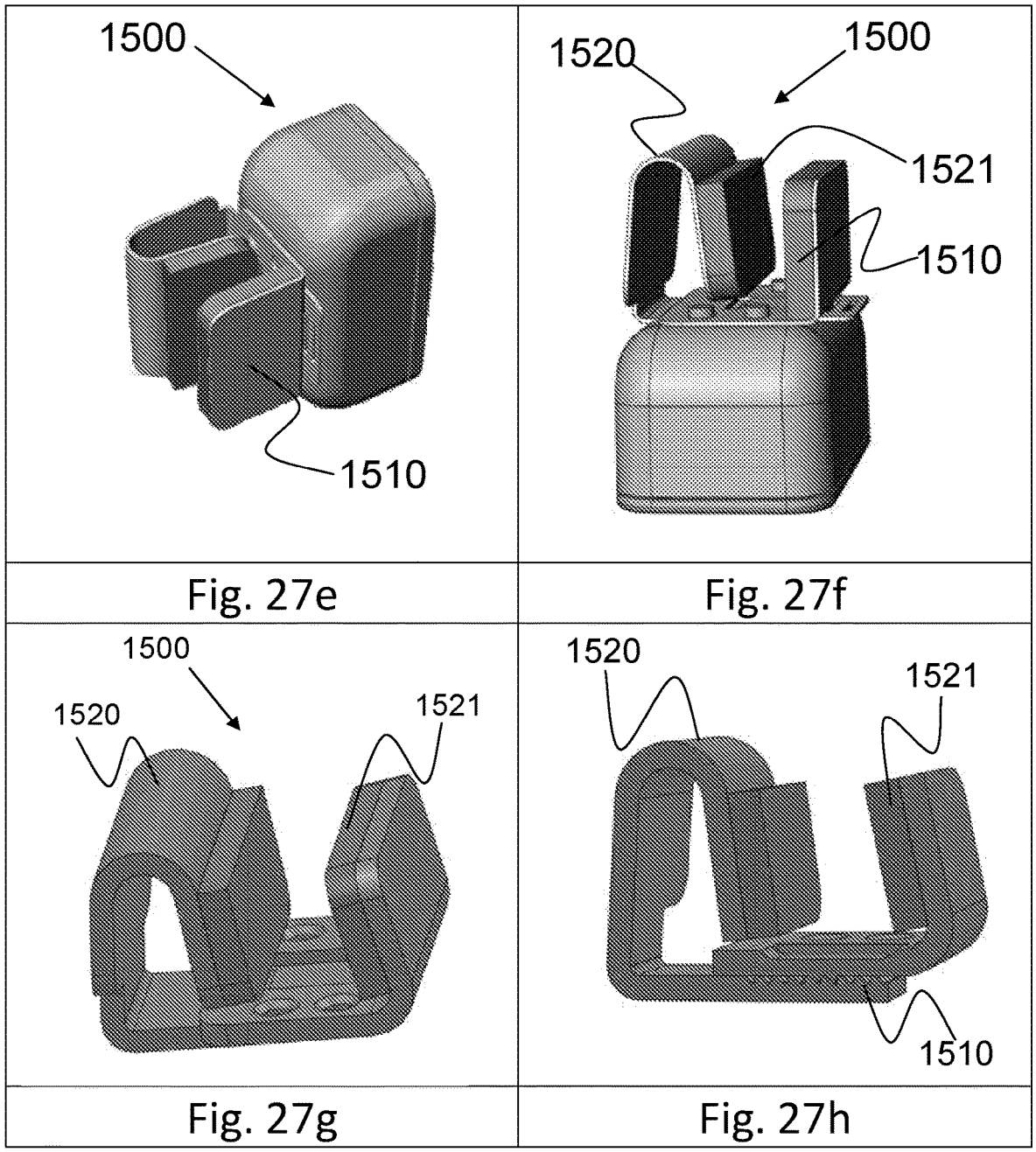

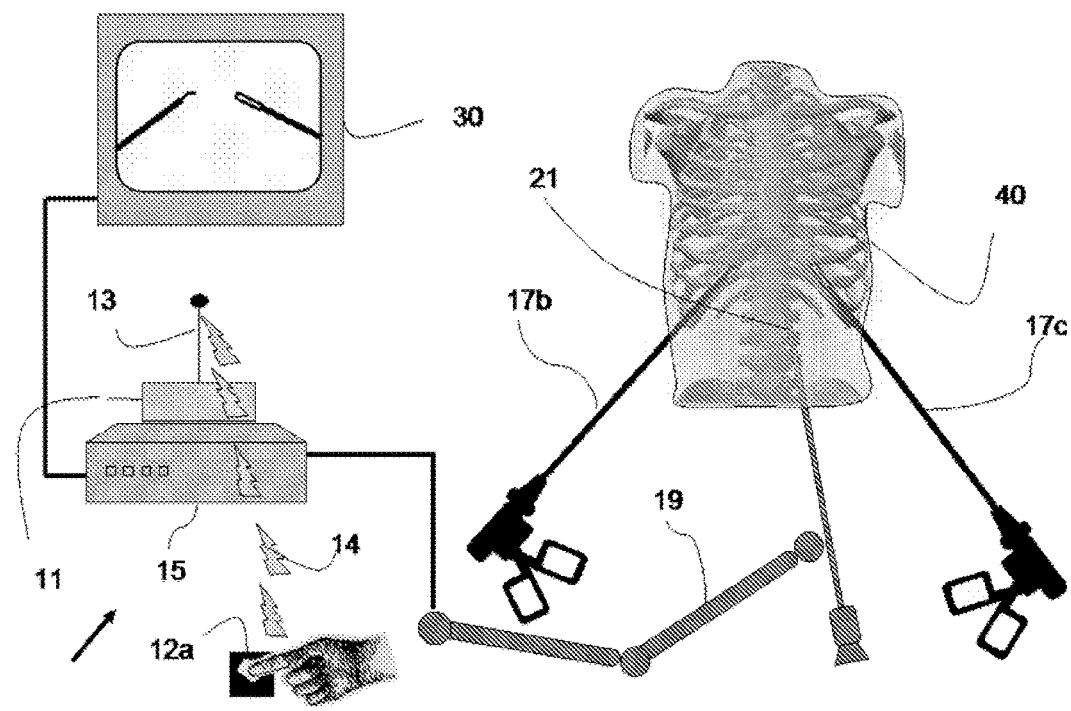
Fig. 28
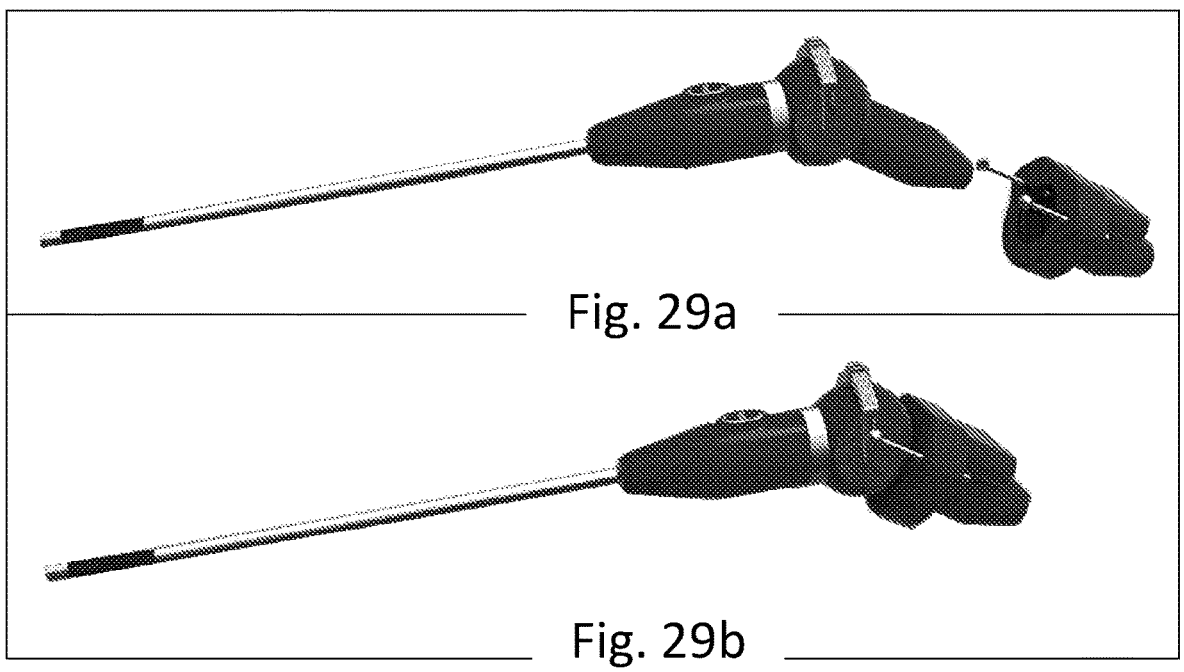
Fig. 29a
Fig. 29b

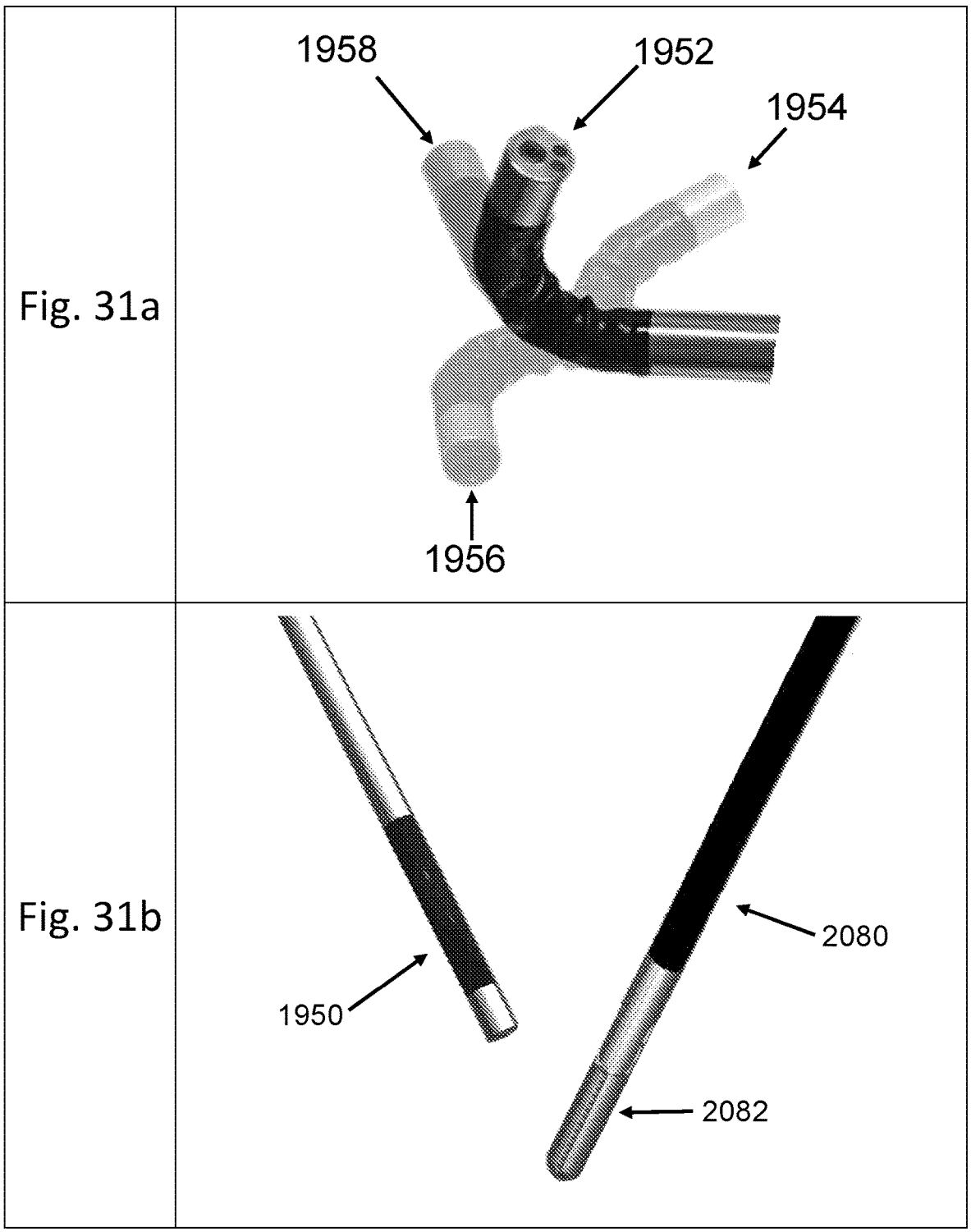

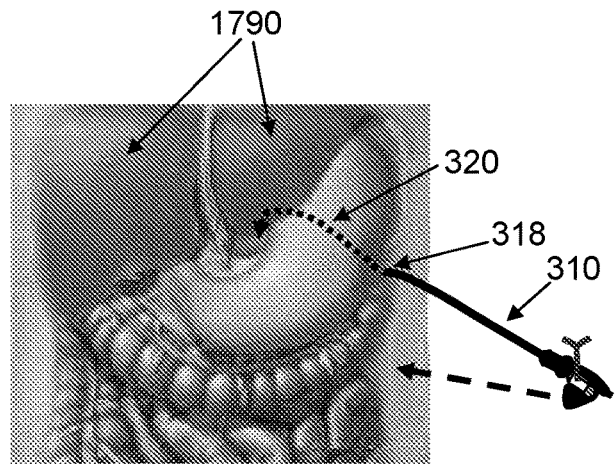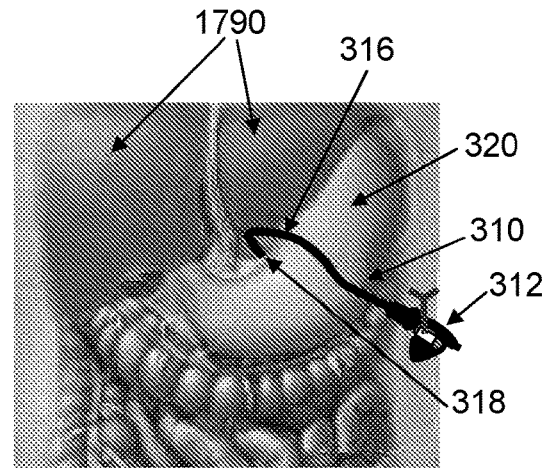
Fig. 46A  Fig. 46B
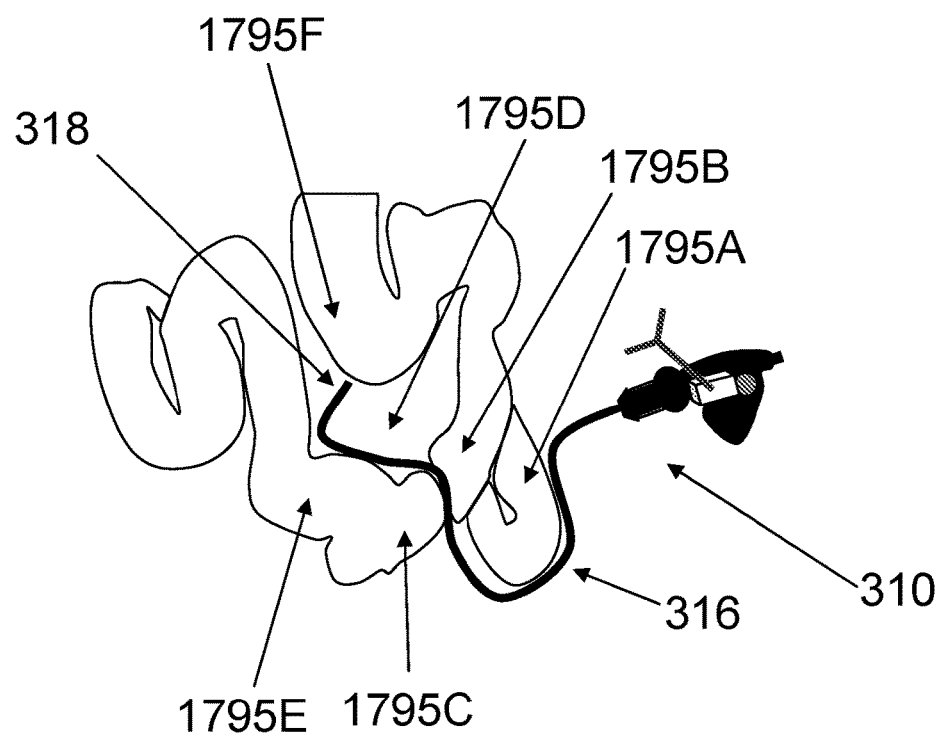
Fig. 47

ARTICULATED STRUCTURED LIGHT BASED-LAPAROSCOPE

FIELD OF THE INVENTION

The present invention generally pertains to a system and method for providing a 3D laparoscopic image.

BACKGROUND OF THE INVENTION

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and is not available in all hospitals. During laparoscopic surgery it is often required to shift the spatial placement of the endoscope in order to present the surgeon with the optimal view. Conventional laparoscopic surgery makes use of either human assistants that manually shift the instrumentation or alternatively robotic automated assistants (such as JP patent No. 06063003).

In laparoscopic surgery, the surgeon performs the operation through small holes using long instruments and observing the internal anatomy with an endoscope camera. The surgeon's performance is largely dependent on the camera position relative to the instruments and on a stable image shown at the monitor. In general, the surgeon needs a close-up view of the area in which he wants to work, however, there are times when an overview of a large portion of the working area, such as an overall view of the interior of the abdomen, is desirable.

In addition, conventional laparoscopes provide the surgeon with a 2D image of the field of view.

U.S. Pat. No. 6,387,044 discloses a laparoscope apparatus for use in laparoscopic surgery or the like comprises a cannula with an inner hollow having therein a light guide for introducing light to its tip end for illuminating the object to be observed, and an endoscope which is capable of being pulled into and out from the inner hollow of the cannula. The cannula is airtightly sealed with a transparent member at its tip end, while the endoscope has therein an image pick-up with a wide-angle lens, and the image pick-up is housed in the cannula close to the transparent member.

However, U.S. Pat. No. 6,387,044 does not disclose providing a 3D image.

Korean Patent Application KR2009/012326 discloses a laparoscope and an image processing system using the same to efficiently perform a laparoscope operation by outputting an image of the inside of the abdominal cavity. The laparoscope includes a wide angle lens, an optical fiber, an inserting part, and an optical interface part. The wide angle lens is arranged at one end of the laparoscope, and is a fisheye lens. The focal distance of the wide angle lens is controllable. The optical fiber delivers incident light from the wide angle lens to the camera part, and is received in an inner space of the inserting part. The inserting part is inserted inside the abdominal cavity. The optical interface part delivers the light delivered from the optical fiber to the camera part. The camera part is a two dimensional camera or a three dimensional camera.

However, Korean Patent Application KR2009/012326 requires a 3D camera in order to provide a 3D image.

U.S. Patent Application US2011069160 discloses an imaging system and method of application, including lens designs tailored to be used with particular transformation algorithms, electronic hardware and algorithms for image transformations is described. Exemplary application of the system including automotive, photographic and medical endoscopic are also described. The system enables improved image view and allows customization of views by the end user even after installation of the image system hardware. In U.S. Patent Application US2011069160, mathematical algorithms are used to alter the image, so that a continuously varying distortion of the image is possible, so that desired portions of the image are magnified, but the whole of the image remains within the field of view.

However, US Patent Application US2011069160 does not disclose providing a 3D image.

Chinese Utility Model CN203042209 discloses a laparoscopic puncture device with an intra-cavity full-view auxiliary lens, which relates to a surgical instrument device, in particular to the laparoscopic puncture device with the intra-cavity full-view auxiliary lens for abdominal cavity minimally-invasive surgery. A main lens of a laparoscope enters into the abdominal cavity through a cannular puncture device, the puncture device is provided with an auxiliary lens which can be used for observing intra-cavity full view, and the auxiliary lens is a wide-angle lens and cold light source combination body; the auxiliary lens is arranged at the middle part of the puncture device entering into the abdominal cavity, and the auxiliary lens is positioned at the highest position of the abdominal cavity after the abdominal cavity is subjected to air inflation; the outer ring of the puncture device is provided with a groove, the wide-angle lens and cold light source combination body of the auxiliary lens is embedded in the groove and is combined into a whole with the puncture device; and the wide angle of a wide-angle lens of the auxiliary lens is larger than or equal to 270 degrees, and the resolution ratio of the wide-angle lens of the auxiliary lens is 1-3 million pixels. By adding a cold light source and the wide-angle lens, the full-view visible function is added on the basis of the original function of the puncture device, 80 percent of the abdominal cavity can be within a visible range, motion of all instruments is within the visible range, the surgical blind area of a surgeon can be removed, and the surgery can be safer.

However, US Patent Application US2011069160 does not disclose providing a 3D image.

U.S. Patent Application US2002/0097332 discloses a system for achieving perspective-corrected views at a location removed from the site of the creation of a distorted wide angle image without the transmission of control signals to the site of image creation. angles of tilt, pan and rotation, as well as degrees of magnification, are achieved without the use of mechanical devices by using transform algorithms. The system provides for the transmission of signals related to an uncorrected image from a site where this distorted image is created, with the transmitted signals being received at one or more processing sites for creating the perspectively-corrected views. Transmission can be via telephone lines, with the system including signal compression and decompression units. wireless transmission is also utilized where desired.

However, US Patent Application US2002/0097332 does not disclose providing a 3D image.

It is therefore a long felt need to provide an enhanced 3D laparoscopic image using an articulated endoscope.

SUMMARY OF THE INVENTION

It is an object of the present invention to disclose a system for providing an enhanced 3D laparoscopic image using an articulated endoscope.

It is another object of the present invention to disclose a structured-light based endoscope for providing a 3D image of at least one object within a field of view within a body cavity, comprising:

a. at least one endoscope having at least one lens in the endoscope's distal end;

b. at least one camera located in the endoscope's proximal end, configured to real-time provide at least one 2D image of at least a portion of said field of view by means of said at least one lens;

c. at least one light source, configured to real-time illuminate at least a portion of said at least one object within at least a portion of said field of view with at least one time and space varying predetermined light pattern;

d. at least one sensor configured to detect light reflected from said field of view; and, e. a computer program which, when executed by data processing apparatus, is configured to generate a 3D image of said field of view;

f. wherein said predetermined light pattern is a structured light pattern; wherein said 3D image is constructable from said detected light reflected from said field of view and said structured light pattern.

It is another object of the present invention to disclose the system as described above, additionally comprising at least one maneuvering system, configured to maneuver said endoscope in at least two degrees of freedom (DOF).

It is another object of the present invention to disclose the system as described above, wherein said endoscope is an articulating endoscope.

It is another object of the present invention to disclose the system, wherein said construction of said 3D image is by means of calculating the world coordinates of at least one point on said at least one object.

It is another object of the present invention to disclose the system, wherein said world coordinates of at least one point on said at least one object can be calculated from the following equation:

$$\tilde{\alpha} = \frac{n^T \tilde{x}_p}{n^T R_p v_c},$$

where $n^T$ is the transpose of the normal to the plane defined by the stripe id $x_p$, $\tilde{x}_p = x_p[\delta x_p, 0, f_p]^T$ is the perturbed stripe id $x_p$, $R_p$ is the rotation matrix defining the transformation between the world coordinate system and the projector coordinate system and $v_c$ is the direction of the ray between the stripe id and the object point.

It is another object of the present invention to disclose the system, wherein, for any point $X_w$ in world coordinate system, the coordinate $X_c$ of the same point in the camera coordinate system is calculated according to the following equation:

$$X_c = C_c X_w,$$

where $C_c$, the camera perspective projection matrix, is of the form $$C_c = \alpha \begin{bmatrix} f_x & kf_y & x^0 \\ 0 & f_y & y_c^0 \\ 0 & 0 & 1 \end{bmatrix} [R_c \ t_c].$$

where $\alpha$ is a proportion coefficient, $f_x$ and $f_y$ are the camera focal length scaled to each of the camera image dimensions, k is the shear of the camera coordinate system, $x_c^0$ and $y_c^0$ are the origin of $X_c$ in image coordinates, and $R_c$ and $t_c$ define the transformation between the world coordinate system and the light source's coordinate system, with $R_c$ being a rotation matrix and $t_c$ a translation matrix.

It is another object of the present invention to disclose the system, wherein $x_p^0$ is the x-coordinate of the intersection of the optical axis and the projector.

It is another object of the present invention to disclose the system, wherein, for any point $X_w$ in world coordinate system, the coordinate $X_p$ of the same point in the light source coordinate system is calculated according to the following equation:

$$X_p = C_p X_w,$$

where $C_p$, the light source perspective projection matrix, is of the form $$C_p = \alpha \begin{bmatrix} f_p & 0 & x_p^0 \\ 0 & 0 & 1 \end{bmatrix} [R_p \ t_p]$$

where $\alpha$ is a proportion coefficient, $f_p$ is the light source focal length scaled to projector dimensions, $x_p^0$ is the origin of $X_p$ in projector coordinates, and $R_p$ and $t_p$ define the transformation between the world coordinate system and the light source's coordinate system, with $R_p$ being a rotation matrix and $t_p$ a translation matrix.

It is another object of the present invention to disclose the system, wherein the world coordinates $p_w$ of a point P is calculated according to the following equation:

$$\begin{pmatrix} p_p \\ p_s \end{pmatrix} - \begin{pmatrix} F_c(p_w; \Theta_c) \\ F_p(p_w; \Theta_p) \end{pmatrix} = 0$$

where $p_p = (x_p, y_p)^t$ is the pixel coordinate of said point, $p_s = (x_s)$ is the stripe value of said point P, $F_c(P_w; \Theta_c) = P_p - \in_p$ is the noise-free value of the vector of pixel coordinates, where $P_p$ is the vector of measured pixel coordinates and $\in_p$ is the vector of errors in the pixel coordinates; $F_p(P_w; \Theta_p) = P_s - \in_s$ is the noise-free value of the vector of stripe coordinates, where $P_s$ is the vector of measured stripe coordinates and $\in_s$ is the vector of errors in the stripe coordinates.

It is another object of the present invention to disclose the system, wherein the world coordinates $p_w$ of a point P is estimated according to the following non-linear least squares (NLLS) equations:

$$\min_{\Theta_c} \|P_p - F_c(P_w; \Theta_c)\|^2$$

$$\min_{\Theta_p} \|P_s - F_p(P_w; \Theta_p)\|^2$$

It is another object of the present invention to disclose the system, wherein said NLLS equations are solvable by means of a NLLS solving algorithm selected from a group consisting of the Gauss-Newton technique, the quasi-Newton technique, and the Levenberg-Marquardt technique.

It is another object of the present invention to disclose the system, wherein the location, in world coordinates, of a kth point on the object is calculated according to the following equation:

$$p_w^k = \frac{C_{1,2,1}^k - x_p C_{3,2,1}^k - y_p C_{1,3,1}^k - x_s C_{1,2,2}^k + x_s x_p C_{3,2,2}^k + x_s y_p C_{1,3,2}^k}{C_{1,2,1}^4 - x_p C_{3,2,1}^4 - y_p C_{1,3,1}^4 - x_s C_{1,2,2}^4 + x_s x_p C_{3,2,2}^4 + x_s y_p C_{1,3,2}^4}$$

where $C_{i,j,l}^k = \det(C_c^i, C_c^j, C_c^l, e_k)$ are constants which depend only on a camera perspective transformation matrix and a projector perspective transformation matrix.

It is another object of the present invention to disclose the system, additionally comprising a calibration object.

It is another object of the present invention to disclose the system, wherein said calibration object is of predetermined shape and size.

It is another object of the present invention to disclose the system, wherein said calibration object comprises fiducial locations of predetermined position.

It is another object of the present invention to disclose the system, wherein said lens is a wide-angle lens.

It is another object of the present invention to disclose the system, wherein said wide-angle lens is selected from a group consisting of a fisheye lens, an omnidirectional lens and any combination thereof.

It is another object of the present invention to disclose the system, wherein said structured light uses at least one of a group consisting of: temporal sequencing, spatial sequencing, wavelength sequencing and any combination thereof.

It is another object of the present invention to disclose the system, wherein cancerous tissue can be differentiated from normal tissue by means of said wavelength sequencing.

It is another object of the present invention to disclose the system, wherein the relationship between the location of a point in said camera image, the location of a point in a light source and the location of a point in space is known for all said points in said camera image, said points in said light source and said points in space.

It is another object of the present invention to disclose the system, wherein said known relationships are used to generate said 3D image from said 2D camera image.

It is another object of the present invention to disclose the system, wherein said system comprises at least one location estimating means configured to real-time locate the 3D spatial position at any given time t of a member of a group consisting of: said endoscope, a surgical tool and any combination thereof.

It is another object of the present invention to disclose the system, wherein said at least one location estimating means comprises (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element.

It is another object of the present invention to disclose the system, wherein said at least one location estimating means is an interface subsystem between a surgeon and said at least one surgical tool, the interface subsystem comprising:
a. at least one array comprising N regular or patterned light sources, where N is a positive integer;
b. at least one array comprising M cameras, each of the M cameras, where M is a positive integer;
c. optional optical markers and means for attaching the optical marker to the at least one surgical tool; and;
d. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to disclose the system, wherein display of said 3D image is by means of a member of a group consisting of: a 3D screen, 3D glasses, autostereoscopy, holography, a volumetric display, integral imaging, wiggle stereoscopy, an active shutter 3d system, a polarized 3d system, an interference filter system, a color anaglyph systems a Chromadepth system, an over/under format, and any combination thereof.

It is another object of the present invention to disclose the system, wherein said tools are detectable by means of depth cues in said 3D image.

It is another object of the present invention to disclose the system, wherein at least one structure selected from a group consisting of an organ, a blood vessel, a nerve, a limb and any combination thereof is detectable by said system.

It is another object of the present invention to disclose the system, wherein at least one said structure are emphasizable by a member of a group consisting of: virtual reality overlays, color markings, pattern markings, outlines, arrows, and any combination thereof.

It is another object of the present invention to disclose the system, wherein data from at least one other imaging modality is storable in a database.

It is another object of the present invention to disclose the system, wherein said data from said at least one other imaging modality is matchable to and alignable with said 3D image, such that substantially all information from said at least one other imaging modality and said 3D image is viewable as a single 3D image.

It is another object of the present invention to disclose the system, wherein said at least one other imaging modality is selected from a group consisting of: CT, MRI, ultrasound and PET and any combination thereof.

It is another object of the present invention to disclose the system, wherein additional information displayable by said system is selected from a group consisting of:
recommendations useful in directing the progress of an operation, information useful in assisting an operator in making a decision, information useful for a record of the operation and any combination thereof.

It is another object of the present invention to disclose the system, wherein said information is displayable visually or audibly.

It is another object of the present invention to disclose the system, wherein said information is selected from a group consisting of: camera pose, body temperature, time, elapsed time since start of operation, patient notes, notes made during the It is another object of the present invention to disclose the system, additionally comprising at least one joystick unit in communication with said maneuvering system, configured to operate said maneuvering system.

It is another object of the present invention to disclose the system, wherein operation of said joystick results in movement of said endoscope by means of said maneuvering system.

It is another object of the present invention to disclose the system, wherein said joystick unit is wearable by a user of said system.

It is another object of the present invention to disclose the system, wherein said joystick unit is coupled to at least one surgical tool used in said medical procedure.

It is another object of the present invention to disclose the system, wherein said at least one surgical tool is said endoscope.

It is another object of the present invention to disclose the system, wherein said movement of said joystick is proportional to said movement of said endoscope.

It is another object of the present invention to disclose the system, wherein, if said joystick unit's speed of motion is above a predetermined value, said endoscope's speed is at a predetermined value.

It is another object of the present invention to disclose the system, wherein said joystick unit is a force joystick.

It is another object of the present invention to disclose the system, wherein said joystick unit comprises a base and lever coupled to said base, such that movement of said lever results in movement of said endoscope; further wherein said movement of said lever is proportional to said movement of said endoscope.

It is another object of the present invention to disclose the system, wherein said joystick unit comprises a base and a button jointly connected to said base, such that movement of said button results in movement of said endoscope; further wherein said movement of said button is proportional to said movement of said endoscope.

It is another object of the present invention to disclose the system, wherein said joystick unit comprises a touchscreen, such that a touch and a movement on said touchscreen results in movement of said endoscope; further wherein said touch and movement on said touchscreen is proportional to said movement of said endoscope.

It is another object of the present invention to disclose the system, wherein said location within said surgical environment of said human body is determinable from pressure on a portion of said touchscreen.

It is another object of the present invention to disclose the system, wherein said portion of said touchscreen is that which displays an image of said location.

It is another object of the present invention to disclose the system, additionally comprising means configured to restrain the velocity of said endoscope, such that when said means are activated, the velocity of said endoscope is restrained.

It is another object of the present invention to disclose the system, wherein said joystick unit additionally comprises n sensors, where n is an integer larger than one.

It is another object of the present invention to disclose the system, wherein at least one of said n sensors is activated in case of power failure.

It is another object of the present invention to disclose the system, wherein at least one of said n sensors is activated when said system is connected to power.

It is another object of the present invention to disclose the system, wherein said sensors are selected from a group consisting of a motion sensor, a heat sensor, an electric sensor, a sound sensor, a pressure sensor, an optical sensor and any combination thereof.

It is another object of the present invention to disclose the system, wherein said joystick unit is characterized by an external surface.

It is another object of the present invention to disclose the system, wherein said at least one motion sensor detects motion upon said external surface.

It is another object of the present invention to disclose the system, wherein said at least one motion sensor detects motion perpendicular to said external surface.

It is another object of the present invention to disclose the system, wherein said at least one heat sensor is configured to sense temperatures in the range of about 35 to about 42 degrees.

It is another object of the present invention to disclose the system, wherein said system is configured to enable maneuvering of said endoscope at such times as said at least one heat sensor senses temperatures in the range of about 35 to about 42 degrees.

It is another object of the present invention to disclose the system, wherein said at least one heat sensor is configured to provide thermal image; said at least one heat sensor is coupled to a processing unit comprising instructions configured, when executed, to provide said system user with said thermal image.

It is another object of the present invention to disclose the system, wherein said system is configured to enable maneuvering of said endoscope at such times as analysis of said image by said processing unit detects the image of a human hand; further wherein said system is configured to prevent maneuvering of said endoscope at such times when said analysis of said image by said processing unit fails to detect an image of a human hand.

It is another object of the present invention to disclose the system, wherein said at least one electric sensor is configured to sense power failure.

It is another object of the present invention to disclose the system, wherein said at least one electric sensor is configured to sense electric conductivity of a human body.

It is another object of the present invention to disclose the system, wherein said system is configured to enable maneuvering of said endoscope at such times when said sensor senses the conductivity of said subject's body; further wherein said system is configured to prevent maneuvering of said endoscope at such times as said sensor fails to sense the conductivity of said subject's body.

It is another object of the present invention to disclose the system, wherein said at least one sound sensor is configured to sense at least one predetermined sound pattern.

It is another object of the present invention to disclose the system, wherein said endoscope is maneuverable according to said at least one predetermined sound pattern sensed by said at least one sound sensor.

It is another object of the present invention to disclose the system, wherein said at least one pressure sensor is configured to sense pressure applied to said joystick unit.

It is another object of the present invention to disclose the system, wherein said pressure sensed by said at least one pressure sensor affects the system for maneuvering an endoscope (SFME) in a manner selected from a group consisting of: when said pressure sensed by said at least one pressure sensor is above a predetermined value, said SFME is activated; when said pressure sensed by said at least one pressure sensor is above a predetermined value, said SFME is de-activated; and when said pressure sensed by said at least one pressure sensor is below a predetermined value, said SFME is de-activated.

It is another object of the present invention to disclose the system, wherein said at least one optical sensor is configured to sense visual changes according to at least one predetermined visual pattern.

It is another object of the present invention to disclose the system, wherein said endoscope is maneuverable according to said at least one predetermined visual pattern.

It is another object of the present invention to disclose the system, additionally comprising an interface system configured to enable communication between said joystick unit and said maneuvering system.

It is another object of the present invention to disclose the system, wherein said communication means comprises a member selected from a group consisting of a wired communication means, a wireless communication means and any combination thereof.

It is another object of the present invention to disclose the system, wherein said SFME comprises at least one second joystick unit configured to zoom the endoscope by means of said maneuvering system.

It is another object of the present invention to disclose the system, wherein a single device comprises said joystick unit and said second joystick unit.

It is another object of the present invention to disclose the system, wherein said second joystick unit is wearable by said system user.

It is another object of the present invention to disclose the system, wherein said second joystick unit is coupled to at least one surgical tool.

It is another object of the present invention to disclose the system, wherein said at least one surgical tool is said endoscope.

It is another object of the present invention to disclose the system, wherein said at least one joystick unit is configured to control and to direct said endoscope via said maneuvering system on a surgical tool.

It is another object of the present invention to disclose the system, wherein selection of said at least one surgical tool is obtained by activating said at least one joystick unit; further wherein the activation of said at least one joystick unit is obtained by depression of said joystick unit, voice activating the same, prolonged depression on the same, double clicking on the same and any combination thereof.

It is another object of the present invention to disclose the system, wherein said endoscope comprises at least one proximity sensor positioned on an outer circumference of the same.

It is another object of the present invention to disclose the system, additionally comprising a set of instructions which, when executed by data processing apparatus, are configured to control said maneuvering of said endoscope.

It is another object of the present invention to disclose the system, wherein said instructions comprise a predetermined set of rules selected from a group consisting of: most used tool rule, right tool rule, left tool rule, field of view rule, no fly zone rule, a route rule, environmental rule, operator input rule, proximity rule; collision prevention rule, history-based rule, tool-dependent ALLOWED and RESTRICTED movements rule, preferred volume zone rule, preferred tool rule, movement detection rule, tagged tool rule, change of speed rule and any combination thereof.

It is another object of the present invention to disclose the system, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said ALLOWED movements are movements in which said at least one surgical tool is located substantially in at least one of said n 3D spatial positions of said predefined route, and said RESTRICTED movements are movements in which said location of said at least one surgical tool is substantially different from said n 3D spatial positions of said predefined route.

It is another object of the present invention to disclose the system, wherein said environmental rule comprises a comprises a communicable database; said communicable database configured to receive at least one real-time image of said surgical environment and is configured to perform real-time image processing of the same and to determine the 3D spatial position of hazards or obstacles in said surgical environment; said environmental rule is configured to determine said ALLOWED and RESTRICTED movements according to said hazards or obstacles in said surgical environment, such that said RESTRICTED movements are movements in which said at least one surgical tool is located substantially in at least one of said 3D spatial positions, and said ALLOWED movements are movements in which the location of said at least one surgical tool is substantially different from said 3D spatial positions.

It is another object of the present invention to disclose the system, wherein said hazards or obstacles in said surgical environment are selected from a group consisting of tissue, a surgical tool, an organ, an endoscope and any combination thereof.

It is another object of the present invention to disclose the system, wherein said operator input rule comprises a communicable database; said communicable database is configured to receive an input from the operator of said system regarding said ALLOWED and RESTRICTED movements of said at least one surgical tool.

It is another object of the present invention to disclose the system, wherein said input comprises n 3D spatial positions; n is an integer greater than or equal to 2; wherein at least one of which is defined as ALLOWED location and at least one of which is defined as RESTRICTED location, such that said ALLOWED movements are movements in which said at least one surgical tool is located substantially in at least one of said n 3D spatial positions, and said RESTRICTED movements are movements in which the location of said at least one surgical tool is substantially different from said n 3D spatial positions.

It is another object of the present invention to disclose the system, wherein said input comprises at least one rule according to which ALLOWED and RESTRICTED movements of said at least one surgical tool are determined, such that the spatial position of said at least one surgical tool is controlled by said controller according to said ALLOWED and RESTRICTED movements.

It is another object of the present invention to disclose the system, wherein said predetermined set of rules comprises at least one rule selected from a group consisting of: most used tool, right tool rule, left tool rule, field of view rule, no fly zone rule, route rule, environmental rule, operator input rule, proximity rule, collision prevention rule, preferred volume zone rule, preferred tool rule, movement detection rule, history-based rule, tool-dependent ALLOWED and RESTRICTED movements rule, and any combination thereof.

It is another object of the present invention to disclose the system, wherein said operator input rule converts an ALLOWED movement to a RESTRICTED movement and a RESTRICTED movement to an ALLOWED movement.

It is another object of the present invention to disclose the system, wherein said proximity rule is configured to define a predetermined distance between at least two surgical tools; said ALLOWED movements are movements which are within the range or out of the range of said predetermined distance, and said RESTRICTED movements are movements which are out of the range or within the range of said predetermined distance.

It is another object of the present invention to disclose the system, wherein said proximity rule is configured to define a predetermined angle between at least three surgical tools; said ALLOWED movements are movements which are within the range or out of the range of said predetermined angle, and said RESTRICTED movements which are out of the range or within the range of said predetermined angle.

It is another object of the present invention to disclose the system, wherein said collision prevention rule is configured to define a predetermined distance between said at least one surgical tool and an anatomical element within said surgical environment; said ALLOWED movements are movements which are in a range that is larger than said predetermined distance, and said RESTRICTED movements are movements which is in a range that is smaller than said predetermined distance.

It is another object of the present invention to disclose the system, wherein said anatomical element is selected from a group consisting of tissue, organ, another surgical tool and any combination thereof.

It is another object of the present invention to disclose the system, wherein said right tool rule is configured to determine said ALLOWED movement of said endoscope according to the movement of the surgical tool positioned to right of said endoscope; further wherein said left tool rule is configured to determine said ALLOWED movement of said endoscope according to the movement of the surgical tool positioned to left of said endoscope.

It is another object of the present invention to disclose the system, wherein said tagged tool rule comprises means configured to tag at least one surgical tool within said surgical environment and to determine said ALLOWED movement of said endoscope so as to constantly track the movement of said tagged surgical tool.

It is another object of the present invention to disclose the system, wherein said field of view rule comprises a communicable database comprising n 3D spatial positions; n is an integer greater than or equal to 2; the combination of all of said n 3D spatial positions provides a predetermined field of view; said field of view rule is configured to determine said ALLOWED movement of said endoscope within said n 3D spatial positions so as to maintain a constant field of view, such that said ALLOWED movements are movements in which said endoscope is located substantially in at least one of said n 3D spatial positions, and said RESTRICTED movements are movements in which the location of said endoscope is substantially different from said n 3D spatial positions.

It is another object of the present invention to disclose the system, wherein said preferred volume zone rule comprises a communicable database comprising n 3D spatial positions; n is an integer greater than or equal to 2; said n 3D spatial positions provides said preferred volume zone; said preferred volume zone rule is configured to determine said ALLOWED movement of said endoscope within said n 3D spatial positions and RESTRICTED movement of said endoscope outside said n 3D spatial positions, such that said ALLOWED movements are movements in which said endoscope is located substantially in at least one of said n 3D spatial positions, and said RESTRICTED movements are movements in which the location of said endoscope is substantially different from said n 3D spatial positions.

It is another object of the present invention to disclose the system, wherein said preferred tool rule comprises a communicable database, said database stores a preferred tool; said preferred tool rule is configured to determine said ALLOWED movement of said endoscope to constantly track the movement of said preferred tool.

It is another object of the present invention to disclose the system, wherein said no fly zone rule comprises a communicable database comprising n 3D spatial positions; n is an integer greater than or equal to 2; said n 3D spatial positions define a predetermined volume within said surgical environment; said no fly zone rule is configured to determine said RESTRICTED movement if said movement is within said no fly zone and ALLOWED movement if said movement is outside said no fly zone, such that said RESTRICTED movements are movements in which said at least one of said surgical tool is located substantially in at least one of said n 3D spatial positions, and said ALLOWED movements are movements in which the location of said at least one endoscope is substantially different from said n 3D spatial positions.

It is another object of the present invention to disclose the system, wherein said most used tool rule comprises a communicable database counting the amount of movement of each said surgical tool; said most used tool rule is configured to constantly position said endoscope to track the movement of the most moved surgical tool.

It is another object of the present invention to disclose the system, wherein said system further comprises a maneuvering subsystem communicable with said controller, said maneuvering subsystem is configured to spatially reposition said at least one surgical tool during a surgery according to said predetermined set of rules; further wherein said system is configured to alert the physician of said RESTRICTED movement of said at least one surgical tool.

It is another object of the present invention to disclose the system, wherein said alert is selected from a group consisting of audio signaling, voice signaling, light signaling, flashing signaling and any combination thereof.

It is another object of the present invention to disclose the system, wherein said ALLOWED movement is permitted by said controller and said RESTRICTED movement is denied by said controller.

It is another object of the present invention to disclose the system, wherein said history-based rule comprises a communicable database storing each 3D spatial position of each said surgical tool, such that each movement of each surgical tool is stored; said history-based rule is configured to determine said ALLOWED and RESTRICTED movements according to historical movements of said at least one surgical tool, such that said ALLOWED movements are movements in which said at least one surgical tool is located substantially in at least one of said 3D spatial positions, and said RESTRICTED movements are movements in which the location of said at least one surgical tool is substantially different from said 3D spatial positions.

It is another object of the present invention to disclose the system, wherein said tool-dependent ALLOWED and RESTRICTED movements rule comprises a communicable database; said communicable database is configured to store predetermined characteristics of at least one of said surgical tool; said tool-dependent ALLOWED and RESTRICTED movements rule is configured to determine said ALLOWED and RESTRICTED movements according to said predetermined characteristics of said surgical tool; such that ALLOWED movements are movements of said endoscope which track said surgical tool having said predetermined characteristics.

It is another object of the present invention to disclose the system, wherein said predetermined characteristics of said surgical tool are selected from a group consisting of: physical dimensions, structure, weight, sharpness, and any combination thereof.

It is another object of the present invention to disclose the system, wherein said movement detection rule comprises a communicable database comprising the real-time 3D spatial positions of each said surgical tool; said movement detection rule is configured to detect movement of said at least one surgical tool when a change in said 3D spatial positions is received, such that said ALLOWED movements are movements in which said endoscope is re-directed to focus on said moving surgical tool.

It is another object of the present invention to disclose the system, wherein, for each said instructing function, there exists a weighting function, said weighting function, order of execution of said instructions selectable by said weighting function.

It is another object of the present invention to disclose the system, further comprising a maneuvering subsystem communicable with said controller, said maneuvering subsystem is configured to spatially reposition said at least one surgical tool during a surgery according to said predetermined set of rules, such that if said movement of said at least one surgical tool is a RESTRICTED movement, said maneuvering subsystem prevents said movement.

It is another object of the present invention to disclose the system, additionally comprising
(a) at least one wearable operator comprising at least one wireless transmitter, configured to transmit a signal once said at least one wearable operator is activated; said at least one wearable operator is either wire or wirelessly in communication with at least one surgical instrument;
(b) at least one wireless receiver; configured to receive said signal sent by said transmitter;
(c) at least one laparoscopy computerized system, in communication with said wireless receiver, configured to provide a visual onscreen depiction of said at least one instrument to be selected following the activation of said at least one wearable operator; and,
(d) at least one video screen; wherein said system is configured to control and to direct said endoscope via said laparoscopy computerized system and said maneuvering system on said instrument to be selected following the activation of said at least one wearable operator.

It is another object of the present invention to disclose the system, wherein said communication between said at least one of said wearable operators and said instrument is either wire or wirelessly coupling.

It is another object of the present invention to disclose the system, wherein said wearable operator is worn by said surgeon on a predetermined body part.

It is another object of the present invention to disclose the system, wherein said predetermined body part is selected from a group consisting of: the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the present invention to disclose the system, wherein the shape of said wearable operator is selected from a group consisting of a ring, a bracelet and any combination thereof.

It is another object of the present invention to disclose the system, wherein said wearable operator is coupled to a predetermined location on said instrument by means of an adaptor.

It is another object of the present invention to disclose the system, wherein said wearable operator is adjustable so as to fit said predetermined location of said different instruments, each of which is characterized by a different size and shape.

It is another object of the present invention to disclose the system, wherein said wearable operator comprises a body having at least two portions at least partially overlapping each other; said two portions are configured to grasp and hold either said instrument or said predetermined body part there-between, such that a tight-fit coupling between said two portions and said instrument or said predetermined body part is obtained.

It is another object of the present invention to disclose the system, wherein one of said two portions is rotationally movable relative to the other, such that when said wearable operator is coupled to said instrument, fine-tuned movement of said two body portions is obtainable so as to provide said tight-fit coupling between said two portions and said instrument or said predetermined body part.

It is another object of the present invention to disclose the system, wherein said two portions are rotationally movable relative to each other, such that when said wearable operator is coupled to said instrument, fine-tuned movement of said two body portions is obtainable so as to provide said tight-fit coupling between said two portions and said instrument or said predetermined body part.

It is another object of the present invention to disclose the system, wherein said wearable operator comprises (a) at least one flexible and stretchable strip; and (b) loop-closing means configured to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of which is characterized by a different size and shape.

It is another object of the present invention to disclose the system, wherein said flexible and stretchable strip is made of material selected from a group consisting of silicone, rubber and any combination thereof.

It is another object of the present invention to disclose the system, wherein said wireless transmitter is configured to locate the position of at least one of said instruments.

It is another object of the present invention to disclose the system, wherein selection of said at least one instrument is obtained by activating said at least one wearable operator; further wherein the activation of said at least one wearable operator is obtained by depression on a predetermined location in said wearable operator, voice activating the same, prolonged depression on the same, double clicking on the same and any combination thereof.

It is another object of the present invention to disclose the system, wherein said laparoscopy computerized system directs said endoscope by using image information shown on said video screen without said help of assistants.

It is another object of the present invention to disclose the system, wherein said conventional laparoscopy computerized system comprises at least one surgical instrument spatial location software, configured to locate the 3D spatial position of said at least one instrument; further wherein said conventional laparoscopy computerized system comprises at least one automated assistant maneuvering system; said automated assistant maneuvering system is coupled to said endoscope and is configured to direct said endoscope to said at least one instrument, said instrument selected following the activation of said at least one wearable operator.

It is another object of the present invention to disclose the system, wherein each transmitted signal from said wearable operator and said wireless transmitter is matched to at least one of said instruments.

It is another object of the present invention to disclose the system, wherein said articulating tool has articulations substantially at the tip of said tool, substantially along the body of said too, and any combination thereof.

It is another object of the present invention to disclose the system, wherein control of articulation is selected from a group consisting of hardware control, software control and any combination thereof.

It is another object of the present invention to disclose the system, wherein said tool has articulation in a regions selected from a group consisting of near the tip of said tool, on the body of said tool, and any combination thereof.

It is another object of the present invention to disclose a method for providing a 3D image of at least one object within a field of view within a body cavity by means of a structured-light based endoscope, comprising steps of:
a. providing a structured-light based endoscope comprising:
  i. at least one endoscope having at least one lens in the endoscope's distal end;
  ii. at least one camera located in the endoscope's proximal end, configured to real-time provide at least one 2D image of at least a portion of said field of view by means of said at least one lens;
  iii. at least one light source, configured to real-time illuminate at least a portion of said at least one object within at least a portion of said field of view with at least one time and space varying predetermined light pattern;
  iv. at least one sensor configured to detect light reflected from said field of view;
  v. a computer program which, when executed by data processing apparatus, is configured to generate a 3D image of said field of view; and,
b. maneuvering said endoscope and controlling the movements of the same;
c. illuminating said at least a portion of said field of view with said at least one time and space varying predetermined light pattern;
d. detecting said light reflected from said field of view;
e. generating, from said light reflected from said field of view, said 3D image of said field of view;
wherein said predetermined light pattern is a structured light pattern; further wherein said 3D image is constructable from said detected light reflected from said field of view and said structured light pattern.

It is another object of the present invention to disclose the method as described above, wherein said system additionally comprising at least one maneuvering system, configured to maneuver said endoscope in at least two degrees of freedom (DOF);

It is another object of the present invention to disclose the method as described above, wherein said endoscope is an articulating endoscope.

It is another object of the present invention to disclose the method, additionally comprising step of constructing said 3D image by calculating the world coordinates of at least one point on said at least one object.

It is another object of the present invention to disclose the method, additionally comprising step of calculating said world coordinates of said at least one point on said at least one object from the following equation:

$$\tilde{\alpha} = \frac{n^T \tilde{x}_p}{n^T R_p v_c},$$

where $n^T$ is the transpose of the normal to the plane defined by the stripe id $x_p$, $\tilde{x}_p = x_p + [\delta x_p, 0, f_p]^T$ is the perturbed stripe id $x_p$, $R_p$ is the rotation matrix defining the transformation between the world coordinate system and the projector coordinate system and $v_c$ is the direction of the ray between the stripe id and the object point.

It is another object of the present invention to disclose the method, additionally comprising step of, for any point $X_w$ in world coordinate system, calculating the coordinate $X_c$ of the same point in the camera coordinate system according to the following equation:

$$X_c = C_c X_w,$$

where $C_c$, the camera perspective projection matrix, is of the form $$C_c = \alpha \begin{bmatrix} f_x & kf_y & x_c^0 \\ 0 & f_y & y_c^0 \\ 0 & 0 & 1 \end{bmatrix} [R_c \ t_c].$$

where $\alpha$ is a proportion coefficient, $f_x$ and $f_y$ are the camera focal length scaled to each of the camera image dimensions, k is the shear of the camera coordinate system, $x_c^0$ and $y_c^0$ are the origin of $X_c$ in image coordinates, and $R_c$ and $t_c$ define the transformation between the world coordinate system and the light source's coordinate system, with $R_c$ being a rotation matrix and $t_c$ a translation matrix.

It is another object of the present invention to disclose the method, additionally comprising step of defining $x_p^0$ to be the x-coordinate of the intersection of the optical axis and the projector It is another object of the present invention to disclose the method, additionally comprising step of, for any point $X_w$ in world coordinate system, calculating the coordinate $X_p$ of the same point in the light source coordinate system according to the following equation:

$$X_p = C_p X_w,$$

where $C_p$, the light source perspective projection matrix, is of the form $$C_p = \alpha \begin{bmatrix} f_p & 0 & x_p^0 \\ 0 & 0 & 1 \end{bmatrix} [R_p \ t_p]$$

where $\alpha$ is a proportion coefficient, $f_p$ is the light source focal length scaled to projector dimensions, $x_p^0$ is the origin of $x_p$ in projector coordinates, and $R_p$ and $t_p$ define the transformation between the world coordinate system and the light source's coordinate system, with $R_p$ being a rotation matrix and $t_p$ a translation matrix.

It is another object of the present invention to disclose the method, additionally comprising step of calculating the world coordinates $p_w$, of a point P according to the following equation:

$$\begin{pmatrix} p_p \\ p_s \end{pmatrix} - \begin{pmatrix} F_c(p_w; \Theta_c) \\ F_p(p_w; \Theta_p) \end{pmatrix} = 0$$

where $p_p=(x_p,y_p)^t$ is the pixel coordinate of said point, $p_x=(x_s)$ is the stripe value of said point P, $F_c(P_w; \Theta_c)=P_s-\in_p$ is the noise-free value of the vector of pixel coordinates, where $P_p$ is the vector of measured pixel coordinates and $\in_p$ is the vector of errors in the pixel coordinates; $F_p(P_w; \Theta P)=P_s-\in_p$ is the noise-free value of the vector of stripe coordinates, where $P_s$ is the vector of measured stripe coordinates and $\in_s$ is the vector of errors in the stripe coordinates.

It is another object of the present invention to disclose the method, additionally comprising step of estimating the world coordinates $p_w$, of a point P according to the following non-linear least squares (NLLS) equations:

$$\min_{\Theta_c}\|P_p - F_c(P_w; \Theta_c)\|^2$$

$$\min_{\Theta_p}\|P_s - F_p(P_w; \Theta_p)\|^2$$

It is another object of the present invention to disclose the method, additionally comprising step of solving said NLLS equations using a NLLS solving algorithm selected from a group consisting of the Gauss-Newton technique, the quasi-Newton technique, and the Levenberg-Marquardt technique.

It is another object of the present invention to disclose the method, additionally comprising a step of calculating the location, in world coordinates, of a kth point on the object according to the following equation $$p_w^k = \frac{C_{1,2,1}^k - x_p C_{3,2,1}^k - y_p C_{1,3,1}^k - x_s C_{1,2,2}^k + x_s x_p C_{3,2,2}^k + x_s y_p C_{1,3,2}^k}{C_{1,2,1}^4 - x_p C_{3,2,1}^4 - y_p C_{1,3,1}^4 - x_s C_{1,2,2}^4 + x_s x_p C_{3,2,2}^4 + x_s y_p C_{1,3,2}^4}$$

Where $(C_c^i, C_c^j, C_c^l, e_k)$ are constants which depend only on a camera perspective transformation matrix and a projector perspective transformation matrix.

It is another object of the present invention to disclose the method, additionally comprising step of providing a calibration object.

It is another object of the present invention to disclose the method, additionally comprising step of providing said calibration object of a predetermined shape and size.

It is another object of the present invention to disclose the method, additionally comprising step of providing said calibration object with fiducial marks at predetermined positions.

It is another object of the present invention to disclose the method, additionally comprising step of selecting said lens to be a wide-angle lens.

It is another object of the present invention to disclose the method, additionally comprising step of selecting said wide-angle lens from a group consisting of a fisheye lens, an omnidirectional lens and any combination thereof.

It is another object of the present invention to disclose the method, additionally comprising step of using at least one of a group consisting of: temporal sequencing, spatial sequencing, wavelength sequencing and any combination thereof in said structured light pattern.

It is another object of the present invention to disclose the method, additionally comprising step of differentiating cancerous tissue from normal tissue by means of said wavelength sequencing.

It is another object of the present invention to disclose the method, additionally comprising step of determining the relationship between the location of a point in said camera image, the location of a point in a light source and the location of a point in space for all said points in said camera image, said points in said light source and said points in space.

It is another object of the present invention to disclose the method, additionally comprising step of using said known relationships to generate said 3D image from said 2D camera image.

It is another object of the present invention to disclose the method, additionally comprising at least one location estimating means configured to real-time locate the 3D spatial position at any given time t of a member of a group consisting of: said endoscope, a surgical tool and any combination thereof.

It is another object of the present invention to disclose the method, additionally comprising steps of providing said at least one location estimating means comprising (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element.

It is another object of the present invention to disclose the method, additionally comprising steps of selecting said at least one location estimating means to be an interface subsystem between a surgeon and said at least one surgical tool, the interface subsystem comprising:
a. at least one array comprising N regular or patterned light sources, where N is a positive integer;
b. at least one array comprising M cameras, each of the M cameras, where M is a positive integer;
c. optional optical markers and means for attaching the optical marker to the at least one surgical tool; and;
d. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to disclose the method, additionally comprising step of displaying said 3D image by means of a member of a group consisting of: a 3D screen, 3D glasses, autostereoscopy, holography, a volumetric display, integral imaging, wiggle stereoscopy, an active shutter 3d system, a polarized 3d system, an interference filter system, a color anaglyph systems a Chromadepth system, an over/under format, and any combination thereof.

It is another object of the present invention to disclose the method, additionally comprising step of detecting said tools by means of depth cues in said 3D image.

It is another object of the present invention to disclose the method, additionally comprising step of detecting at least one structure selected from a group consisting of an organ, a blood vessel, a nerve, a limb and any combination thereof.

It is another object of the present invention to disclose the method, additionally comprising step of emphasizing at least one said structure by means of a member of a group consisting of: virtual reality overlays, color markings, pattern markings, outlines, arrows, and any combination thereof.

It is another object of the present invention to disclose the method, additionally comprising step of storing data from at least one other imaging modality in a database.

It is another object of the present invention to disclose the method, additionally comprising steps of matching and aligning said data from said at least one other imaging modality with said 3D image, and of viewing substantially all information from said at least one other imaging modality and said 3D image as a single 3D image.

It is another object of the present invention to disclose the method, additionally comprising step of selecting said at least one other imaging modality from a group consisting of: CT, MRI, ultrasound and PET and any combination thereof.

It is another object of the present invention to disclose the method, additionally comprising steps of displaying additional information and of selecting said information from a group consisting of: recommendations useful in directing the progress of an operation, information useful in assisting an operator in making a decision, information useful for a record of the operation and any combination thereof.

It is another object of the present invention to disclose the method, additionally comprising step of displaying said information visually or audibly.

It is another object of the present invention to disclose the method, additionally comprising step of selecting said information from a group consisting of: camera pose, body temperature, time, elapsed time since start of operation, patient notes, notes made during the operation, and other information accessible to the system and any combination thereof.

It is another object of the present invention to disclose the method, additionally comprising steps of providing at least one joystick unit in communication with said maneuvering system, and operating said maneuvering system by means of said joystick unit.

It is another object of the present invention to disclose the method, additionally comprising step of operating said joystick, said operating causing motion of said endoscope by means of said maneuvering system.

It is another object of the present invention to disclose the method, wherein said joystick unit is wearable by a user of said system.

It is another object of the present invention to disclose the method, additionally comprising step of coupling said joystick unit to at least one surgical tool used in said medical procedure.

It is another object of the present invention to disclose the method, additionally comprising step of selecting said at least one surgical tool to be said endoscope.

It is another object of the present invention to disclose the method, additionally comprising step of selecting said movement of said joystick to be proportional to said movement of said endoscope.

It is another object of the present invention to disclose the method, additionally comprising step of setting said endoscope's speed to a predetermined value if said joystick unit's speed of motion is above a predetermined value.

It is another object of the present invention to disclose the method, additionally comprising step of selecting said joystick unit to be a force joystick.

It is another object of the present invention to disclose the method, additionally comprising step of comprising said joystick unit of a base and lever coupled to said base, such that moving said lever results in movement of said endoscope; said movement of said lever being proportional to said movement of said endoscope.

It is another object of the present invention to disclose the method, additionally comprising steps of comprising said joystick unit of a base and a button; and jointly connecting said button to said base, such that moving of said button results in movement of said endoscope; said movement of said button being proportional to said movement of said endoscope.

It is another object of the present invention to disclose the method, additionally comprising step of comprising said joystick unit of a touchscreen, such that a touching and moving on said touchscreen results in movement of said endoscope; touch and movement on said touchscreen being proportional to said movement of said endoscope.

It is another object of the present invention to disclose the method, additionally comprising step of determining said location within said surgical environment of said human body from pressure on a portion of said touchscreen.

It is another object of the present invention to disclose the method, wherein said portion of said touchscreen is that which displays an image of said location.

It is another object of the present invention to disclose the method, additionally comprising means configured to restrain the velocity of said endoscope, such that when said means are activated, the velocity of said endoscope is restrained.

It is another object of the present invention to disclose the method, additionally comprising step of providing said joystick unit comprising n sensors, where n is an integer larger than one.

It is another object of the present invention to disclose the method, additionally comprising step of activating at least one of said n sensors in case of power failure.

It is another object of the present invention to disclose the method, additionally comprising step of activating at least one of said n sensors when said system is connected to power.

It is another object of the present invention to disclose the method, additionally comprising step of selecting said sensors from a group consisting of a motion sensor, a heat sensor, an electric sensor, a sound sensor, a pressure sensor, an optical sensor and any combination thereof.

It is another object of the present invention to disclose the method, additionally comprising step of characterizing said joystick unit by an external surface.

It is another object of the present invention to disclose the method, additionally comprising step of detecting motion upon said external surface by means of said at least one motion sensor.

It is another object of the present invention to disclose the method, additionally comprising step of detecting motion perpendicular to said external surface by means of said at least one motion sensor.

It is another object of the present invention to disclose the method, additionally comprising step of sensing temperatures in the range of about 35 to about 42 degrees by means of said at least one heat sensor.

It is another object of the present invention to disclose the method, additionally comprising step of maneuvering of said endoscope at such times as said at least one heat sensor senses temperatures in the range of about 35 to about 42 degrees.

It is another object of the present invention to disclose the method, additionally comprising step of coupling said at least one heat sensor to a processing unit comprising instructions configured, when executed, to provide said system user with a thermal image.

It is another object of the present invention to disclose the method, additionally comprising steps of maneuvering said endoscope at such times as analysis of said image by said processing unit detects an image of a human hand; and preventing maneuvering of said endoscope at such times as said analysis of said image by said processing unit fails to detect said image of said human hand.

It is another object of the present invention to disclose the method, additionally comprising step of sensing power failure by means of said at least one electric sensor.

It is another object of the present invention to disclose the method, additionally comprising step of sensing electric conductivity of a human body by means of said at least one electric sensor.

It is another object of the present invention to disclose the method, additionally comprising steps of maneuvering said endoscope at such times as said sensor senses the conductivity of said subject's body; and preventing maneuvering of said endoscope at such times as said sensor fails to sense the conductivity of said subject's body.

It is another object of the present invention to disclose the method, additionally comprising step of sensing at least one predetermined sound pattern by means of said at least one sound sensor.

It is another object of the present invention to disclose the method, additionally comprising step of maneuvering said endoscope according to said at least one predetermined sound pattern sensed by said at least one sound sensor.

It is another object of the present invention to disclose the method, additionally comprising step of sensing pressure applied to said joystick unit by means of said at least one pressure sensor.

It is another object of the present invention to disclose the method, additionally comprising step of selecting response of said system for maneuvering an endoscope (SFME) to said pressure sensed by said at least one pressure sensor from a group consisting of: activating said SFME when said pressure sensed by said at least one pressure sensor is above a predetermined value; de-activating said SFME when said pressure sensed by said at least one pressure sensor is above a predetermined value; and de-activating said SFME when said pressure sensed by said at least one pressure sensor is below a predetermined value.

It is another object of the present invention to disclose the method, additionally comprising step of sensing visual changes according to at least one predetermined visual pattern by means of said at least one optical sensor.

It is another object of the present invention to disclose the method, additionally comprising step of maneuvering said endoscope according to said at least one predetermined visual pattern.

It is another object of the present invention to disclose the method, additionally comprising step of providing an interface system configured to enable communication between said joystick unit and said maneuvering system.

It is another object of the present invention to disclose the method, additionally comprising step of selecting said communication means from a group consisting of a wired communication means, a wireless communication means and any combination thereof.

It is another object of the present invention to disclose the method, additionally comprising steps of providing at least one second joystick unit and configuring said second joystick unit to zoom said endoscope by means of said maneuvering system.

It is another object of the present invention to disclose the method, additionally comprising step of providing a single device comprising said joystick unit and said second joystick unit.

It is another object of the present invention to disclose the method, additionally comprising step of wearing said second joystick unit by said system user.

It is another object of the present invention to disclose the method, additionally comprising step of coupling said second joystick unit to at least one surgical tool.

It is another object of the present invention to disclose the method, additionally comprising step of providing said at least one surgical tool to be said endoscope.

It is another object of the present invention to disclose the method, additionally comprising step of controlling and directing said endoscope by means of said at least one joystick unit via said maneuvering system.

It is another object of the present invention to disclose the method, additionally comprising steps of selecting said at least one surgical tool by activating said at least one joystick unit; activating said at least one joystick unit by at least one of a group consisting of: depressing said joystick unit, voice activating the same, prolonged depressing of the same, double clicking on the same and any combination thereof.

It is another object of the present invention to disclose the method, additionally comprising step of positioning at least one proximity sensor on an outer circumference of said tool.

It is another object of the present invention to disclose the method, additionally comprising steps of providing a set of instructions which, when executed by data processing apparatus, and executing said instructions, thereby controlling said maneuvering of said endoscope.

It is another object of the present invention to disclose the method, additionally comprising step of selecting said instructions from a predetermined set of rules selected from a group consisting of: most used tool rule, right tool rule, left tool rule, field of view rule, no fly zone rule, a route rule, environmental rule, operator input rule, proximity rule; collision prevention rule, history-based rule, tool-dependent ALLOWED and RESTRICTED movements rule, preferred volume zone rule, preferred tool rule, movement detection rule, tagged tool rule, change of speed rule and any combination thereof.

It is another object of the present invention to disclose the method, wherein said route rule comprises steps of: providing a communicable database; storing a predefined route in which said at least one surgical tool is configured to move within said surgical environment; comprising said predefined route of n 3D spatial positions of said at least one surgical tool, n is an integer greater than or equal to 2; said ALLOWED movements are movements in which said at least one surgical tool is located substantially in at least one of said n 3D spatial positions of said predefined route, and said RESTRICTED movements are movements in which said location of said at least one surgical tool is substantially different from said n 3D spatial positions of said predefined route.

It is another object of the present invention to disclose the method, wherein said environmental rule comprises steps of: providing a communicable database; receiving at least one real-time image of said surgical environment in said communicable database; performing real-time image processing of the same and determining the 3D spatial position of hazards or obstacles in said surgical environment; determining said ALLOWED and RESTRICTED movements according to said hazards or obstacles in said surgical environment, such that said RESTRICTED movements are movements in which said at least one surgical tool is located substantially in at least one of said 3D spatial positions, and said ALLOWED movements are movements in which the location of said at least one surgical tool is substantially different from said 3D spatial positions.

It is another object of the present invention to disclose the method, additionally comprising steps of selecting said hazards or obstacles in said surgical environment from a group consisting of tissue, a surgical tool, an organ, an endoscope and any combination thereof.

It is another object of the present invention to disclose the method, wherein said operator input rule comprises steps of: providing a communicable database; and receiving input from an operator of said system regarding said ALLOWED and RESTRICTED movements of said at least one surgical tool.

It is another object of the present invention to disclose the method, additionally comprising steps of: comprising said input of n 3D spatial positions, n is an integer greater than or equal to 2; defining at least one of said spatial positions as an ALLOWED location; defining at least one of said spatial positions as a RESTRICTED location; such that said ALLOWED movements are movements in which said at least one surgical tool is located substantially in at least one of said n 3D spatial positions, and said RESTRICTED movements are movements in which the location of said at least one surgical tool is substantially different from said n 3D spatial positions.

It is another object of the present invention to disclose the method, additionally comprising steps of: comprising said input of at least one rule according to which ALLOWED and RESTRICTED movements of said at least one surgical tool are determined, such that the spatial position of said at least one surgical tool is controlled by said controller according to said ALLOWED and RESTRICTED movements.

It is another object of the present invention to disclose the method, additionally comprising steps of selecting said predetermined set of rules from a group consisting of: most used tool, right tool rule, left tool rule, field of view rule, no fly zone rule, route rule, environmental rule, operator input rule, proximity rule, collision prevention rule, preferred volume zone rule, preferred tool rule, movement detection rule, history-based rule, tool-dependent ALLOWED and RESTRICTED movements rule, and any combination thereof.

It is another object of the present invention to disclose the method, wherein said operator input rule comprises steps of: converting an ALLOWED movement to a RESTRICTED movement and converting a RESTRICTED movement to an ALLOWED movement.

It is another object of the present invention to disclose the method, wherein said proximity rule comprises steps of: defining a predetermined distance between at least two surgical tools; said ALLOWED movements are movements which are within the range or out of the range of said predetermined distance, and said RESTRICTED movements are movements which are out of the range or within the range of said predetermined distance.

It is another object of the present invention to disclose the method, wherein said proximity rule comprises steps of: defining a predetermined angle between at least three surgical tools; said ALLOWED movements are movements which are within the range or out of the range of said predetermined angle, and said RESTRICTED movements are movements which are out of the range or within the range of said predetermined angle.

It is another object of the present invention to disclose the method, wherein said collision prevention rule comprises steps of: defining a predetermined distance between said at least one surgical tool and an anatomical element within said surgical environment; said ALLOWED movements are movements which are in a range that is larger than said predetermined distance, and said RESTRICTED movements are movements which is in a range that is smaller than said predetermined distance.

It is another object of the present invention to disclose the method, additionally comprising steps of selecting said anatomical element from a group consisting of tissue, organ, another surgical tool and any combination thereof.

It is another object of the present invention to disclose the method, wherein said right tool rule comprises steps of: determining said ALLOWED movement of said endoscope according to the movement of the surgical tool positioned to right of said endoscope; further wherein said left tool rule comprises steps of: determining said ALLOWED movement of said endoscope according to the movement of the surgical tool positioned to left of said endoscope.

It is another object of the present invention to disclose the method, wherein said tagged tool rule comprises steps of: tagging at least one surgical tool within said surgical environment and determining said ALLOWED movements of said endoscope to be movements that constantly track the movement of said tagged surgical tool.

It is another object of the present invention to disclose the method, wherein said field of view rule comprises steps of: providing a communicable database comprising n 3D spatial positions; n is an integer greater than or equal to 2; generating a field of view from the combination of all of said n 3D spatial positions; maintaining a constant field of view by determining said ALLOWED movement of said endoscope to be within said n 3D spatial positions, such that said ALLOWED movements are movements in which said endoscope is located substantially in at least one of said n 3D spatial positions, and said RESTRICTED movements are movements in which the location of said endoscope is substantially different from said n 3D spatial positions.

It is another object of the present invention to disclose the method, wherein said preferred volume zone rule comprises steps of: providing a communicable database comprising n 3D spatial positions; n is an integer greater than or equal to 2; generating said preferred volume zone from said n 3D spatial positions; determining said ALLOWED movement of said endoscope to be within said n 3D spatial positions and said RESTRICTED movement of said endoscope to be outside said n 3D spatial positions, such that said ALLOWED movements are movements in which said endoscope is located substantially in at least one of said n 3D spatial positions, and said RESTRICTED movements are movements in which the location of said endoscope is substantially different from said n 3D spatial positions.

It is another object of the present invention to disclose the method, wherein said preferred tool rule comprises steps of: providing a communicable database, storing a preferred tool in said database; determining said ALLOWED movement of said endoscope so as to constantly track the movement of said preferred tool.

It is another object of the present invention to disclose the method, wherein said no fly zone rule comprises steps of: providing a communicable database comprising n 3D spatial positions, n is an integer greater than or equal to 2; defining a predetermined volume within said surgical environment from said n 3D spatial positions; determining said RESTRICTED movement to be said movement within said no fly zone; determining said ALLOWED movement to be said movement outside said no fly zone, such that said RESTRICTED movements are movements in which said at least one of said surgical tool is located substantially in at least one of said n 3D spatial positions, and said ALLOWED movements are movements in which the location of said at least one endoscope is substantially different from said n 3D spatial positions.

It is another object of the present invention to disclose the method, wherein said most used tool rule comprises steps of: providing a communicable database; counting the amount of movement of each said surgical tool; constantly positioning said endoscope to track movement of the most moved surgical tool.

It is another object of the present invention to disclose the method, additionally comprising steps of providing a maneuvering subsystem communicable with said controller, spatially repositioning said at least one surgical tool during a surgery according to said predetermined set of rules; and alerting the physician of said RESTRICTED movement of said at least one surgical tool.

It is another object of the present invention to disclose the method, additionally comprising steps of selecting said alert from a group consisting of: audio signaling, voice signaling, light signaling, flashing signaling and any combination thereof.

It is another object of the present invention to disclose the method, additionally comprising steps of defining said ALLOWED movement as a movement permitted by said controller and defining said RESTRICTED movement as a movement denied by said controller.

It is another object of the present invention to disclose the method, wherein said history-based rule comprises steps of: providing a communicable database storing each 3D spatial position of each said surgical tool, such that each movement of each surgical tool is stored; determining said ALLOWED and RESTRICTED movements according to historical movements of said at least one surgical tool, such that said ALLOWED movements are movements in which said at least one surgical tool is located substantially in at least one of said 3D spatial positions, and said RESTRICTED movements are movements in which the location of said at least one surgical tool is substantially different from said 3D spatial positions.

It is another object of the present invention to disclose the method, wherein said tool-dependent ALLOWED and RESTRICTED movements rule comprises steps of: providing a communicable database; storing predetermined characteristics of at least one said surgical tool; determining said ALLOWED and RESTRICTED movements according to said predetermined characteristics of said surgical tool; such that ALLOWED movements are movements of said endoscope which track said surgical tool having said predetermined characteristics.

It is another object of the present invention to disclose the method, additionally comprising step of selecting said predetermined characteristics of said surgical tool from a group consisting of: physical dimensions, structure, weight, sharpness, and any combination thereof.

It is another object of the present invention to disclose the method, wherein said movement detection rule comprises steps of: providing a communicable database comprising the real-time 3D spatial positions of each said surgical tool; detecting movement of said at least one surgical tool when a change in said 3D spatial positions is received, such that said ALLOWED movements are movements in which said endoscope is re-directed to focus on said moving surgical tool.

It is another object of the present invention to disclose the method, additionally comprising steps of providing a maneuvering subsystem communicable with said controller, spatially repositioning said at least one surgical tool during a surgery according to said predetermined set of rules, such that if said movement of said at least one surgical tool is a RESTRICTED movement, said maneuvering subsystem prevents said movement.

It is another object of the present invention to disclose the method, additionally comprising step of providing, for each said instructing function, a weighting function, said weighting function, order of execution of said instructions selectable by said weighting function It is another object of the present invention to disclose the method, additionally comprising steps of providing:
(a) at least one wearable operator comprising at least one wireless transmitter, configured to transmit a signal once said at least one wearable operator is activated; said at least one wearable operator is either wire or wirelessly in communication with at least one surgical instrument;
(b) at least one wireless receiver; configured to receive said signal sent by said transmitter;
(c) at least one laparoscopy computerized system, in communication with said wireless receiver, configured to provide a visual onscreen depiction of said at least one instrument to be selected following the activation of said at least one wearable operator; and,
(d) at least one video screen; wherein said system is configured to control and to direct said endoscope via said laparoscopy computerized system and said maneuvering system on said instrument to be selected following the activation of said at least one wearable operator.

It is another object of the present invention to disclose the method, additionally comprising step of providing said communication between said at least one of said wearable operators and said instrument by means of either wire or wirelessly coupling.

It is another object of the present invention to disclose the method, additionally comprising step of wearing said wearable operator by said surgeon on a predetermined body part.

It is another object of the present invention to disclose the method, additionally comprising step of selecting said predetermined body part from a group consisting of: the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the present invention to disclose the method, additionally comprising step of selecting shape of said wearable operator from a group consisting of a ring, a bracelet and any combination thereof.

It is another object of the present invention to disclose the method, additionally comprising step of coupling said wearable operator to a predetermined location on said instrument by means of an adaptor.

It is another object of the present invention to disclose the method, additionally comprising step of adjusting said wearable operator so as to fit said predetermined location of said different instruments, each of which is characterized by a different size and shape.

It is another object of the present invention to disclose the method, additionally comprising steps of comprising said wearable operator of a body having at least two portions at least partially overlapping each other; and configuring said two portions to grasp and hold either said instrument or said predetermined body part there-between, thereby obtaining a tight-fit coupling between said two portions and said instrument or said predetermined body part.

It is another object of the present invention to disclose the method, additionally comprising steps of coupling said wearable operator to said instrument; and rotating one of said two portions relative to the other, such that fine-tuned movement of said two body portions is obtained; thereby providing said tight-fit coupling between said two portions and said instrument or said predetermined body part.

It is another object of the present invention to disclose the method, additionally comprising steps of coupling said wearable operator to said instrument; and rotating said two portions relative to each other, such that fine-tuned movement of said two body portions is obtained; thereby providing said tight-fit coupling between said two portions and said instrument or said predetermined body part.

It is another object of the present invention to disclose the method, additionally comprising step of comprising said wearable operator of (a) at least one flexible and stretchable strip; and (b) loop-closing means configured to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of which is characterized by a different size and shape.

It is another object of the present invention to disclose the method, additionally comprising step of selecting material for said flexible and stretchable strip from a group consisting of silicone, rubber and any combination thereof.

It is another object of the present invention to disclose the method, additionally comprising step of configuring said wireless transmitter to locate the position of at least one of said instruments.

It is another object of the present invention to disclose the method, additionally comprising step of selecting of said at least one instrument from a group consisting of: activating said at least one wearable operator; depressing on a predetermined location in said wearable operator, voice activating the same, prolonged depression on the same, double clicking on the same and any combination thereof.

It is another object of the present invention to disclose the method, additionally comprising step of directing said endoscope by using image information shown on said video screen without said help of assistants.

It is another object of the present invention to disclose the method, additionally comprising steps of comprising said conventional laparoscopy computerized system of at least one surgical instrument spatial location software, configured to locate the 3D spatial position of said at least one instrument; comprising said conventional laparoscopy computerized system of at least one automated assistant maneuvering system; coupling said automated assistant maneuvering system to said endoscope; activating said at least one wearable operator; selecting said at least one instrument; and directing said endoscope to said at least one instrument.

It is another object of the present invention to disclose the method, additionally comprising step of matching each transmitted signal from said wearable operator and said wireless transmitter to at least one of said instruments.

It is another object of the present invention to disclose the method, additionally comprising steps of providing said tool with articulations, the location of said articulations selected from a group consisting of: substantially at the tip of said tool, substantially along the body of said tool, and any combination thereof.

It is another object of the present invention to disclose the method, additionally comprising steps of controlling articulation by means of a method selected from a group consisting of hardware control, software control and any combination thereof.

It is another object of the present invention to disclose the method, additionally comprising steps of providing a tool articulated at a region selected from a group consisting of near the tip of said tool, on the body of said tool, and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1 schematically illustrates a structured light system;

FIG. 6A-D depicts $I_H$, $I_L$, the MSB pattern and the LSB pattern for an embodiment of the system;

FIG. 7A-E shows the raw image corresponding to one embodiment of a stripe pattern, the normalized intensity image for that stripe pattern, the binary image for that stripe pattern, the fidelity image for that stripe pattern and profiles of a vertical line from the normalized intensity image for an embodiment of the system;

FIG. 28 schematically illustrates a system for controlling the field of view on an endoscope;

FIG. 29 presents a means to control the articulation of an articulating endoscope;

FIG. 46A-B schematically illustrates movement of an articulated tool; and

FIG. 47 schematically illustrates movement of an articulated tool.

DETAILED DESCRIPTION OF THE PREFERRED EMBODIMENTS

Figure 1:
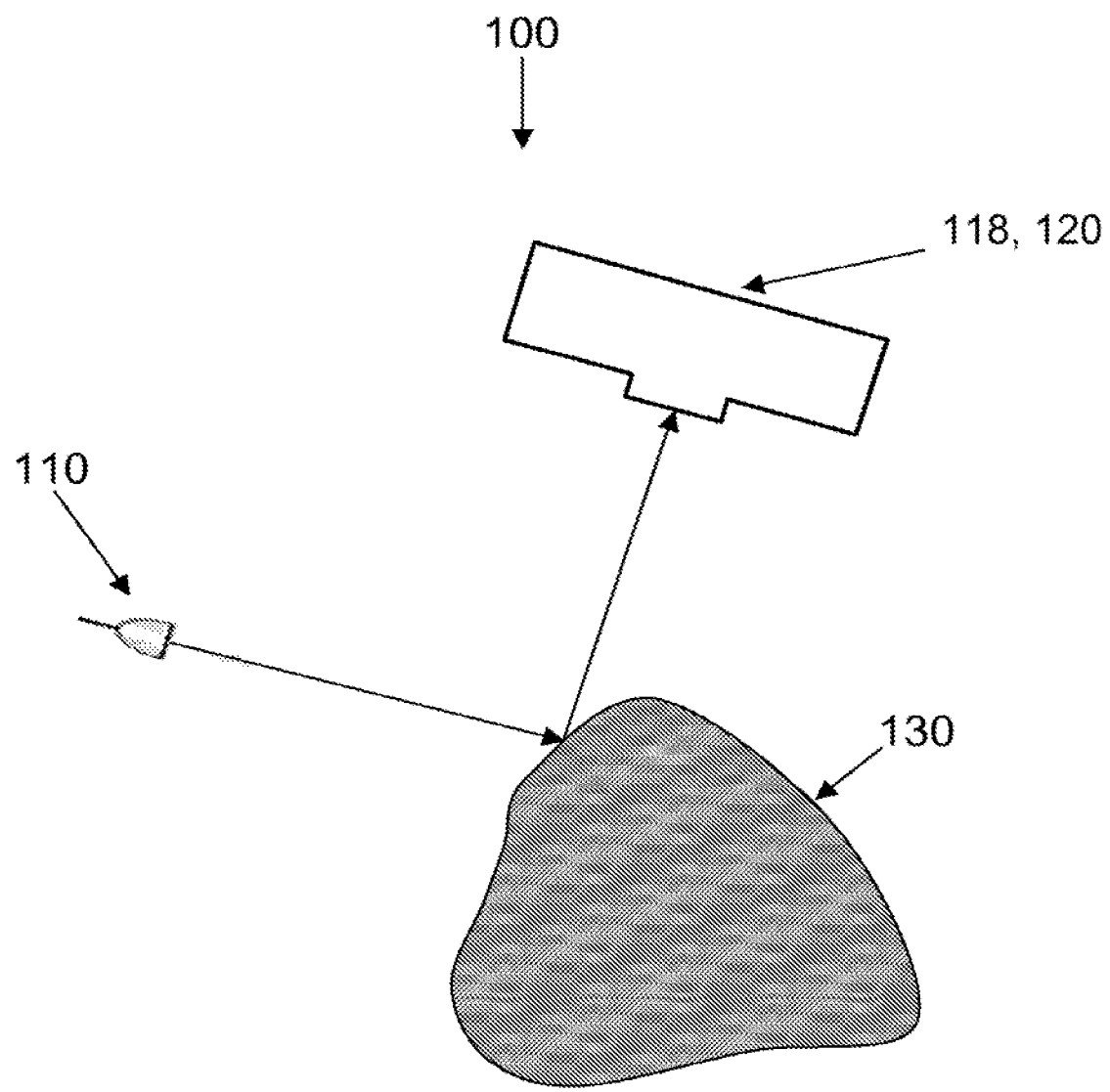
Figure 2:
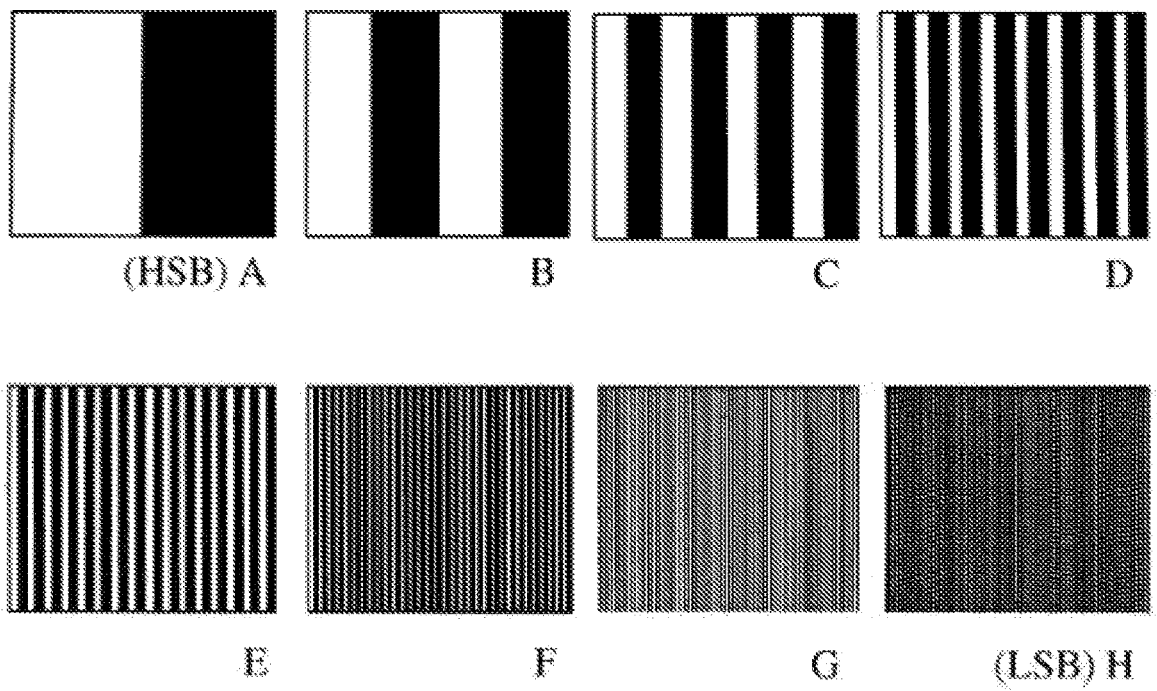
FIG. 2A-H illustrates binary coded patterns.
Figure 3:
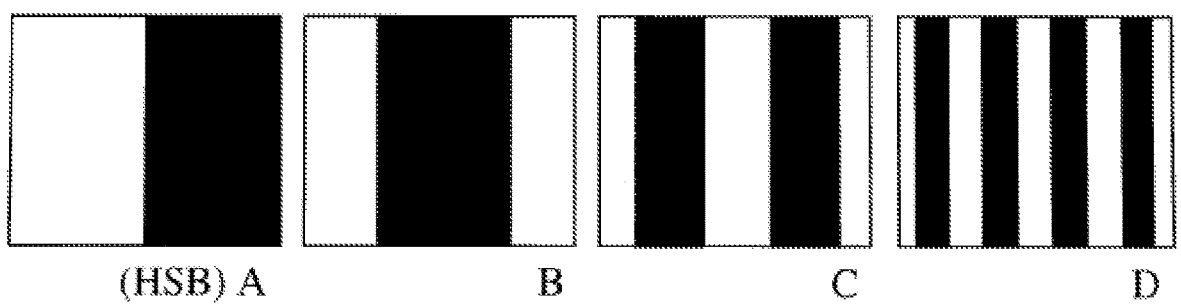
FIG. 3A-H illustrates Gray-coded patterns.
Figure 3:
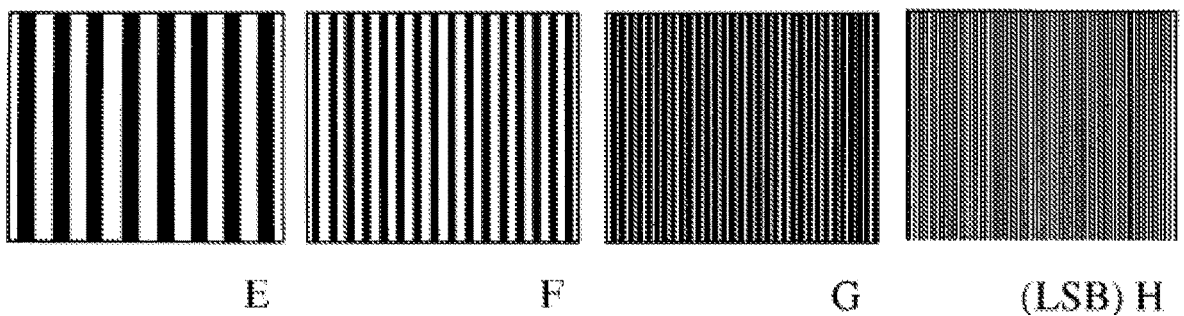

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing an enhanced 3D laparoscopic image adapted to be useful for gastroscopy and colonoscopy.

The term 'camera' hereinafter refers to an image-capture device, capable of creating a 2D image of an object. Examples of a camera include, but are not limited to, a CCD array and an electromagnetic system such as a TV camera.

The term 'endoscope' refers hereinafter to any means adapted for looking inside the body for medical reasons. This may be any instrument used to examine the interior of a hollow organ or cavity of the body. The endoscope may also refer to any kind of a laparascope. It should be noted that the following description may refer to an endoscope as a surgical tool.

The term 'endoscope distal end' hereinafter refers to the end of the endoscope that is inside the patient.

The term 'endoscope proximal end' hereinafter refers to the end of the camera outside the patient. The camera is attached to the endoscope's proximal end.

The term 'structured light' hereinafter refers to a method of producing 3D images using a single 2D camera. In the structured light method, the object is illuminated by a set of rays of light, each ray illuminating a spot on the object from a known position and a known direction, and each ray emitted at a known time. For each known time, a 2D camera image is created from light reflected from the spots created from rays existing at that time. Initially, a known calibration object is illuminated. From the known shape, size and position of the calibration object and from the locations in the camera images of the reflected light, mathematical matrices can be calculated. These matrices enable calculation of the 3D location of the surface of an unknown object, when the unknown object is illuminated by the same set of rays as illuminated the calibration object.

The term 'structured light pattern' hereinafter refers to the set of rays of light with a known spatial and temporal pattern used, as described above, to illuminate an object.

The term 'field of view' (FOV) hereinafter refers to the scene visible to the camera.

The terms 'about' and 'approximately' hereinafter refers to a range of ±20% of the value.

The term 'world' hereinafter refers to the region of space in which objects are located.

The term 'world coordinates' hereinafter refers to a coordinate system fixed in the world. The location in space of a physical object to be imaged will be described by the world coordinate system.

The term 'projector' hereinafter refers to the set of light rays used to illuminate an object.

The term 'projector coordinates' hereinafter refers to a coordinate system in which the projector is located and which describes the relation of the light rays to each other, both spatially and temporally.

The term 'camera coordinate system' hereinafter refers to a coordinate system fixed with respect to the camera.

The term 'stripe id' hereinafter refers to the temporal and spatial location and direction of a light ray.

The term 'articulation' refers hereinafter to any device which has more than 1 degree of freedom. Thus, said tool can bend either in the tip thereof or any location in the body of the same.

The term 'toggle' refers hereinafter to switching between one tagged surgical tool to another.

The term 'region of interest' refers hereinafter to any region within the body of a subject which may be of interest for the operator of the system of the present invention. The region of interest may be, for example, an organ to be operated on, a RESTRICTED area which a surgical instrument should avoid approaching, a surgical instrument or any other region within the human body or body of another living animal.

The term 'surgical environment' refers hereinafter to any anatomical part within the body of a subject which may be in the surroundings of a surgical instrument. The environment may comprise: organs, body parts, walls of organs, arteries, veins, nerves, a region of interest, or any other anatomical part of the human body.

The term 'spatial position' refers hereinafter to a predetermined spatial location and/or orientation of an object (e.g., the spatial location of the endoscope, the angular orientation of the endoscope, and any combination thereof).

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The terms 'tool', 'surgical tool' and 'surgical instrument' refer hereinafter to any instrument or device introducible into the human body. The term may refer to any portion of the tool. For example it can refer to the tip of the same, the body of the same and any combination thereof. It should be further pointed that the following description may refer to a surgical tool/instrument as an endoscope. Non-limiting examples of tools include a retractor, a clamp, a swab, a needle, an endoscope, and any other medical tool or instrument.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process that proceeds without the necessity of direct intervention or action on the part of a human being.

The term 'automated assistant' refers hereinafter to any mechanical device (including but not limited to a robotic device) that can maneuver and control the position of a surgical or endoscopic instrument, and that can in addition be adapted to receive commands from a remote source.

The term 'ALLOWED movement' refers hereinafter to any movement of a surgical tool which is permitted according to a predetermined set of rules.

The term 'RESTRICTED movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an ALLOWED movement of a surgical tool or the endoscope is a movement which maintains the surgical tool within the favored zone; and a RESTRICTED movement of a surgical tool is a movement which extracts (or moves) the surgical tool outside the favored zone. The term 'time step' refers hereinafter to the working time of the system. At each time step, the system receives data from sensors and commands from operators and processes the data and commands and executes actions. The time step size is the elapsed time between time steps.

The term 'proximity sensor' hereinafter refers to a sensor able to detect the presence of nearby objects without physical contact. Proximity sensors are sometimes referred to as 'force sensors'. A proximity sensor often emits an electromagnetic field or a beam of electromagnetic radiation (infrared, for instance), and looks for changes in the field or return signal. The object being sensed is often referred to as the proximity sensor's target. Different proximity sensor targets demand different sensors. For example, a capacitive photoelectric sensor might be suitable for a plastic target; an inductive proximity sensor always requires a metal target. Proximity sensors can be introduced into the body and used for detecting metal fragments during surgery. See, for example, Sakthivel, M., *A new inductive proximity sensor as a guiding tool for removing metal shrapnel during surgery*, Instrumentation and Measurement Technology Conference (I2MTC), 2013 IEEE International, pp. 53-57. ISSN: 1091-5281, print ISBN: 978-1-4673.

The terms 'degrees of freedom' (DOF) refer hereinafter to a set of independent displacements that specify completely the displaced position of the endoscope or laparoscope.

The term 'insertion point' refers hereinafter to the point where the endoscope enters the human body.

The terms 'joystick' and 'joystick unit' refer hereinafter to a motion and position sensitive device enabled to control the motion of another device, with the motion and position information including, but not limited to, the direction of motion (in 1, 2 or 3 dimensions) and the speed of the motion and the changes in direction and speed as a function of time. Joystick units may, for example, in a non-limiting manner, be shaped like a rod or lever; which is bent, twisted, depressed or slid, the direction of the bend, twist, depression or sliding relatable to the direction of motion and the magnitude thereof relatable to the speed of the motion. Joystick units can comprise a button which is depressed, slid or rocked, wherein the direction of the depression, sliding or rocking is related to the direction of motion and the magnitude thereof is related to the speed of the motion. They can comprise a surface along which a finger or fingers or a hand or an implement slides, wherein the direction of the motion on the surface is related to the direction of motion and the speed of the motion along the surface is related to the speed of motion of the controlled device.

All temperatures referred to herein are temperatures in degrees Celsius.

The following abbreviations are used throughout the disclosure:

DOF refers to degree(s) of freedom;

SFME refers to System For Maneuvering an Endoscope, a system for enabling an operator to maneuver the endoscope as disclosed hereinbelow.

Laparoscopic surgery, also called minimally invasive surgery (MIS), is a modern surgical technique in which operations in the abdomen are performed through small incisions (usually 0.5-1.5 cm) as compared to larger incisions needed in traditional surgical procedures. The key element in laparoscopic surgery is the use of a laparoscope, which is a device adapted for viewing the scene within the body, at the distal end of the laparoscope. Either an imaging device is placed at the end of the laparoscope, or a rod lens system or fiber optic bundle is used to direct this image to the proximal end of the laparoscope. Also attached is a light source to illuminate the operative field, inserted through a 5 mm or 10 mm cannula or trocar to view the operative field.

The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

In many cases, the laparoscope cannot view the entire working space within the body, so the laparoscope is repositioned to allow the surgeon to view regions of interest within the space. In some laparoscopic systems, this requires the surgeon to instruct an assistant to manually move the laparoscope. In other systems, the surgeon himself instructs the laparoscope to move, by a manual control system such as a button, joystick or slider attached to the surgeon or to a surgical tool, by contact with a touchscreen, or by voice commands.

In all such systems, in directing and maneuvering the surgical controlling system, the controller needs to avoid obstacles such as body organs and tools or other surgical equipment in the body cavity. Its speed should be controlled so that, on the one hand, the speed is low enough to make avoidance routine and to ensure that the instrument accurately reaches the desired location and, on the other hand, the speed needs to be great enough that maneuvers are accomplished in a reasonable time.

In order to avoid the obstacles, in a conventional system, the endoscope must be routed around them, increasing the complexity of maneuvering and the time taken for maneuvering.

In the present, system, the system comprises at least one articulating section, typically an articulating tool such as an articulating endoscope. The articulating tool can have an articulating tip, where the articulations are near the tip, it can have an articulating body, where the articulations are in the body or shaft of the tool, or both. The articulations allow bending in at least two degrees of freedom (DOF), preferably in four DOF, and possibly in all six DOF (bending in all three directions and rotating in all three directions).

In comparison to a rigid tool, during maneuvering, an articulating tool can use more direct routes, as the articulating section enables removal of the tip of an articulating tool from the region of an obstacle. For example, instead of routing an endoscope around a body organ, the endoscope can articulate such that its tip is withdrawn to a sufficient height that the route of the endoscope can be directly across the organ.

Furthermore, the system has more flexibility in positioning. For example, the angle of the field of view can be changed by changing the articulation of the endoscope, with only minimal change of the position of the main part of the endoscope.

A device of the present invention, with an articulating endoscope and providing a 3D image, is useful for colonoscopy or gastroscopy, treatments where the endoscope moves within a relatively restricted, non-straight space. By traversing the interior of a portion of the alimentary canal, abnormalities such as, but not limited to, polyps or ulcers can be identified and a warning provided to a user of the system and to the patient. In preferred embodiments, the system additionally comprises recognition software that can identify abnormalities and can label the abnormality in real time on an image of the field of view. The label can be by any means known in the art such as, but not limited to, text, a colored patch, a textured patch, an arrow or other marker, and any combination thereof.

Because of the flexibility provided by the articulating endoscope and because of the increased locatability possible with a 3D image, the device of the present invention, compared to the prior art, can more easily follow the contours of body organs and can more effectively view the sides and backs of organs. It can therefore find cysts, lumps or other abnormal masses in the abdominal cavity more effectively than the prior art. It can also efficiently map the interior of the abdominal cavity and can be used for cartography of the intestines, including the bowels and colon.

In many cases, the surgeon wants a close-up view of his working area; in other cases an overview is desirable, and a rapid transition from close-up to overview and vice-versa can also be desirable.

The device disclosed herein uses a standard laparoscopic camera and a computer-controllable laparoscopic light source in conjunction with software using the structured light method in order to provide a laparoscopic system which presents the user with 3D images from a single camera.

A high resolution camera can provide sufficient detail to create a detailed 3D image.

In some embodiments, a wide-angle lens such as, but not limited to, a fish-eye lens, an omnidirectional lens and any combination thereof provides an image of a large portion, if not all, of the working area, such as the interior of the abdomen. The image provided by a wide-angle lens is frequently distorted; in preferred embodiments of systems with a wide-angle lens, software is used to correct the distortion.

The advantages of a 3D image include:
It increases the accuracy and reliability of tool detection and tracking from the laparoscope image, thereby minimizing or eliminating the need for auxiliary equipment for the purpose.
It increases the accuracy of navigation within the body cavity, thereby minimizing the risk of inadvertent tissue damage.
It provides a three-dimensional display for the surgeon, thereby increasing the accuracy with which he can work.

There are many methods of providing a 3D image. These include, but are not limited to:
Use of two cameras to provide a stereo image. This has the disadvantage that two separated sets of camera lenses are needed, and therefore a laparoscope adapted to accept two separated camera lenses.
Use of the motion of the camera to get more than one view of the scene, each view from a different perspective, and then combining the views via internal algorithms. This has the disadvantage of requiring motion of the camera.
Use of the Structured Light technique. This requires calibration of the system before use, and can be sensitive to spurious pixels in the image, but has the advantage of requiring neither camera motion nor a special laparoscope.

For the laparoscope disclosed herein, structured light is the preferred method of providing a 3D image.

Advantages of a structured light system include:
The accuracy of the three-dimensional reconstruction is very high.
Recovery from bit errors is possible.
It is possible to provide 3D images of bodies of uniform shade, which is not possible in a stereo system using two cameras.
Adding a Distance Index from one object to the other (e.g., tissue).
Measurement of distances between any two points in the image is simple, since the distance is a geodesic distance over the surface or the Euclidean distance.
It is possible to embed texture in the image, improving the ease of identification of tissues.
It is possible to use a standard camera and a standard laparoscope, lighting the object via a standard laparoscope lighting system.

In the structured light technique, schematically illustrated (100) in FIG. 1, a controlled light pattern or a series of controlled light patterns is emitted by a light source (110) and the 3D image is constructed from the light pattern received by a sensor (118) of a camera (120) after reflection from an object (130) or objects illuminated by the light and in the field of view of the sensor.

In the simplest structured light camera, a "projector", a source of light, projects a spot of light, for example, a laser beam, onto an object. The location of the projector and the direction of projection are known. The location on the camera image of the reflected spot can be easily located and identified. Since the point location on both the projector and the camera is known, reconstruction of the coordinates in space of the reflecting point on the object (the "shape world coordinates") can be carried out by simple triangulation.

A more efficient scheme replaces the point laser beam by a line beam that "sweeps" the object. Still, sweeping the entire scene by a laser beam is a time consuming operation and therefore is limited to static objects.

For a better scan time, several stripe illumination-based techniques have been proposed. Single pattern approaches, using spatial encoding of projection planes or rays can be used. Although time-efficient, spatial encoding generally produces a sparse depth map with mediocre spatial resolution.

High reliability identification of projection planes with non-restrictive assumptions on scene contents and illumination conditions can be achieved by temporal encoding, which is based on projection of a sequence of light patterns ("stripes") onto the object. A robust, commonly used structured light system based on binary light patterns encoded with Gray code is used in preferred embodiments of the device disclosed herein. Color modulation, which allows a reduction in the number of stripes projected onto the object, is also possible, with a color camera. Color modulation, as discussed hereinbelow, can also be used be used in addition to spatial and temporal encoding in order to determine the nature of the tissues being imaged, FIG. 2A-H shows binary coded patterns, while FIG. 3A-H shows Gray-coded patterns. In both figures, 'HSB' is the highest significant bit, and 'LSB' is the least significant bit. The patterns differ in that, in the Gray-coded patterns, the edge-most light stripe is split, appearing at both edges, so that the pattern is symmetrical about its center. Having a (half) light stripe at each edge improves the robustness of the system.

An important issue in structured light systems is calibration. Reconstruction is possible only when the camera projection matrix and the projection planes are known in the world coordinate system. Calibration of structured light scanners is usually more complicated than that of a passive stereo pair. A standard approach consists of three steps: estimating the camera intrinsic matrix (camera calibration), estimating the plane equations for each of the projection planes (projector calibration) and finally, estimating the Euclidean transformation between the camera and the projector (projector-camera calibration).

Figure 4:
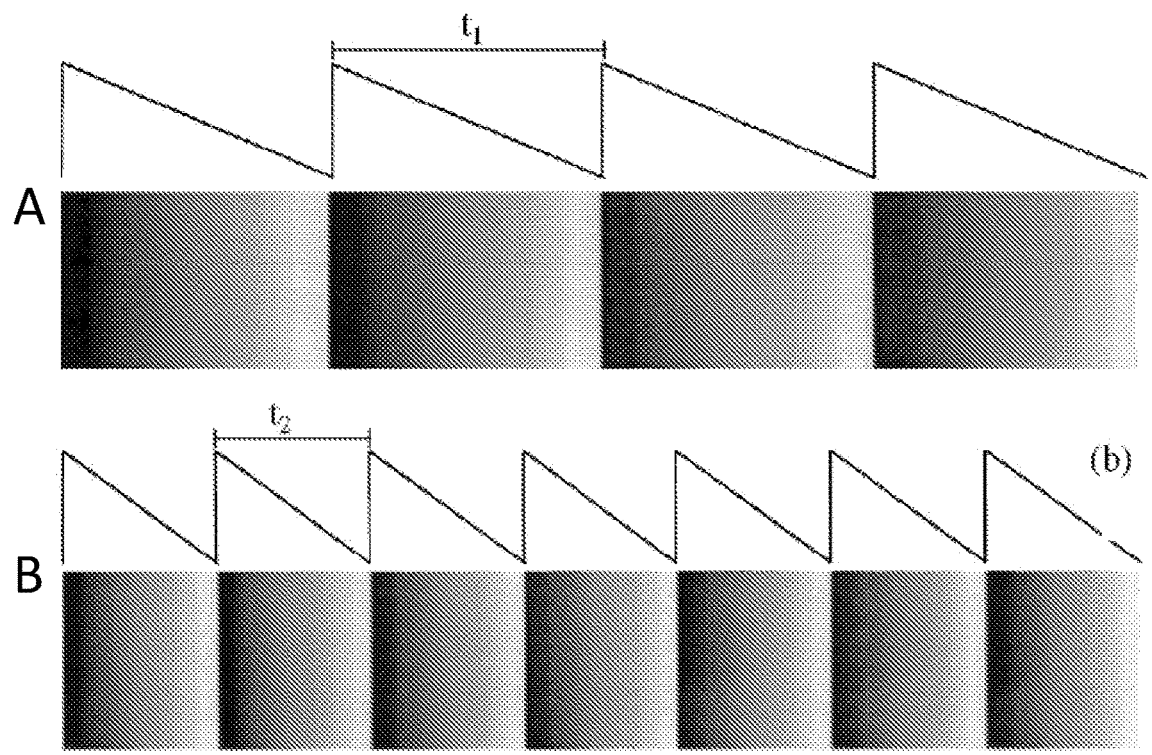
FIG. 4 shows a stripe pattern of varying intensity.

Other examples of structured light systems use stripes that vary in intensity across the stripe, with each stripe being black at one edge and white at the other. In embodiments with varying intensity, the intensity changes in time as the plane of light is swept across the working space which includes the object. FIG. 4A-B shows the intensity of the light as a function of time t, with $t_1$ the period of the stripe pattern of FIG. 4A and $t_2$ the period of the stripe pattern of FIG. 4B.

Example 1

An alternative approach, however, provides the preferred embodiment for the present invention. This alternative approach is based on estimation of the world to camera image and world-to-projector coordinate system transformation, extended to simultaneously estimating a backprojection operator, an operator that enables determination of the location in space of the surface of an object, from the locations on camera images of spots of light reflected from the object, where the spots of light are generated by rays emitted from known positions, in known directions and at known times.

The following sections describe a method of determining the backprojection operator. In the method described hereinbelow, a calibration object of known shape and size (the world object) is illuminated by a set of rays of light (the projector, in the projector coordinate system) emitted from known positions, in known directions and at known times. These rays are reflected from the calibration object (the object, in the world coordinate system) and generate at least one 2D camera image (the camera image, in the camera coordinate system). From the known ray positions, the known spot positions on the camera images and the known shape and size of the calibration object, operators are determined that enable determination of the 3D position in space of an unknown object.

In the derivation hereinbelow, the model will be described, then a method of generating a 3D image of an object (reconstruction of the object) from the camera images and the stability of the reconstruction will be described. This is followed by a method of generating the reconstruction operators from a calibration object, and an implementation of an embodiment of the method.

Model of a Structured Light System

A typical structured light system consists of a camera and a projector. The role of the projector is to light the scanned object in such a way that, from the image (or sequence of images) acquired by the camera, a stripe code can be extracted. The encoding can be done either spatially using a single pattern or temporally using a series of varying patterns. The raw output of a structured light scanner is a stripe code assigned for every pixel in the image. Intersection of a ray in world coordinate system (WCS) with a plane in WCS yields the world coordinates of an object point. Using this triangulation method, the raw sensor data is converted into 3D data in the WCS.

For simplicity, in the derivations below, it will be assumed that both the camera and the projector obey the pin-hole optical model (non-linear distortion correction can be applied for lenses that do not obey this model). The transformation from 3D world coordinates to camera image plane coordinates will be described by a 3×4 perspective projection matrix (PPM).

The projector will be modeled by a 2×4 PPM, mapping world coordinates to stripe identification code (id).

Three coordinate systems are defined: a homogenous world coordinate system $X_w$ in which the object's position is specified; a homogenous camera coordinate system $X_c$, in which pixel locations in the image plane are specified, and a homogenous projector coordinate system $X_p$, in which stripe ids are specified. The latter is particular, since it contains only one independent coordinate.

The transformation from world coordinates to camera coordinates is given by $$X_c = C_c X_w, \quad (1)$$

where $C_c$ is the camera PPM and is of the form $$C_c = \alpha \begin{bmatrix} f_x & kf_y & x_c^0 \\ 0 & f_y & y_c^0 \\ 0 & 0 & 1 \end{bmatrix} [R_c \; t_c]. \quad (2)$$

The rotation matrix $R_c$ and the translation vector $t_c$ define the transformation between WCS $X_w$, and the camera-centric reference frame $X_c$. The parameters $f_x$ and $f_y$ are the camera focal length scaled to each of the CCD dimensions, and $x_c^0$ and $y_c^0$ are the origin of $X_c$ in image coordinates. The parameter $\alpha$ is a proportion coefficient and k is the shear of the camera coordinate system.

Similarly, the transformation form world coordinates to projector coordinates is given by $$X_p = C_p X_w, \quad (3)$$

where $C_p$ is the projector PPM of the form $$C_p = \alpha \begin{bmatrix} f_p & 0 & x_p^0 \\ 0 & 0 & 1 \end{bmatrix} [R_p \quad t_p] \quad (4)$$

$R_p$ and $t_p$ define the transformation between WCS and $X_p$. The parameter $f_p$ is the projector focal length scaled to the projector's dimensions, and $x_c^0$ is the origin of $X_p$ in projector coordinates, which physically is the x-coordinate of the intersection of the optical axis and the projector.

Here we implicitly assume that the stripe code varies along the horizontal direction of the projector. McIvor and Valkenburg [A. M. McIvor, R. J. Valkenburg, I Robert, J. Valkenburg, J. Valkenburg, *Calibrating a structured light system*, Image & Vision Computing, New Zealand, 1995] show that $C_p$ is a valid camera PPM if and only if the submatrix formed by its first three columns has full rank. Similarly, $P_p$ is a valid projector PPM if and only if the submatrix formed by its first three columns is of rank 2.

Equations 1 and 3 define the transformation $$T: X_w \to (X_c, X_p), \quad (5)$$

which maps an object point in WCS into pixel location in the camera image plane and a stripe id (coordinate in the projector system of coordinates). We refer to this transformation as forward projection.

The world coordinates of the object point are usually unknown and have to be determined, whereas the pair $(x_c, x_p)$ is what the structured light sensor measures and can be extracted from the raw data. Therefore, given the camera and the projector PPMs and a pair of measurements $(x_c, x_p)$, one can attempt inverting eq. (5) in order to calculate $x_w$. We will term the inverse transformation $$T^{-1}: (X_c, X_p) \to X_w, \quad (6)$$

as backprojection and the process of determining world coordinates from measured data as reconstruction.

Reconstruction requires the knowledge of $C_c$ and $C_p$. Therefore, calibration must be performed before, during which the forward projection operator is estimated. This is done by measuring a set of pairs $\{((x_c x_p)_n\}_{n=1}^N$ corresponding to a set of points with known world coordinates $\{(X_w)_n\}_{n=1}^N$. Physically, a calibration object with a set of fiducial points, whose location is known, is scanned. WCS is then chosen to be some local coordinate system of the calibration object, in which the coordinates of each fiducial point are specified.

Reconstruction

In this section we assume that the forward projection operator T is known (i.e. the projective matrices $C_c$ and $C_p$ are given). The reconstruction problem can be stated as follows: given measured $(x_c, x_p)$, calculate $x_w$ according to $$x_w = T^{-1}(x_c, x_p). \quad (7)$$

Explicitly, $x_w$, has to satisfy the linear system of equations $$x_c = C_c x_w \quad (8)$$

$$x_p = C_p x_w. \quad (9)$$

However, since all vectors are given in homogeneous coordinates, it is possible that no $x_w$, satisfies eqs. (8) and (9) simultaneously. Let us denote $x_c = [w_c x_c, w_c y_c, w_c]^T$ and $x_p = [w_p x_p, w_p]^T$ and let ck, pk be the k-th row of $C_c$ and $C_p$, respectively. Then, the linear system of equations can be rewritten as $$w_c x_c = c_1 x_w$$

$$w_c y_c = c_2 x_w$$

$$w_c = c_3 x_w \quad (10)$$

and $$w_p x_p = p_1 x_w$$

$$w_p = p_2 x_w. \quad (11)$$

Substituting $w_c$ into eq. (10) and wp into eq. (11) yields $$x_c c_3 x_w = c_1 x_w$$

$$y_c c_3 x_w = c_2 x_w$$

$$x_p p_2 x_w = p_1 x_w, \quad (12)$$

which can be written in matrix notation as $Qx_w = 0$, where $$Q = \begin{bmatrix} x_c c_3 - c_1 \\ y_c c_3 - c_2 \\ x_p p_2 - p_1 \end{bmatrix} \quad (13)$$

The matrix Q can be split into a 3×3 matrix R and a 3×1 vectors: $Q = [R, s]$. Substituting $x_w = [w_w x_w, w_w y_w, w_w z_w, w_w]^T$ yields $$[R, s] \begin{bmatrix} w_w x_w \\ w_w x_y \\ w_w z_w \\ w_w \end{bmatrix} = R \begin{bmatrix} w_w x_w \\ w_w x_y \\ w_w z_w \end{bmatrix} + w_w s = 0. \quad (14)$$

Therefore, the object point in non-homogenous world coordinates $x_w = [x_w, y_w, z_w]^T$ is a solution of the linear system $$Rx_w = -s. \quad (15)$$

Backprojection is therefore given by $$x_w = -R^{-1} s. \quad (16)$$

It must be remembered that both R and s are functions of $x_c$, $y_c$ and $x_p$.

If $C_c$ and $C_p$ are valid camera and projector PPMs, R is invertible except of cases where the ray originating from the camera focal point to the object point is parallel to the plane originating at the projector focal point and passing through the object point. The latter case is possible either when the object point is located at infinity, or when the camera and the projector optical axes are parallel (this happens when $R_c = R_n$). This gives a constraint on camera and projector mutual location: in order to make triangulation possible, the camera should not have its optical axis parallel to that of the projector.

Reconstruction Stability

As discussed hereinabove, the matrix R in Eq. (15) becomes singular when the ray in the camera coordinate system and the plane in the projector coordinates system are parallel. A reasonable question that may arise is how stable is the solution under random perturbations of $x_c$ and $x_p$. In this work, we will address only perturbations in $x_p$, since they are the most problematic ones in structured light systems.

For simplicity, let us assume that WCS coincides with the camera coordinate system and the transformation to the projector coordinate system is given by $$x_p = R_p + t_p. \quad (17)$$

Without loss of generality, it can be assumed that the centers of the camera coordinate system and the projector coordinate system coincide with their optical axes, i.e. $x_c^0 = y_c^0 = x_p^0 = 0$.

Without loss of generality, it can be assumed that the object point is found on some ray in $x_c = \alpha r_c$; the ray is uniquely defined by the camera image plane coordinates $x_c$ and the point location is uniquely defined by the parameter $\alpha$. The stripe id corresponding to the given object point can be denoted by $x_p$. Then, the following system of linear equations $$n^T x_p = 0$$
$$n^T (R_p x_c + t_p) = 0, \quad (18)$$

must hold simultaneously; n denotes the normal to the plane defined by the stripe id $x_p$. Substituting $x_c = \alpha v_c$ yields $$n^T x_p = n^T(\alpha R_p v_c + t_p), \quad (19)$$

hence $$\alpha = \frac{n^T x_p}{n^T R_p v_c} \quad (20)$$

However, in practice, the stripe id $x_p$ is estimated using structured light, and therefore it is especially sensitive to noise. Let us assume that instead of the real stripe id $x_p$, a perturbed stripe id $\tilde{x}_p = x_p + \delta x_p$ was measured. This, in turn, means that $\tilde{x}_p = x_p + [(\delta X_p, 0, f_p]^T$, which yields $$\tilde{\alpha} = \frac{n^T \tilde{x}_p}{n^T R_p v_c}. \quad (21)$$

Hence, the perturbation in $x_p$ causes a perturbation in the location of the object point along the ray $x_c = \alpha v_c$ by $$\delta \alpha = \frac{n_1 \delta x_p}{\|n\|_2 \|v\|_2 \sin\Theta_{nv}}, \quad (22)$$

where $\Theta_{nv}$ is the angle between the plane defined by the normal n and the ray defined by the direction $v_c$. Therefore, $$\delta \|x_w\|_k = |\delta \alpha| \|v_c\|_k = \left|\frac{n_1}{\|n\|_2 \sin\Theta_{nv}}\right| |\delta x_p|. \quad (23)$$

The ratio $$\cos\theta_p = \frac{n_1}{\|n\|_2}$$

has a geometrical interpretation of cosine of the projection angle; substituting it into Eq. (23) yields the sensitivity of the reconstructed object point to perturbations in the stripe id:

$$\frac{\delta \|x_w\|_k}{|\delta x_p|} = \left|\frac{\cos\theta_p}{\sin\Theta_{nv}}\right|. \quad (24)$$

Calibration

In this section we assume that the forward projection operator T is unknown and has to be estimated from a given set of measured $\{(x_c, x_p)_n\}_{n=1}^N$ and corresponding known $\{x_w\}_{n=1}^N$. Explicitly, it is desired to find such $C_c$ and $C_p$ that obey $$(x_c)_k = C_c(x_w)_k \quad (25)$$

$$(x_p)_k = C_p(x_w)_k, \quad (26)$$

for $k = 1, \ldots, N$. Since data measurement is not perfect (e.g., both the camera and the projector resolution is finite), no projection operator will fit the data perfectly. Therefore, it is necessary to find such a $T^{-1}$ that will relate the measured and the known data in an optimal way. It is thus important to address the optimality criterion.

McIvor and Valkenburg (see above) study the possibility of optimizing separately the camera and the projector forward projections in the sense of the $L_2$ norm. Mathematically, this can be formulated as $$C_c = \operatorname{argmin} \sum_{k=1}^N \|C_c(x_w)_k - (x_c)_k\|_2^2 \text{ s.t. } C_c \in PPM \quad (27)$$

$$C_p = \operatorname{argmin} \sum_{k=1}^N \|C_p(x_w)_k - (x_p)_k\|_2^2 \text{ s.t. } C_p \in PPM.$$

Let us define $$B_k = \begin{bmatrix} (x_w)_k & 0 \\ 0 & (x_w)_k \\ -(x_c)_k (x_w)_k & -(y_c)_k (x_w)_k \end{bmatrix}^T \quad (28)$$

$$l = [c_1, c_2, c_3]^T,$$

where $c_k$ is the k-th row of $C_c$. Using this notation, the set of N equations (25) can be rewritten as $$B_k l = 0, \quad (29)$$

for $k = 1, \ldots, N$, which in turn can be expressed as a single homogenous linear equation $$Al = 0, \quad (30)$$

Where $A = [B_1^T, \ldots B_N^T]^T$. The vector of variables l is the camera projection matrix $C_c$ needed to be determined. Since the camera PPM is defined up to a scaling factor, we will demand $\|l\|_2 = 1$ in order to avoid the trivial solution. With physically measured data, the matrix A will usually have full rank and therefore, no l will be an exact solution of eq. (30). However, one can find the best least-squares solution by solving $$l = \operatorname{argmin} \|Al\|_2^2 \text{ s.t.} \|l\|_2 = 1 \quad (31)$$

and ensuring that the obtained $C_c$ is a valid PPM. Solving eq. (31) is equivalent to solving eq. (27) for the camera matrix, and its solution minimizes the square error between the measured image plane coordinates of the set of fiducial points and those obtained by projecting the set of the corresponding points in WCS onto the camera image plane.

Similarly, replacing $B_k$ and $l$ in eq. (28) with $$A = [B_1^T, \ldots, B_N^T]^T \quad B_k = \begin{bmatrix} (x_w)_k \\ -(x_p)_k (x_w)_k \end{bmatrix}^T \quad (32)$$

$$l = [p_1, p_2]^T$$

yields the $L_2$ minimization problem, eq. (27), for the projector matrix.

The optimization problem of eq. (31) is a minimum eigenvalue problem and it can be shown that $l$ minimizing $\|Al\|_2$ is the eigenvector corresponding to the minimum eigenvalue of $A^TA$. It must be noted, however, that since usually the minimum eigenvalue of $A^TA$ is very small, numerical inaccuracies are liable to rise.

Solution to the problem 27 finds two PPMs that minimize the squared error between the measured data and the forward projection of the known fiducial points in WCS into the camera and the plane coordinate systems. However, what is actually needed is to minimize the squared error between the known fiducial points in WCS and the backward-projected measurements. Mathematically, this can be formulated as $$T = \operatorname*{argmin} \sum_{k=1}^{N} \|T^{-1}(x_c, x_p)_k - (x_w)_k\|_2^2 \quad (33)$$

$$\text{s.t. } C_c, C_p \in \text{textPPM}.$$

The above problem is no more separable and is non-convex; therefore, it has to be solved by numerical global optimization methods. Still, an efficient solution in a few iterations is possible using the Newton method, since the number of variables in the problem is small (3×4+2×4=20) and both the cost function, its gradient, and the Hessian can be computed analytically. As the starting point for iterative optimization, a solution of eq. (27) can be used.

Since the calibration process is performed only once, additional computational complexity can be used in order to obtain better projection estimation and better reconstruction results.

Figure 5:
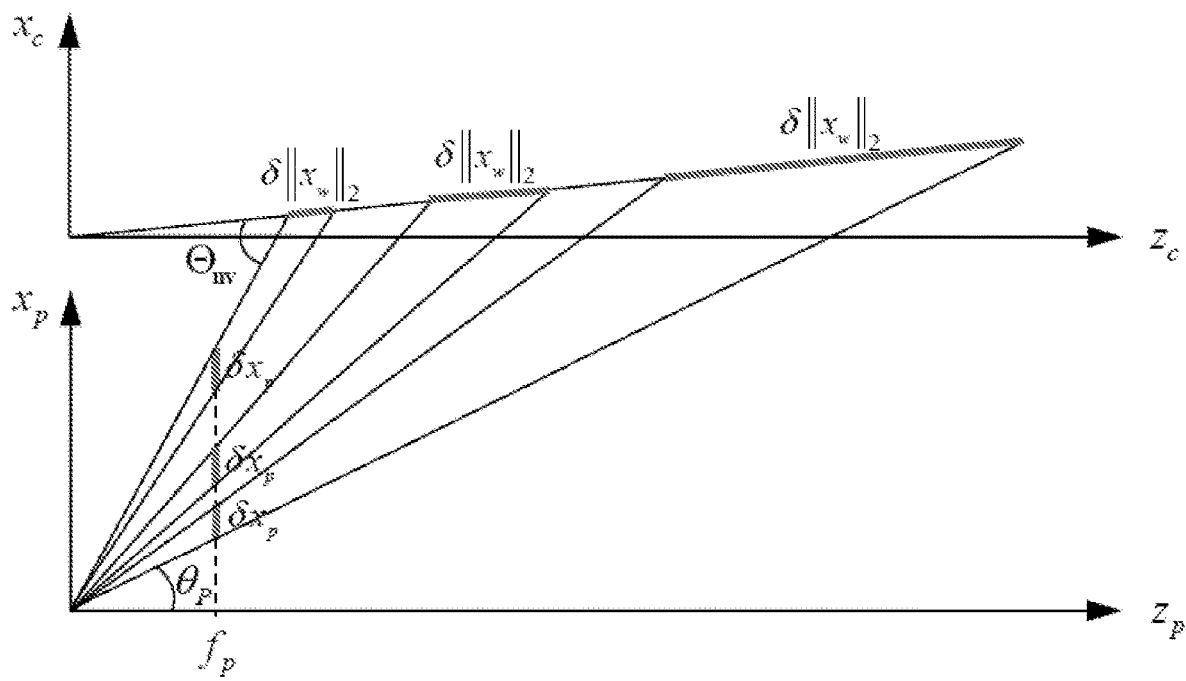
FIG. 5 shows the sensitivity of the reconstructed object point to perturbations for an embodiment of the system for an embodiment of the system.

FIG. 5 shows the sensitivity of the reconstructed object point to perturbations in $x_p$; the smaller the angle $\theta_p$, the larger the error $\delta\|x_w\|_2$.

Implementation of Reconstruction

In our implementation, we used temporal encoding, which allowed to obtain a dense z-map of the scanned objects. Eight binary patterns, encoding the stripe id using the Gray code were projected onto the object and 8 corresponding images $I_k$ were acquired ($I_I$ corresponding to the most significant bit). In addition, we acquired a full-darkness image $I_L$ (the projector's LCD was blackened) and a full-illumination image $I_H$ (the projector's LCD was set to maximum intensity). These two images served for compensation of ambient light and the non-constant albedo of the object.

The quantity $I_L(x, y)$ reflects the illumination of the object in pixel $(x, y)$ at darkness and differs from zero only due to presence of ambient illumination. Since the reflectance of objects at illumination levels used in normal conditions obeys linear superposition law, subtracting IL from the rest of the images compensates for the ambience light. The quantity $I_H(x, y) - I_L(x, y)$ is proportional to the object albedo at the pixel $(x, y)$.

We define a set of 8 normalized intensity images $$J_k(x, y) = \frac{I_k(x, y) - I_L(x, y)}{I_H(x, y) - I_L(x, y)}. \quad (34)$$

A normalized intensity image $J_k(x, y)$ has the values in the range [0, 1] and reflects the amount of light irradiated onto the object surface at pixel $(x, y)$. The value of 1 stands for full illumination, whereas the value of 0 stands for no illumination. Theoretically, $J_k$ should be binary images: 1 where a light stripe is present and 0 in places where there is a dark stripe. In practice, however, $J_k$ are not binary and we therefore define $$B_k(x, y) = \begin{cases} 1 : J_k(x, y) > 0.5 \\ 0 : J_k(x, y) \leq 0.5 \end{cases}. \quad (35)$$

Better results were obtained when $J_k(x, y)$ was smoothed with a Gaussian filter prior to binarization. FIG. 6A-D depicts $I_H$ (FIG. 6A) and $I_L$ (FIG. 6B) as well as the LSB (FIG. 6D) pattern and the MSB (FIG. 6C) pattern.

FIG. 7A-E presents the normalized intensity image $J_3(x, y)$, the corresponding binary image $B_3(x, y)$ and a profile of a vertical line from these two images. FIG. 7A shows the raw image corresponding to one embodiment of a stripe pattern, FIG. 7B shows the normalized intensity image for that stripe pattern, FIG. 7C shows the binary image for that stripe pattern and FIG. 7D shows the fidelity image for that stripe pattern. All images are normalized. FIG. 7E shows the profile of a vertical line from the normalized intensity image (FIG. 7B) (dashed line) and the binary image (solid vertical lines).

For every pixel $(x, y)$, we define the stripe code as the Gray code sequence $$S(x,y) = [B_1(x,y), \ldots, B_8(x,y)]. \quad (36)$$

Decoding $S(x, y)$ yields a number $T(x, y) \in [0, 1]$, which will be referred to as stripe id. Note that $T(x, y)$ is not really continuous but rather has the values $T(x, y) \in \{2^{-N} n : n = 0, \ldots, 2^N - 1\}$ (in the example, N=8).

For every pixel, $x_p(x, y) = T(x, y)$ defines the projector coordinate of an unknown object point corresponding to the pixel $(x, y)$, transformed by the projector PPM. Similarly, the pixel indices $(x, y)$ define the camera image plane coordinates $x_c = x$, $y_c = y$ of the object point projected onto the camera coordinate system. Given the camera and the projector PPMs, world coordinates of the object point can be calculated according to eq. (21).

Pixel Fidelity Estimation

It is obvious that although both $J_k(x, y) = 0.95$ and $J_k(x, y) = 0.55$ will be binarized as $Bk(x, y) = 1$, they should definitely be treated differently. In the first case, one may say that the pixel $(x, y)$ in image k is indeed illuminated with high probability, whereas in the second case the probability of that pixel to be non-illuminated is almost equal to the probability of it being illuminated.

In order to give a quantitative measure of the pixel fidelity, let us assume that the measured normalized intensity image $J_k(x, y)$ is obtained from some ideal binary image $B_k^0(x,y)$ contaminated by zero-mean Gaussian noise $\xi(x, y)$ with variance $\sigma^2$. In case $J_k(x, y) > 0.5$, the pixel fidelity can be defined as $$F_k(x, y) = P\{J_k(x, y) + \xi(x, y) > 0.5\} = \Phi\left(\frac{0.5 - J_k(x, y)}{\sigma}\right),$$

where Φ denotes the c.d.f. of the normal distribution. The lower value of $F_k$ is 0.5 and it is obtained when $J_k(x, y)=0.5$. Similarly, for $J_k(x, y)<0.5$, the fidelity is $$F_k(x, y) = P\{J_k(x, y) + \xi(x, y) < 0.5\}$$
$$= 1 - \Phi\left(\frac{0.5 - J_k(x, y)}{\sigma}\right) = \Phi\left(\frac{J_k(x, y) - 0.5}{\sigma}\right).$$

Figure 8:
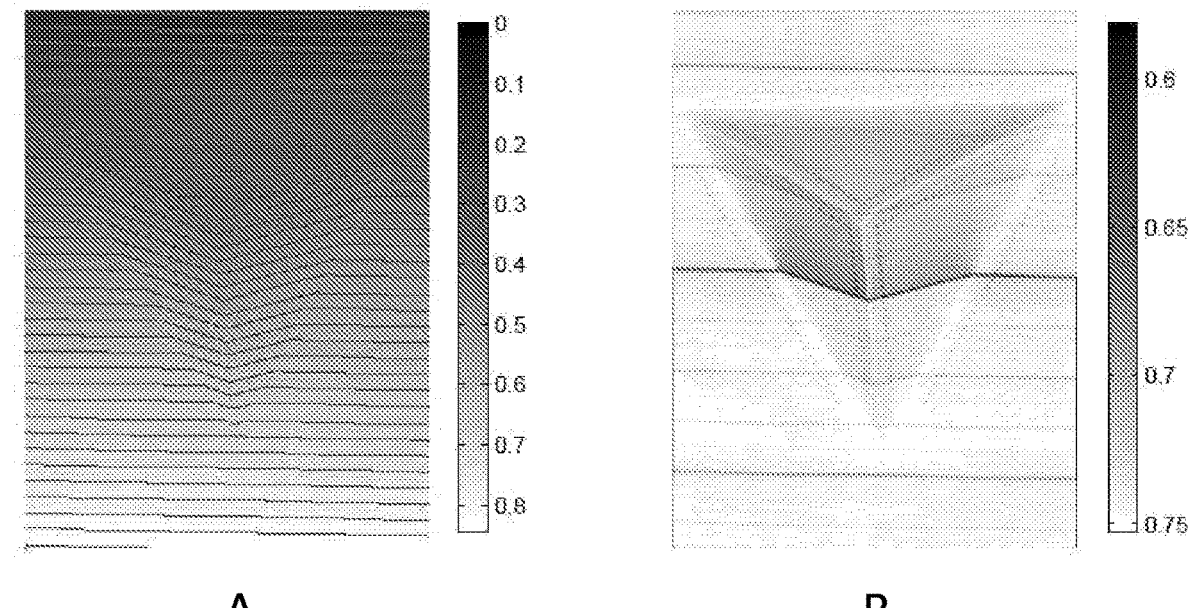
FIG. 8A-B shows the decoded stripe code T of a scanned object and the fidelity image F for an embodiment of the system.

Binarization errors in images corresponding to the most significant bit of the stripe code affect more the resulting stripe id T than errors in the least significant bit. Therefore, pixel fidelity in each stripe should be weighted by the stripe significance. We define the pixel fidelity as the weighted sum of the pixel fidelities in all stripes $$F(x, y) = \sum_{k=1}^{N} w_k F_k(x, y) = \sum_{k=1}^{N} w_k \Phi\left(\left|\frac{0.5 - J_k(x, y)}{\sigma}\right|\right),$$

where $w_k=2^{-k}$ is the significance of stripe k, and N is 8 in our implementation. The variance $\sigma^2$ was set empirically to 1. FIG. 8A-B shows the decoded stripe code T (FIG. 8A) of a scanned object and the fidelity image F (FIG. 8B).

Pixel fidelity can also provide important information and can be used, for example, for weighted mesh smoothing or decimation. For example, the pixel fidelity map can be used to obtain sub-stripe resolution, as shown below.

Sub-Stripe Resolution

One of important concerns in structured light systems is sub-stripe resolution. The stripe code T, which usually has granular nature due to quantization can be approximated by a continuous smooth surface, taking into account the fidelity map. We used a separable cubic spline, which was fitted to the image T with weighting inverse proportional to pixel fidelity. As the result, a smooth stripe id image $\tilde{T}$ with sub-stripe resolution was obtained.

Let us denote by Bv and Bu the orthonormal spline bases corresponding to the rows and the columns of T, respectively. Decomposition of the T in the two-dimensional separable basis obtained as the tensor product of By and Bu can be expressed as $$C=B_u^T B_c,\qquad(37)$$

or, alternatively, as $$c=B^T t,\qquad(38)$$

where t is the column-stack representation of T, c is a vector of spline coefficients and $B=B_c \otimes B_u$ is the Kronecker product of the row and the column bases. Weighted spline fitting constitutes to finding such spline coefficients c that minimize $$\sum_k \frac{1}{f_k}((Bc)_k - t_k)^2,\qquad(39)$$

where $f_k$ denotes the fidelity of the pixel $t_k$. We also add a controllable penalty on irregularity of the smoothed image $\tilde{t}=Bc$. In matrix notation, the weighted spline fitting problem reads $$c=\text{argmin}\{\|WBc-Wt\|_2^2+\lambda\|DBc\|_2^2\},\qquad(40)$$

where $$W = \text{diag}\left\{\frac{1}{f_k}\right\}$$

is the weighting matrix, D is the matrix defining the irregularity penalty and λ is the smoothness parameter, controlling the tradeoff between smoothness of $\tilde{t}$ and faith to the original data.

The analytic solution for eq. (40) is $$c=[B^T B+\lambda(DB)^T(DB)]^\dagger t,\qquad(41)$$

where $A^\dagger=(A^T D)^{-1} A$ denotes the Moore-Penrose pseudoinverse.

Since different amount of smoothing should be usually applied in the horizontal and the vertical directions of T, it is reasonable to use two penalty factors with two separate smoothness parameters, which control the smoothness in each direction. We used the $L_2$ norm of a finite difference operator as the penalty factor, yielding $$c=[B^T B+\lambda_x(D_x B)^T(D_x B)+\lambda_y(D_y B)^T(D_y B)]^\dagger t,\qquad(42)$$

where $D_x$ and $D_y$ are the row-wise and the column-wise discrete derivative operators and $\lambda_x$ and $\lambda_y$ are smoothness parameters controlling the smoothness of $\tilde{T}$ in the x- and y-direction, respectively. The resulting smooth stripe id image $\tilde{T}$ is given (in column stack representation) by t+Bc.

Figure 9:
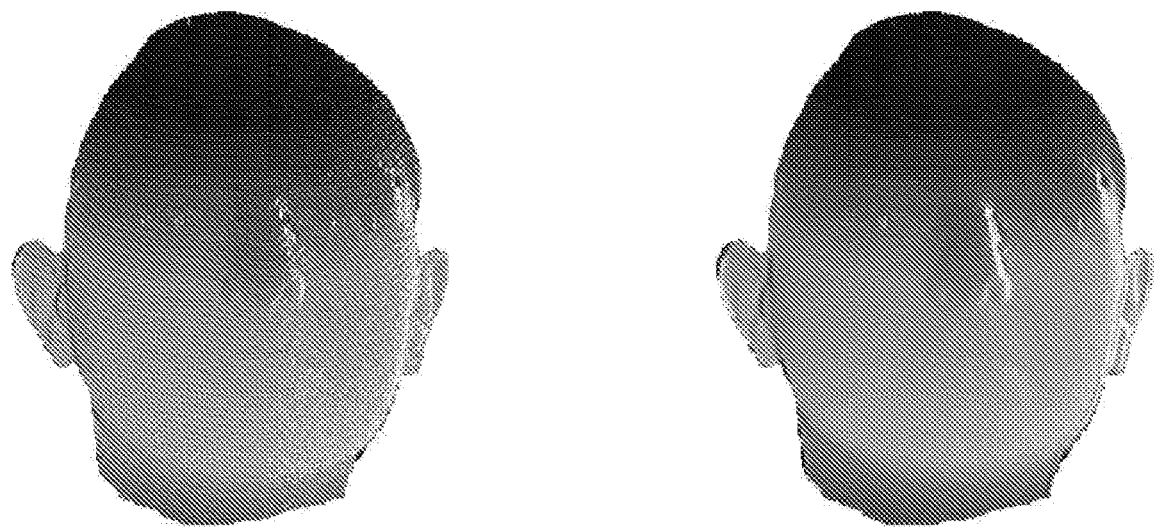
FIG. 9 depicts images of a human face reconstructed using an embodiment of the system.

FIG. 9A-B presents the T image of a human face obtained by directly decoding the stripe ids (FIG. 9A) and by using fidelity-weighted smooth cubic spline fitting (FIG. 9B). Note that quantization noise is less significant in the latter case.

Figure 10:
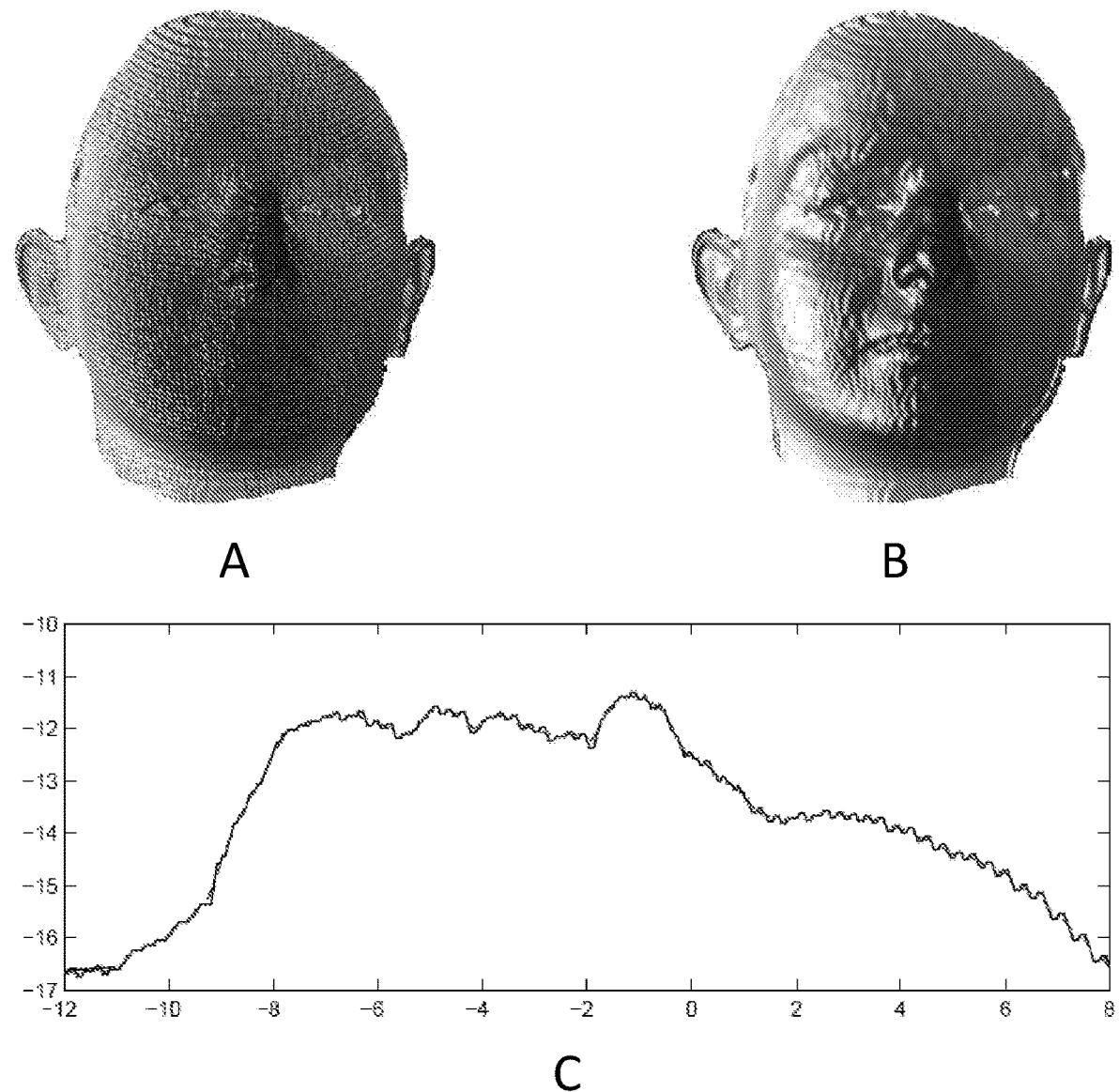
FIG. 10A-C depicts the reconstructed surface and a vertical profile of the Z-map for an embodiment of the system.

FIG. 10A-C depicts the reconstructed surface with (FIG. 10B) and without (FIG. 10A) using sub-stripe resolution. FIG. 10C shows a vertical profile of the Z-map without using sub-stripe resolution (solid) and using sub-stripe resolution (dashed).

Calibration

In an embodiment, to find the camera and the projector matrices, the automatic calibration procedure described hereinabove was used. As the calibration object, a precisely built 15×15×15 cm wooden pyramid attached with 3 mutually perpendicular planes attached to a "background" plane, was used. Object surfaces were made nearly Lambertian using white mate finishing.

Figure 11:
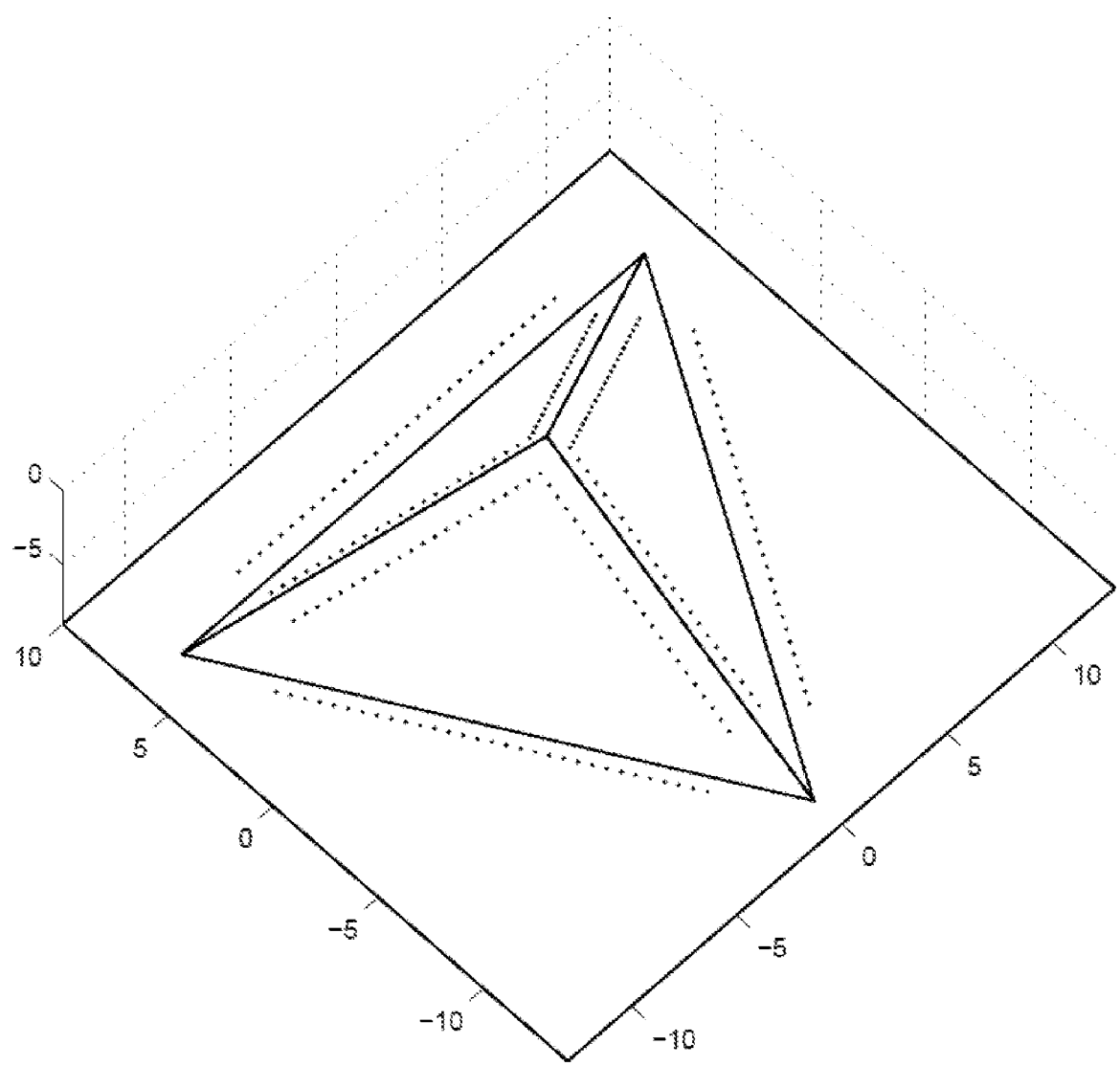
FIG. 11 illustrates an embodiment of a calibration object.

228 circular fiducial points were marked on the calibration object surfaces. The points were grouped into sets of collinear equally-spaced marks, 3 sets of 33 points each on the background plane, and two sets of 22 points each on each of the pyramid sides (FIG. 11). WCS was defined as the local coordinate system of the calibration object.

At the first stage, the calibration object was scanned and a sub-stripe resolution stripe id image $\tilde{T}$ was calculated from the raw data. At the second stage, the full-illumination image $I_H$ was binarized, the fiducial points were automatically located and their centroid coordinates were calculated. A set of 228 stripe ids at locations corresponding to the fiducial point centroids, together with the centroid locations themselves was used as the input for the calibration algorithm. For numerical stability, WCS coordinates of the calibration objects, the image plane coordinates of the camera and the projector stripe ids were normalized to [−1,1].

Figure 12:
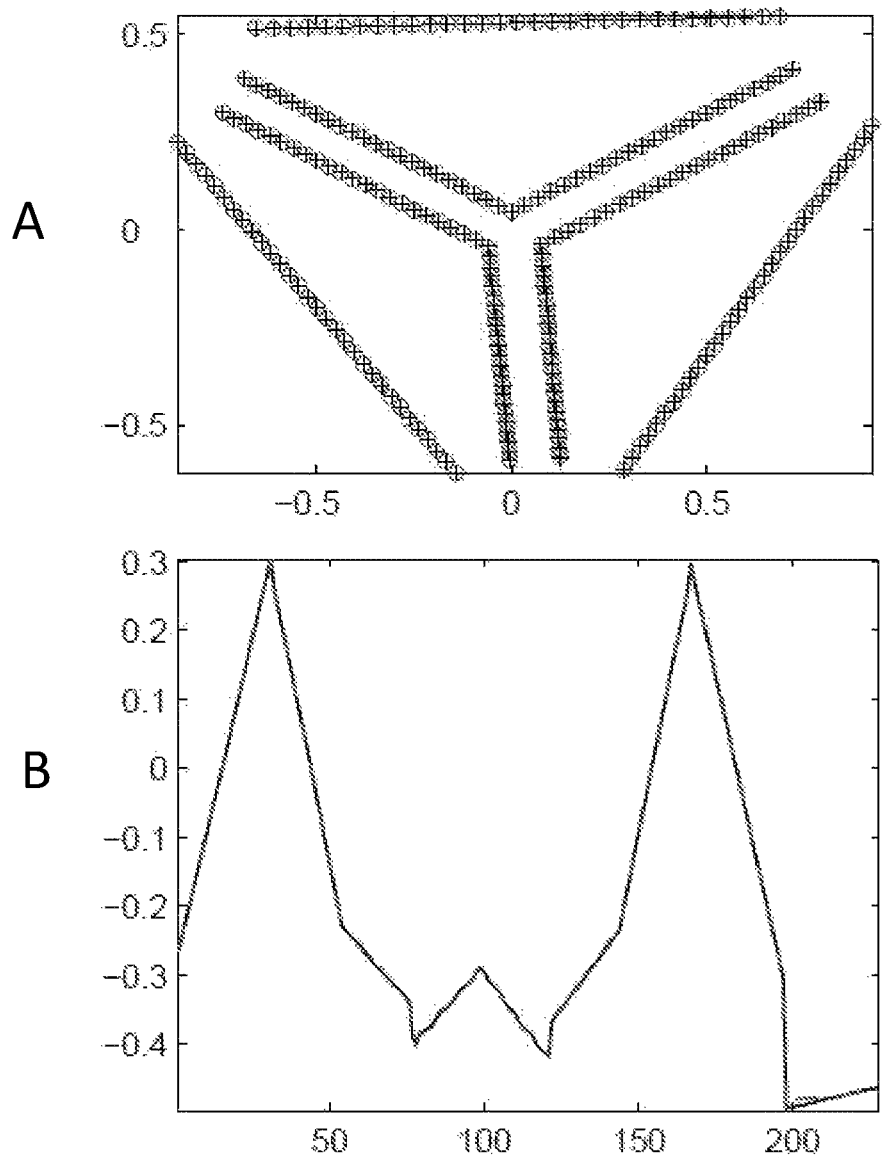
FIG. 12 depicts forward projections of the theoretically calculated calibration object fiducial points for an embodiment of the system.

First, camera and projector PPMs that minimize the forward projection error were found by solving eq. (31). These matrices were used as the initial point of the Newton algorithm, which converged to the solution of eq. (33), yielding camera and projector matrices, which minimize the backprojection error. FIG. 12A-B depicts the forward projection of the theoretically calculated calibration object fiducial points, onto the camera and the projector coordinate system. The measured fiducial points centroids and projector stripe ids are shown as a reference. FIG. 12A shows the object points reprojected to the camera image plane (circles) and the measured fiducial point centroids (crosses). FIG. 12B shows the object points reprojected to the projector coordinate system (dashed) and the measured stripe ids (black). In both FIG. 12A and FIG. 12B, the coordinates are normalized.

Table 1 shows the RMS and the maximum reconstruction errors of the calibration object in five tests with random camera and projector locations. Two cases are studied: 1) when the camera and the projector matrices are obtained by minimizing the forward projection error and 2) when the camera and the projector matrices are obtained by minimizing the backward projection error. The errors were calculated on a set of 100,000 points, with the analytical plane equations of the calibration object serving as a reference. Table 2 shows the improvement of the RMS and the maximum reconstruction error when using the optimal backprojection instead of the optimal forward projection. RMS was improved in all tests (improvement ranging from 1.44% to 45.66%, 12% on average). Maximum error was improved in all tests except Test 2, where the maximum error obtained using the optimal backprojection worsened by 6.58% (the fact that improvement in the RMS error was observed in Test 2 suggests that the degradation in the maximum error might have been caused by a spurious pixel). The maximum improvement, about 50%, was obtained in Test 5.

TABLE 1

RMS and maximum errors for reconstruction of the calibration object using the optimal forward projection and the optimal backward projection.

| | Optimal projection | | Optimal backprojection | |
|---|---|---|---|---|
| Test | RMS (mm) | Max. (mm) | RMS (mm) | Max. (mm) |
| 1 | 0.0624 | 0.2790 | 0.0577 | 0.2295 |
| 2 | 0.0626 | 0.2881 | 0.0616 | 0.3084 |
| 3 | 0.0423 | 0.2054 | 0.0417 | 0.1723 |
| 4 | 0.1599 | 0.6823 | 0.1556 | 0.6337 |
| 5 | 0.1579 | 0.6170 | 0.1084 | 0.4122 |

TABLE 2

Improvement in the RMS and the maximum error in reconstruction of the calibration object when using the optimal backprojection instead of the optimal forward projection.

| Test | RMS | Max. |
|---|---|---|
| 1 | 8.15% | 21.57% |
| 2 | 1.62% | −6.58% |
| 3 | 1.44% | 19.21% |
| 4 | 2.76% | 7.67% |
| 5 | 45.66% | 49.68% |

The RMS error was about 0.5 mm in Tests 1-3 and about 1.6 mm in Tests 4-5. The latter degradation of the reconstruction quality was due to the highly oblique position of the calibration object with respect to the camera, which resulted in lower SNR, since less light was reflected from the object planes.

Figure 13:
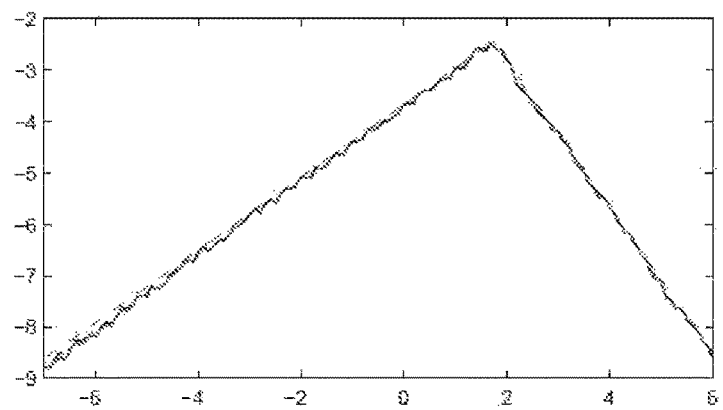
FIG. 13A-D shows profiles of a reconstructed calibration object for an embodiment of the system.
Figure 13:
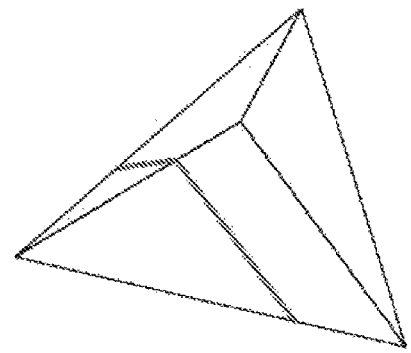
Figure 13:
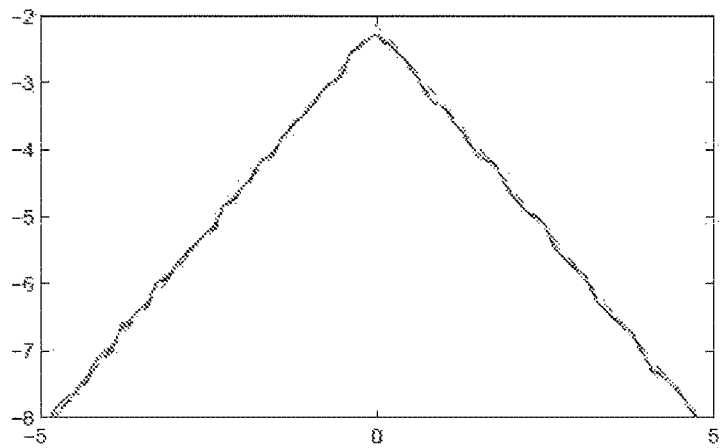
Figure 13:
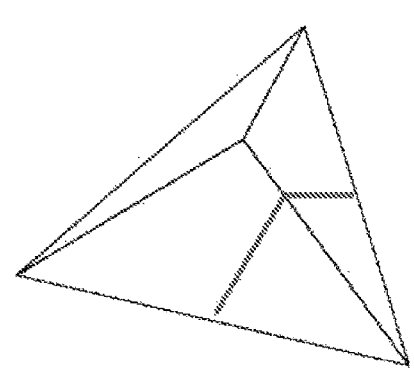

FIG. 13A-D shows two profiles of the reconstructed calibration object. Analytical object profiles are shown as a reference. FIG. 13A shows the reconstructed profile along the solid line in FIG. 13B, while FIG. 13C shows the reconstructed profile along the solid line in FIG. 13D. In FIGS. 13A and 13C, the solid line shows the reconstruction using the optimal forward projection and the dash-dotted line shows the reconstruction using the optimal backprojection. The dashed line shows the real profile. All units are in cm.

Figure 14:
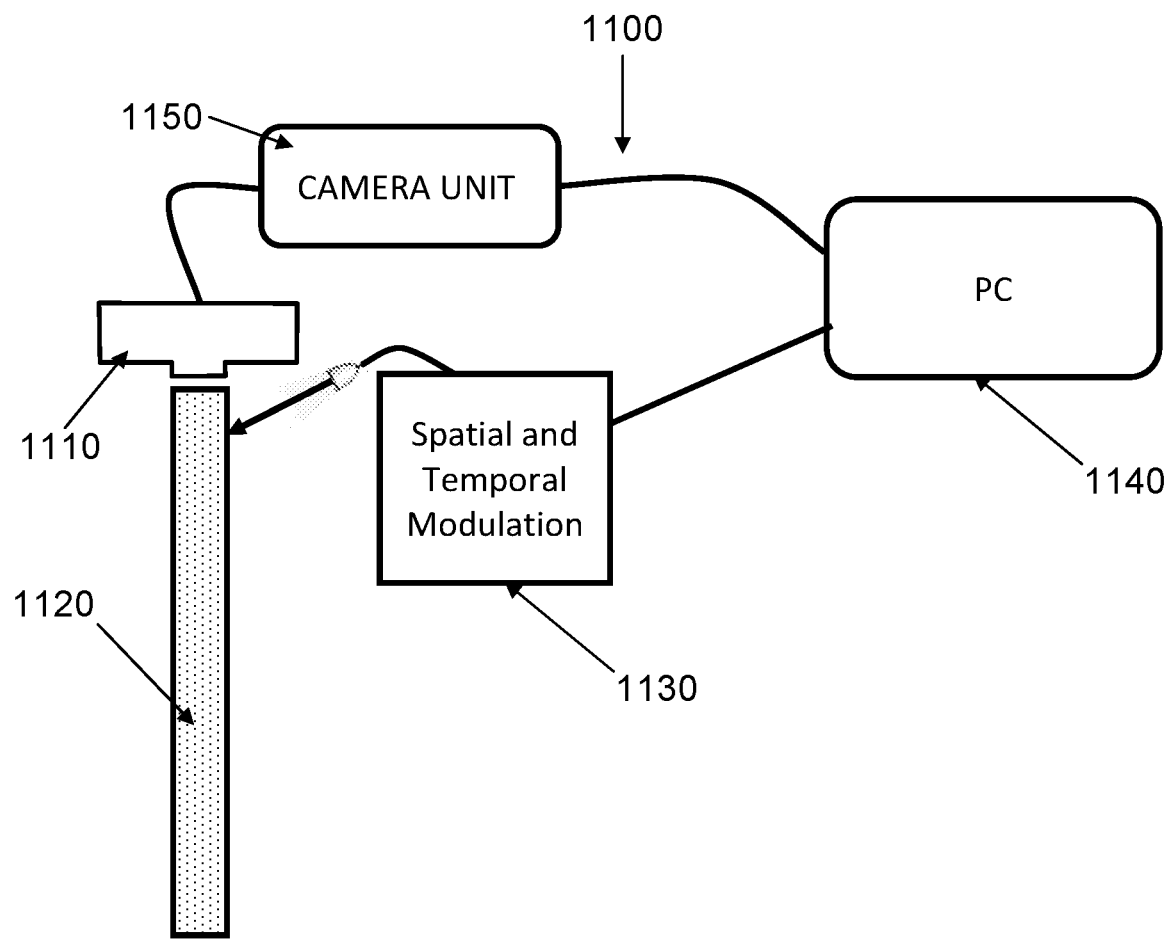
FIG. 14 schematically illustrates a laparoscopic system using structured light for generating 3D images.

FIG. 14 illustrates an embodiment of the system (1100). In this embodiment, the system comprises a PC (1140) controlling a camera unit (1115) and modulation unit (1135) for spatial and temporal modulation of the light source, a light source (1130), a camera (1110) and an endoscope (1110).

The camera unit (1115) controls the imaging system, including, where necessary, focusing of the camera (1110) and, where necessary, manipulation of the system optics so that the desired portion of the scene is at the center of the field of view. Images are transmitted from the camera (1110) to the PC (1140) via the camera unit (1115).

The modulation unit (1135) controls positioning of the light (1132), both spatially and temporally, in order to provide a set of structured light rays as described hereinabove. The modulation unit (1135) can be "upstream" of the light source (1130), as shown, or "downstream" of the light source (1130).

In embodiments where the modulation unit (1135) is "upstream" of the light source (1130), the modulation unit (1135) controls the light source (1130) directly so that light (1132) is emitted from different positions in the source (1130) at different times, in order to provide the desired set of structured light rays.

In preferred embodiments, where the modulation unit is "downstream" of the light source (1130), the modulation unit (1135) controls positioning of the light beam (1132); light from the light source (1130) is maneuvered by the modulation unit (1135) to provide the desired set of structured light rays.

Software to carry out the functions of the modulation unit (1135) and the camera unit (1115) can be local, within the unit, or central, within the PC (1140).

The structured light rays are then transmitted through the endoscope (1120) so as to illuminate the region of interest.

Reflected radiation from the objects in the region of interest is transmitted back through the endoscope (1120) so as to be received by the camera (1110), and the camera image is transmitted via the camera unit (1115) to the PC, where the 3D image of the region of interest is reconstructed, as described hereinabove. Manipulation of the camera image, such as elimination of background light or binarizing, as described hereinabove, can be carried out in the camera unit (1115), in the PC (1140), or any combination thereof.

Figure 15:
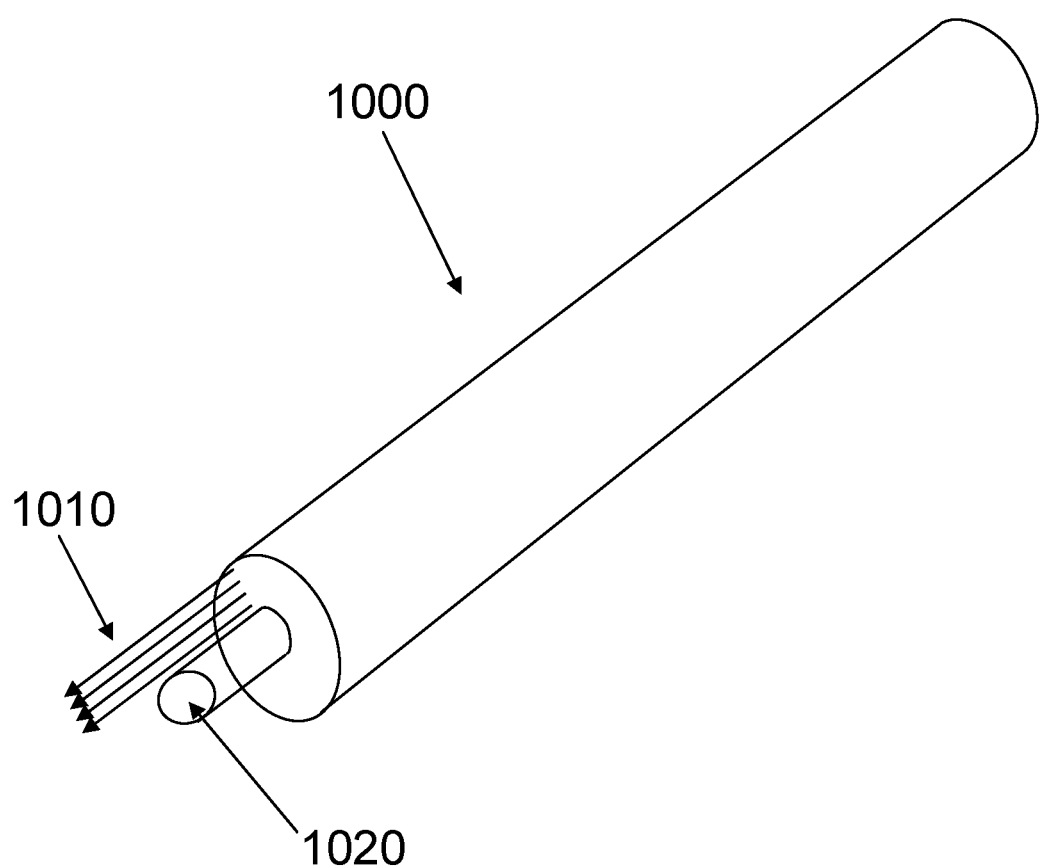
FIG. 15 schematically illustrates an embodiment of the distal end of an endoscope.

FIG. 15 shows an embodiment of a distal end (1000) of the endoscope. Modulated light (1132), after transmission through the endoscope, is emitted by the endoscope's optical transmission channels. After reflection from an object (not shown) it is received by the distal end of the camera optics (1020). The distal end of the camera optics comprises an optical element (1025), typically a lens or prism. This optical element (1025) is at an angle to the laparoscope other than 90 degrees, since, as described hereinabove, the optic axis of the camera can not be parallel to the plane of the structured light. In preferred embodiments, the angle between the plane of the structured light rays and the normal to the face of the distal optical element is between about 30 degrees and about 60 degrees.

Example 2

In some embodiments, the physical setup is similar to that of the embodiment of Example 1 (see FIG. 1) and, as in the embodiment of Example 1, a calibration object of known shape and size (the world object) is illuminated by a set of rays of light (the projector, in the projector coordinate system) emitted from known positions, in known directions and at known times. These rays are reflected from the calibration object (the object, in the world coordinate system) and generate at least one 2D camera image (the camera image, in the camera coordinate system).

However, instead of the operators of Example 1, polynomial fits are made to the known spot positions on the camera images, given the known ray positions, the known spot positions on the camera images and the known shape and size of the calibration object. From the polynomial fits, the locations of positions on the surface of an unknown object can be found.

In the embodiment of Example 2, the projector (light source) projects a coded stripe pattern on the object or objects to be viewed and the camera captures an image of the reflected light. Hence, for each visible point in the scene there is a corresponding stripe number and image location (in pixel coordinates). Given the parameters of the system, each strip value defines a plane in the world (the space being viewed) and each pixel defines a ray in the world. The intersection of the plane and the ray defines a unique 3D location in the world. The parameters of the system are obtained during calibration. As in Example 1, a calibration object is placed at a known position in the field of view. The calibration object comprises a set of fiducial marks whose spatial location is known to high accuracy. The system is operated normally and the pixel coordinates are found for each of the fiducial marks. These triples of fiducial mark, pixel and stripe coordinates are used to estimate the unknown parameters of a mathematical model of the system.

In practice, the projector projects a sequence of 9 banded light patterns onto the scene. The first pattern is full illumination. The remaining patterns provide temporal encoding, with each of the 8 patterns providing one bit in an 8 bit binary grey code for the stripe value. In general, for a b bit code, the $k^{th}$ bit (where k=0, 1, ..., b−1) of the code for the $n_{th}$ value (n=0, 1, ..., $2^{b-1}$) is given by $$\left[\frac{1}{2}\left(\frac{n}{2^k}+1\right)\right]$$

mod 2. An important property of the code is that no two edges (level changes) are coincident throughout the sequence. As the most likely place to erroneously read a bit is at a level change, the code helps reduce the possibility of detecting more than one bit of the code erroneously. In addition, detecting a bit incorrectly at a level change only alters the stripe value by one. It should be noted that this stripe encoding completely eliminates the need for resolving any correspondence between points in the image and stripes.

Projector lens distortion results in each stripe forming a slightly curved surface instead of a plane, and camera lens distortion results in the image point being slightly displaced from its nominal position. Furthermore, the discrete nature of pixel-based cameras and projectors gives rise to uncertainty in the true pixel coordinates and stripe value.

In preferred variants of the present embodiment, correcting for the effects of projector lens distortion is included in the model of the projector.

In preferred variants of the present embodiment, correcting for the effects of camera lens distortion is via subpixel and substripe operators.

In the present embodiment, the uncorrected transformation of a point P from the world coordinate system $C_w$, to the camera coordinate system $C_c$ is $$\begin{pmatrix} x_c \\ y_c \\ z_c \end{pmatrix} = R_c \begin{pmatrix} x_w \\ y_w \\ z_w \end{pmatrix} + T_c \quad (43)$$

where $X_c=(x_c, y_c, z_c)$ is the location of the point in camera coordinates, $X_w=(x_w, y_w, z_w)$ is the location of the point in camera coordinates, $R_c$ is a 3×3 rotation matrix and is a 3×1 translation vector.

The "principal point" is the intersection of the imaging plane with the optical axis. Without loss of generality, a 2D image coordinate system can be defined as being in the image plane with its origin located at the principal point. Let p be the projection of the point P onto the image plane for a non-distorting projector and let the coordinates of p be $(\tilde{x}_i, \tilde{y}_i, 0)$. Then $$\begin{pmatrix} \tilde{x}_i \\ \tilde{y}_i \end{pmatrix} = \frac{f_c}{z_c}\begin{pmatrix} x_w \\ y_c \end{pmatrix} \quad (44)$$

where $f_c$ is the "principal distance".

As described above, the projective lenses slightly distort the plane of the projected light into a curved surface. To correct for this, let $(x_i, y_i, 0)$ be the observed location in the image plane of the point p, after projection by a real, distorting projection system. Then, $$\begin{pmatrix} x_i \\ y_i \end{pmatrix} = \begin{pmatrix} \tilde{x}_i \\ \tilde{y}_i \end{pmatrix}[1 + K_c(\tilde{x}_i^2 + \tilde{y}_i^2)] \quad (45)$$

where $K_c$ is a coefficient determined by the amount of radial distortion.

The effects of pixels size and imager speed can also be factored in. Let $C_{pixel}$ be a pixel coordinate system associated with the digital image, where the location of a point is given by (x,y). Then the pixel coordinates are related to the image coordinates by $$\begin{pmatrix} x \\ y \end{pmatrix} = \begin{pmatrix} s_c^x & k_c \\ 0 & s_c^y \end{pmatrix}\begin{pmatrix} x_i \\ y_i \end{pmatrix} + \begin{pmatrix} c_c^x \\ c_c^y \end{pmatrix} \quad (46)$$

where $S_c^x$ and $S_c^y$ are scale factors in pixels/mm, $C_c^x$ and $C_c^y$ are the pixel coordinates of the principal point and $k_c$ is a shear coefficient in pixel/mm.

The model for the projector is similar to that for the camera, as the projector can be regarded as a camera with a 1D image, acting in reverse.

However, the projector model differs from the camera model in that the stripe coordinate system $C_s$ is 1D, unlike the 2D camera coordinate system $C_p$, leading to the equation:

$$x_s = s_p^x x_i + c_p^x \quad (47)$$

Where $s_p^x$ is a scale factor and $C_p^x$ is the pixel coordinate of the principal point of the projection system.

Physically, each stripe value xx gives rise to a unique line on the projector given by $$\{(x_i, y_i) : x_i = (x_s - c_p^x)/s_p^x, y_i \in \Re\}.$$

The line is projected and distorted by the lens, giving rise to a slightly curved surface in the world.

Altogether, the following set of equations describes the transformations:

$$\begin{pmatrix} x_c \\ y_c \\ z_c \end{pmatrix} = R_c \begin{pmatrix} x_w \\ y_w \\ z_w \end{pmatrix} + T_c \quad (43)$$

$$\begin{pmatrix} \tilde{x}_i \\ \tilde{y}_i \end{pmatrix} = \frac{f_c}{z_c} \begin{pmatrix} x_w \\ y_c \end{pmatrix} \quad (44)$$

$$\begin{pmatrix} x_i \\ y_i \end{pmatrix} = \begin{pmatrix} \tilde{x}_i \\ \tilde{y}_i \end{pmatrix} [1 + K_c(\tilde{x}_i^2 + \tilde{y}_i^2)] \quad (45)$$

$$x_i = s_p^x x_i + c_p^x \quad (47)$$

The above models describe the geometric behavior of the camera and projector and are based on a physical understanding of these devices. $K_c=0$ and $k_c=0$ describe a perfect camera. Similarly, $K_p=0$ describes a perfect projector.

It is clear that there is a redundant parameter within the set of camera parameters $\{s_c^x, s_c^y, f_c\}$. This can be dealt with by arbitrarily fixing one of them. For the calibrations described hereinbelow, $f_c$ is set to 1.

Lens distortion has been incorporated as a function of the transform from $(\tilde{x}_i, \tilde{y}_i, 0)$ to $(x_i, y_i, 0)$. This is because the distortion is a 2D phenomenon whereas only one coordinate of the position of a point on the projector emitter is available. However, the ranges of both formulations are almost equivalent for typical system configurations. Therefore, this modification makes little difference to the solution.

The camera and projector models can be summarized as follows. Let $$\Theta_c = s_c^x s_c^y c_c^x c_c^y k_c K_c \omega_c^1 \omega_c^2 \omega_c^3 T_c^1 T_c^2 T_c^3)^t \quad (48)$$

$$\Theta_p = s_p^x c_p^x K_p \omega_p^1 \omega_p^2 \omega_p^3 T_p^1 T_p^2 T_p^3)^t \quad (49)$$

where $\omega_c^k$, k=1 . . . 3 and $\omega_n^k$, k=1 . . . 3 parameterize $R_c$ and $R_p$ respectively (e.g. Euler angles). The first six parameters of the camera model and the first three parameters of the projector model are referred to as "intrinsic parameters" because they are independent of the world coordinate frame.

Using the above, the transformation from world coordinates $p_w$ to pixel coordinates $p_p$ can be written as $$p_p = F_c(p_w; \Theta_c). \quad (50)$$

Similarly, the transformation from world coordinates to the stripe value $p_x$ can be written as $$p_s = F_p(p_w; \Theta_p). \quad (51)$$

Both the calibration and spatial intersection procedures require the pixel coordinates and the stripe value of points of interest in the world (field of view). Obtaining good estimates for the value of these quantities is important in order to obtain accurate estimates of the parameters of the system during calibration and accurate estimates of 3D point locations during spatial intersection.

Subpixel Estimation

During calibration, the subpixel locations of the centroids of the fiducial marks on the calibration reference are required. The grayscale centroid operator can be used to estimate the centroids of the fiducial marks in the image. Such centroid-based techniques have the following advantages:

They are robust to noise, since they are based on integration rather than the differentiation of many edge detectors.

They are robust to small amounts of aliasing. Theoretically, they are exact if the sampling frequency is greater than the Nyquist frequency.

They are computationally inexpensive.

However, the centroid of the image of a fiducial mark does not in general coincide with the image of the centroid, due to perspective distortion. This introduces a systematic error in the centroid estimate and is a fundamental limitation of centroiding techniques.

Ignoring lens distortion, an estimate of this error can be obtained as follows. Consider a flat circular region $\Delta$ of radius r. let n be the normal to $\Delta$ and q be the location of the centroid of $\Delta$, both in camera coordinates. If c denotes the image of the centroid and denotes the centroid of the image of $\Delta$ then $$c = \frac{f_c}{t_3}\begin{pmatrix} t_1 \\ t_2 \end{pmatrix} \quad (52)$$

$$\hat{c} = \frac{f_c}{t_3^2 + r^2(n_3^2 - 1)}\begin{pmatrix} t_1 t_3 + r^2 n_1 n_3 \\ t_2 t_3 + r^2 n_2 n_3 \end{pmatrix}. \quad (53)$$

As required, $\hat{c}$ reduces to c when n=$e_3$ ($\Delta$ parallel to the image plane. The error in the image plane is given by $e_p = c - \hat{c}$. This error can be transformed into pixel coordinates using the scale factors and shear coefficient defined hereinabove (eq. 46).

Figure 16:
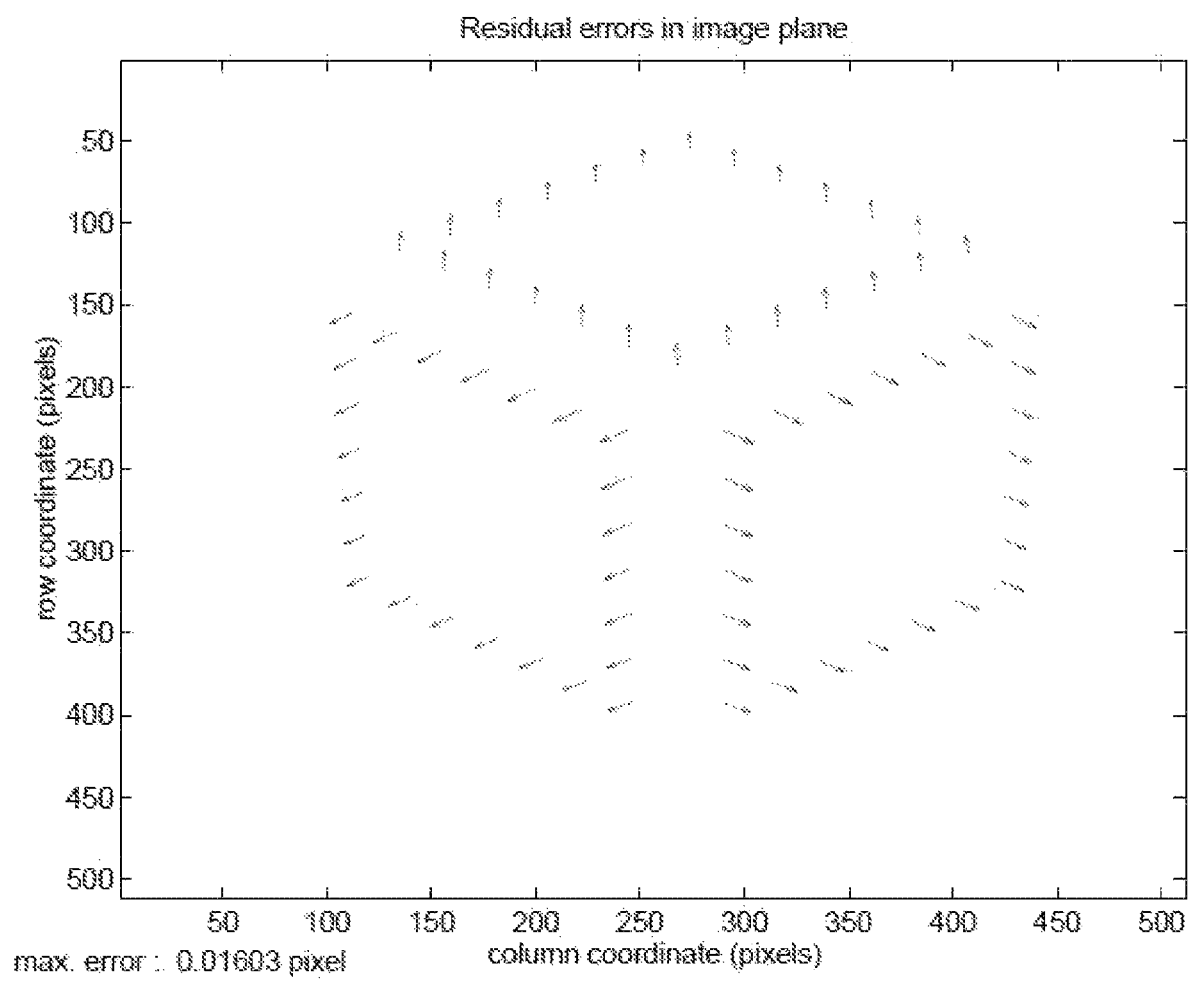
FIG. 16 shows a plot of errors in pixel coordinates for a typical calibration configuration.

FIG. 16 shows a plot of these errors in pixel coordinates for a typical calibration configuration. Each error is represented as a vector with its base at the associated fiducial mark. The vector magnitudes have been scaled by a factor of 1000 for clarity. In the current system, these errors are considered acceptable.

During special intersection, two situations can arise, one where the image location is freely chosen and the other where it is dictated by a feature in the world. The need to use subpixel estimation does not arise in the first situation, e.g., during generation of a dense range map with image locations at the pixel lattice points. The type of subpixel operator used during the second situation depends on the nature of features (such as, but not limited to edges, ridges, blobs, voids, or transparent or translucent regions).

Substripe Estimation

During calibration and special intersection, the substripe values of specified world points are required.

Substripe estimation is more difficult than subpixel estimation. One reason for this is that the stripe information is not directly available from the projector in the sense that the pixel location information is available from the camera. It is the images of the stripes cast on the scene which are used to recover the stripe values. In this way, the stripes are effectively samples twice, once by the predetermined locations of the stripes emitted by the projector, and once from the image in the camera. Another difficulty, specific to temporally encoded systems, is that the stripe values are encoded in a sequence of images rather than available in a single image as for pixel locations.

It is assumed that the 8 bit stripe value is available for each pixel in the image. The image formed from these values is referred to as a "stripe image". The discrete nature and coarseness quantization of the stripe image gives rise to poor accuracy if used directly. The algorithm adopted for sub-stripe estimation is simple. A region of interest, $\Omega$, is established with its center at the subpixel location, $(x_p,y_p)$, where the substripe estimate, $x_x$, is to be determined. A least-squares polynomial facet is fitted to the stripe image in $\Omega$ and the substripe estimate made by interpolating this facet.

If the underlying surface is flat, a planar facet is fitted to the stripe image $\Omega$. Assuming no lens distortion in the camera and the projector, the stripe values and the pixel coordinates for a planar patch in the world will be related by a rational function because the composition of two projective maps is a projective map. Hence a planar facet does not model perspective effects precisely. The errors introduced by using a planar facet can be estimated as follows.

Let $C_c$ and $C_p$ denote the 3×4 and 2×4 Perspective Transformation Matrices (PTMs) for the camera and projector, respectively. Both the camera and the projector are assumed to be distortionless. Let T be a 4×3 homogeneous transformation matrix describing the coordinate transformation between a 2D coordinate system associated with the planar patch and the world coordinate system. It follows that $$\alpha \begin{pmatrix} x_s \\ 1 \end{pmatrix} = C_p T (C_c T)^{-1} \begin{pmatrix} x_p \\ y_p \\ 1 \end{pmatrix} \tag{54}$$

This shows that the stripe values and pixel coordinates are related by an equation of the form $$x_x = \frac{n_1 x_p + n_2 y_p + n_3}{d_1 x_p + d_2 y_p + d_3} \tag{55}$$

Let $x_x$ be the true substripe value at subpixel location $(x_p,y_p)$ calculated using eq. (54). Let $(X_p,Y_p)$ be the n×2 matrix of pixel coordinates in $\Omega$ and $X_x$ be the n vector of substripe values at coordinates $(X_p,Y_p)$. The 3×1 vector of coefficients of the least squares plane fitted to $X_x$ on $\Omega$ is given by $$c = (A^t A)^{-1} A^t X_s \tag{56}$$

where $A=[X_p\ Y_p\ 1n]$ is the n×3 design matrix associated with the plane. The estimate of the $x_x$ is given by $$\hat{x}_s = c_1 x_p + c_2 y_p + c_3 \tag{57}$$

and the error is given by $\epsilon_{\hat{x}_s} = x_s - \hat{x}_s$.

Figure 17:
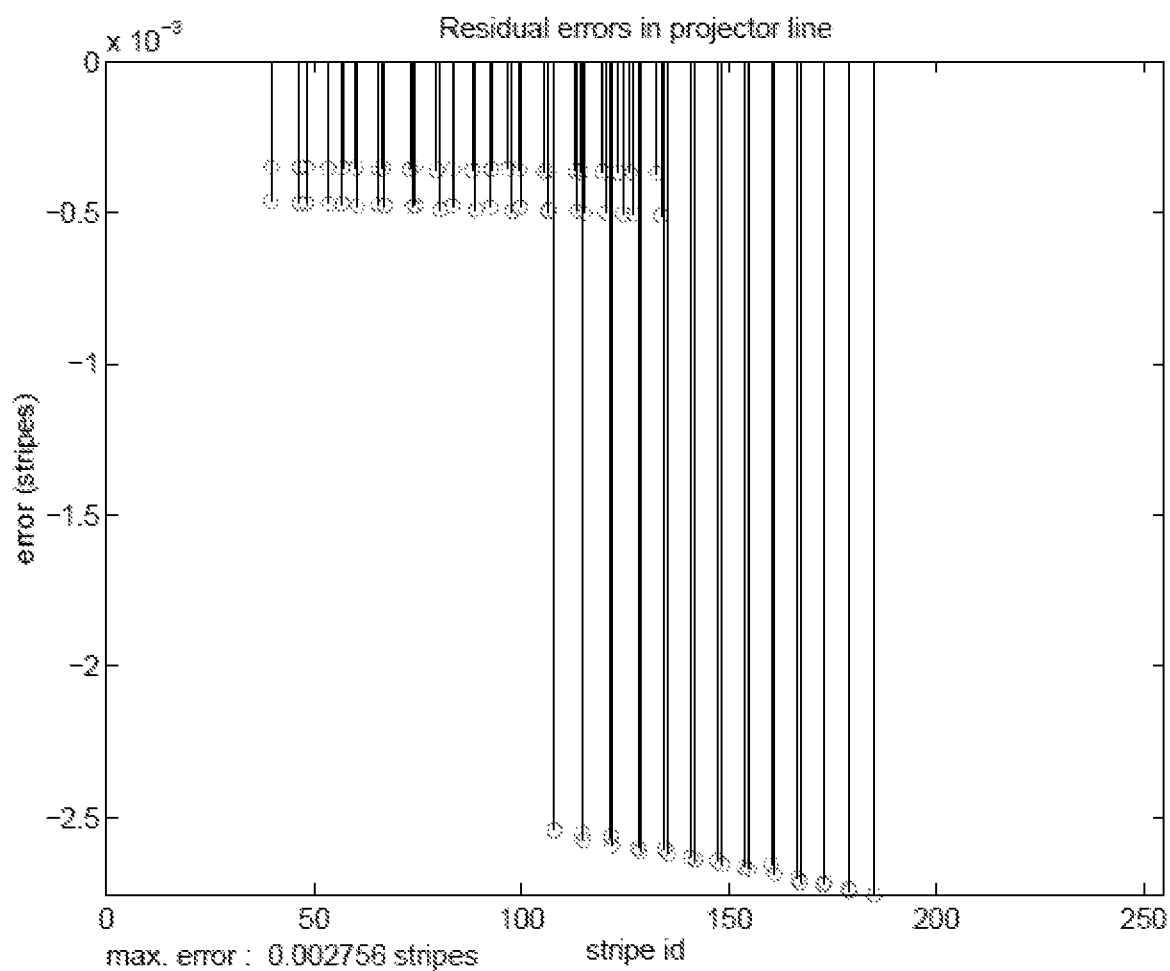
FIG. 17 shows a stem plot of errors for a typical calibration configuration.

FIG. 17 shows a stem plot of these errors for a typical calibration configuration. The horizontal axis gives the stripe value calculated at the centroids of the fiducial marks and the vertical lines give the error in stripes at these locations. The errors are insignificant compared with the effects which result from the 8 bit quantization of the stripe value and therefore can typically be ignored.

In the more general case of a curved surface, higher order 2D polynomial facets are fitted to the stripe image. The order of the facet model depends on the size of the region of interest $\Omega$, which must cover a sufficient number of stripes. Typically, a region of interest of size 17×17 pixels and 2D third-order polynomials are used. Note that polynomial fitting does not introduce blurring in the sense of low-pass filtering. For example a polynomial of degree n (which can have considerable oscillation) is invariant to a polynomial filter of order n (i.e. the filter which is defined by fitting and interpolating a polynomial of degree n).

Planar facets are only used when the surface under consideration is known to be flat, such as the faces of the calibration reference. In all other cases. a polynomial facet is used. The planar facet is embodied because it provides superior estimation when the surface has very low curvature.

Calibration

Calibration involves estimating the unknown parameters relating the world points, the projector points and the image points from a number of known world points and their corresponding pixel coordinates and stripe values.

For a calibration object with n fiducial marks, let $p_w(j)$, $p_p(j)$ and $p_s(j)$ be the world coordinates, the pixel coordinates and the stripe coordinates, respectively, of the jth fiducial mark. In addition, let $P_w$, $P_p$ and $P_s$ be vectors of sizes 3n, 2n and n, respectively, formed by stacking the coordinate vectors for the world points, the pixel points and the stripe points, respectively. The vectors $P_p$ and $P_s$ are measured from the image sequence as described hereinabove and will consequently suffer from measurement noise.

If $\mu_{P_p}$ and $\mu_{P_s}$ are the true values of $P_p$ and $P_s$, respectively, then the observations are given by $$P_p = \mu_{P_p} + \epsilon_p \tag{58}$$

$$P_s = \mu_{P_s} + \epsilon_s \tag{59}$$

and the model can be written as $$\mu_{P_p} - F_c(P_w; \Theta_c) = 0 \tag{60}$$

$$\mu_{P_s} - F_p(P_w; \Theta_p) = 0 \tag{61}$$

In this derivation, the assumptions are:
$P_w$ is measured without error.
$P_p \sim N(\mu_{P_p}, \sigma_p^2 I_{2n})$
$P_s \sim N(\mu_{P_s}, \sigma_s^2 I_n)$
Maximum Likelihood Estimation of $\{\Theta_c, \Theta_p\}$ leads to the non-linear least squares (NLLS) problem $$\min_{\Theta_c} \|P_p - F_c(P_w; \Theta_c)\|^2 \tag{62}$$

$$\min_{\Theta_p} \|P_s - F_p(P_w; \Theta_p)\|^2 \tag{63}$$

which can be solved using any general NLLS solving algorithm known in the art. Non-limiting examples of such algorithms are Gauss-Newton or Levenberg-Marquardt.

Obtaining good initial estimates for the parameters is desirable as (1) it helps ensure that the global minimum is obtained and (2) reduces computation by reducing the number of iterations required. Initial estimates can be obtained from a variety of sources, depending on the nature of the problem. A typical approach is to estimate and decompose the PTMs for the camera and the projector.

Spatial Intersection

Special intersection is used to find an estimate of the location of a point in the world coordinate system given its pixel coordinates and stripe value. The lens distortion in the projector results in slightly curved surfaces being projected onto the scene rather than planes. Consequently, the special intersection procedure involves solving a homogeneous non-linear system in three variables. However, linear methods can be used to calculate a good initial approximation and physical considerations preclude the presence of any other solutions in a large neighborhood of the true solution.

Let $p_p=(x_p,y_p)^t$ and $p_x=(x_s)$ be the pixel coordinates and stripe value of a point P. Then the world coordinates of P, denoted $p_w$, are given by the solution of the non-linear system $$\begin{pmatrix} p_p \\ p_s \end{pmatrix} - \begin{pmatrix} F_c(p_w; \Theta_c) \\ F_p(p_w; \Theta_p) \end{pmatrix} = 0 \qquad (64)$$

This problem can be solved using any general technique known in the art, for non-limiting example, a quasi-Newton strategy.

The initial linear estimate of $p_w$ is found as follows. Let $C_c^k$ be the kth row of the 3×4 camera PTM and $C_p^k$ be the kth row of the 2×4 projector PTM. Then the PTM equations relating $p_w$, $p_p$ and $p_x$, i.e., $$\beta_p \begin{pmatrix} p_p \\ 1 \end{pmatrix} = C_c \begin{pmatrix} p_w \\ 1 \end{pmatrix} \qquad (65)$$

$$\beta_s \begin{pmatrix} p_s \\ 1 \end{pmatrix} = C_p \begin{pmatrix} p_w \\ 1 \end{pmatrix}$$

can be rearranged into the 3×4 linear homogeneous system $$\begin{pmatrix} C_c^1 - x_p C_c^3 \\ C_c^2 - y_p C_c^3 \\ C_p^1 - x_s C_p^2 \end{pmatrix} \begin{pmatrix} \alpha p_w \\ \alpha \end{pmatrix} = 0 \qquad (66)$$

A solution to eq. (66) can be obtained (for non-limiting example) using SVD and the estimate of $p_w$ obtained from the homogeneous solution to eq. (66).

When there are a large number of points to process, computational savings can be made. A generalization of the vector cross-produce for n−1 vectors in an n-dimensional linear space can be defined implicitly by $(w, v_1 \times \ldots \times v_{n-1}) = \det(v_1, \ldots v_{n-1}, w)$. $v_1 \times \ldots \times v_{n-1}$ can be written as $\Sigma_k \det(v_1, \ldots v_{n-1}, e_k)e_k$ and is orthogonal to $v_k$ where $\{e_k\}_{k=1}^n$ are the standard basis vectors of $\Re^n$. Therefore, a solution to eq. (66) is given by the (generalized) cross product of the rows of the 3×4 matrix $$\begin{pmatrix} \alpha p_w \\ \alpha \end{pmatrix} = \sum_{k=1}^4 \det(C_r^1 - x_p C_r^3, C_r^2 - y_p C_r^3, C_p^1 - x_s C_p^2, e_k)e_k \qquad (67)$$

Dividing by α and using the linearity and antisymmetry of the determinant tensor, the kth component of $p_w$ is given by $$p_w^k = \frac{C_{1,2,1}^k - x_p C_{3,2,1}^k - y_p C_{1,3,1}^k - x_s C_{1,2,2}^k + x_s x_p C_{3,2,2}^k + x_s y_p C_{1,3,2}^k}{C_{1,2,1}^4 - x_p C_{3,2,1}^4 - y_p C_{1,3,1}^4 - x_s C_{1,2,2}^4 + x_s x_p C_{3,2,2}^4 + x_s y_p C_{1,3,2}^4} \qquad (68)$$

where $$C_{i,j,l}^k = \det(C_c^i, C_c^j, C_p^l, e_k)$$

are constants which depend only on the camera and projector PTMs and can be precomputed.

Figure 18:
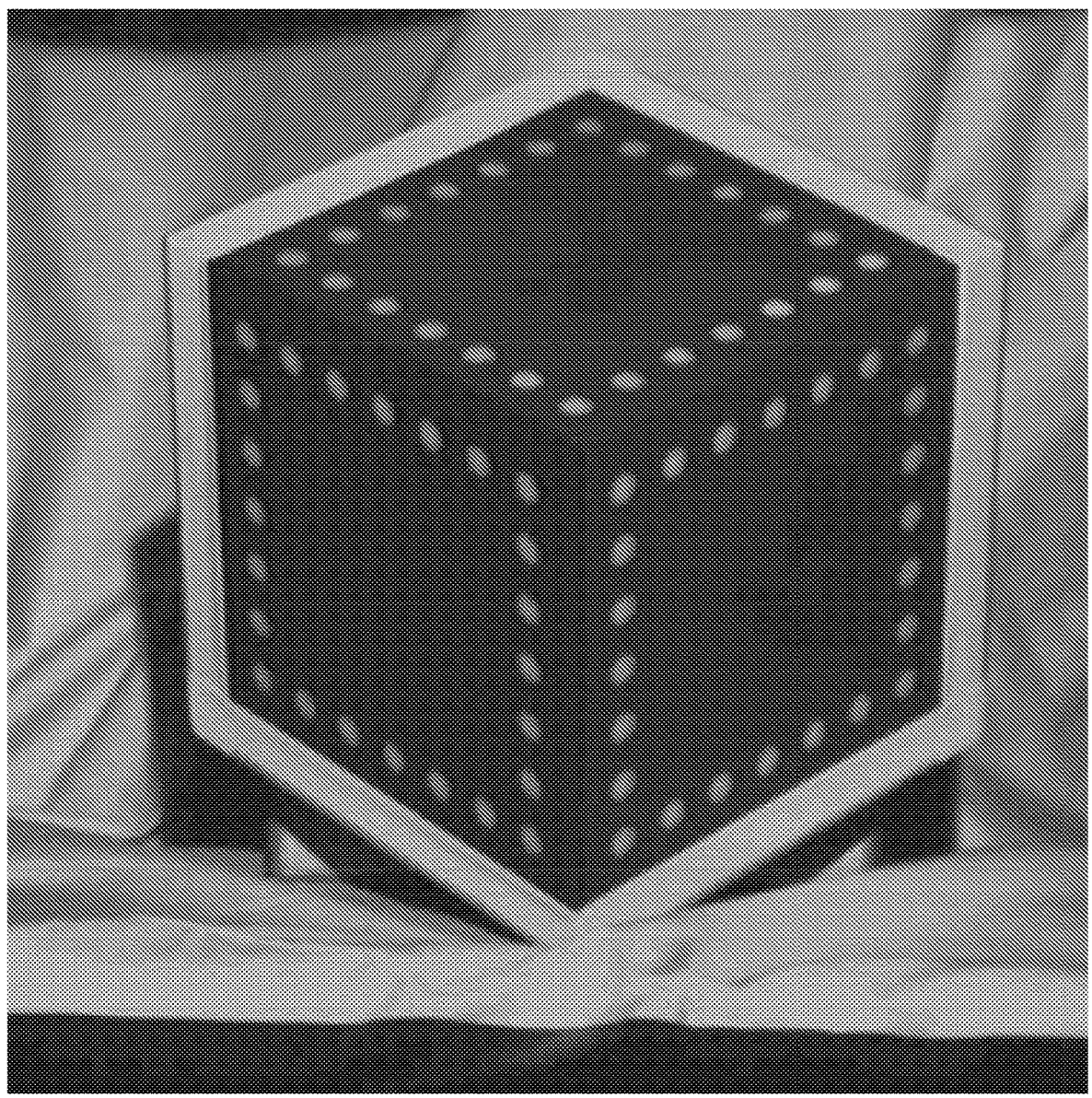
FIG. 18 shows an embodiment of a calibration object.

In these experiments, the system comprised a K2T LCS and controller housed in a Kodak projector. TM-6CN Pulnix camera and S2200 Data Cell framegrabber. The LCS shutter has 256 stripes and 512×512 images were captured. The calibration reference is a 150 mm cube with 72 fiducial marks of 5 mm radius arranged over 3 faces, as shown in FIG. 18. The 3D location of each fiducial mark centroid has been measured to an accuracy of 0.1 mm in a coordinate system attached to the cube. During calibration, this coordinate system is taken to be the world coordinates system. Calibration thus fixes the world coordinate system and all subsequent measurements are expressed in the world coordinates system. The experimental setup has the projector above the camera with the angle between their optic axes being approximately 12° to give a working volume of 250 mm diameter at 1600 mm in front of the camera.

To evaluate the performance of the system, seven trials were used with the calibration reference in a different position in each. For each trial, the observed data consists of the pixel coordinates and stripe values of the fiducial marks. The calibration parameters for each trial were extracted from the observed data using the procedure described hereinabove.

Figure 19:
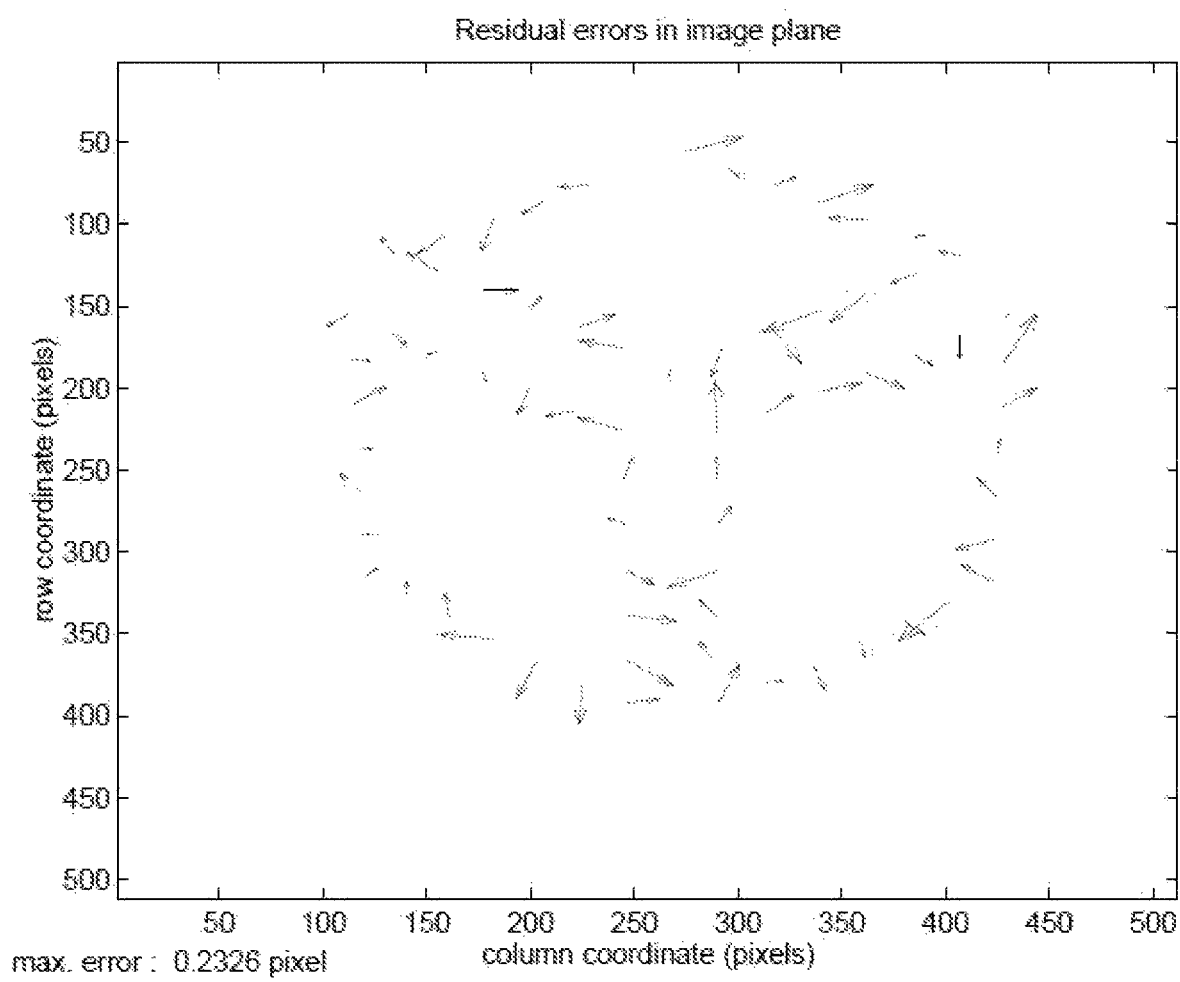
FIG. 19 shows a plot of pixel residuals.
Figure 20:
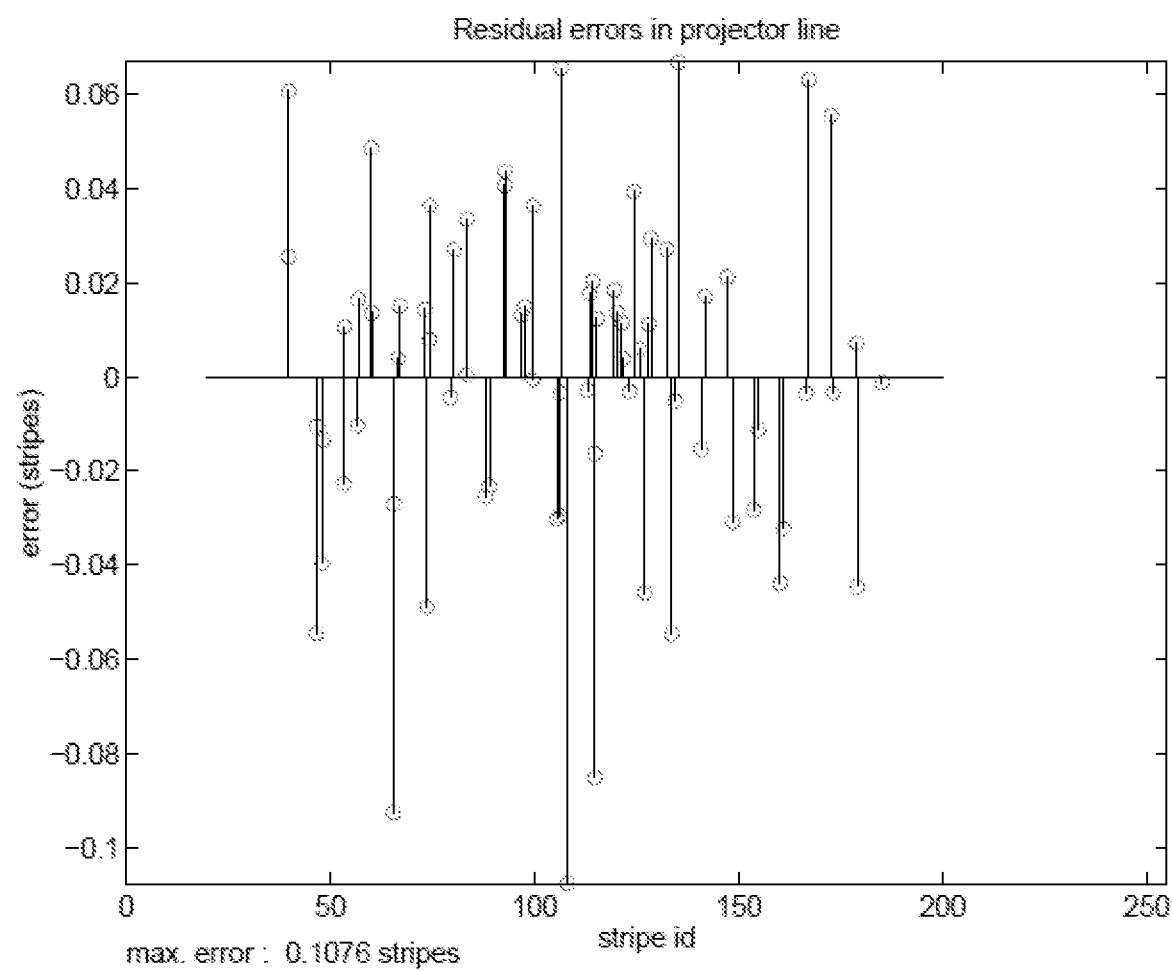
FIG. 20 shows a plot of stripe residuals.
Figure 21:
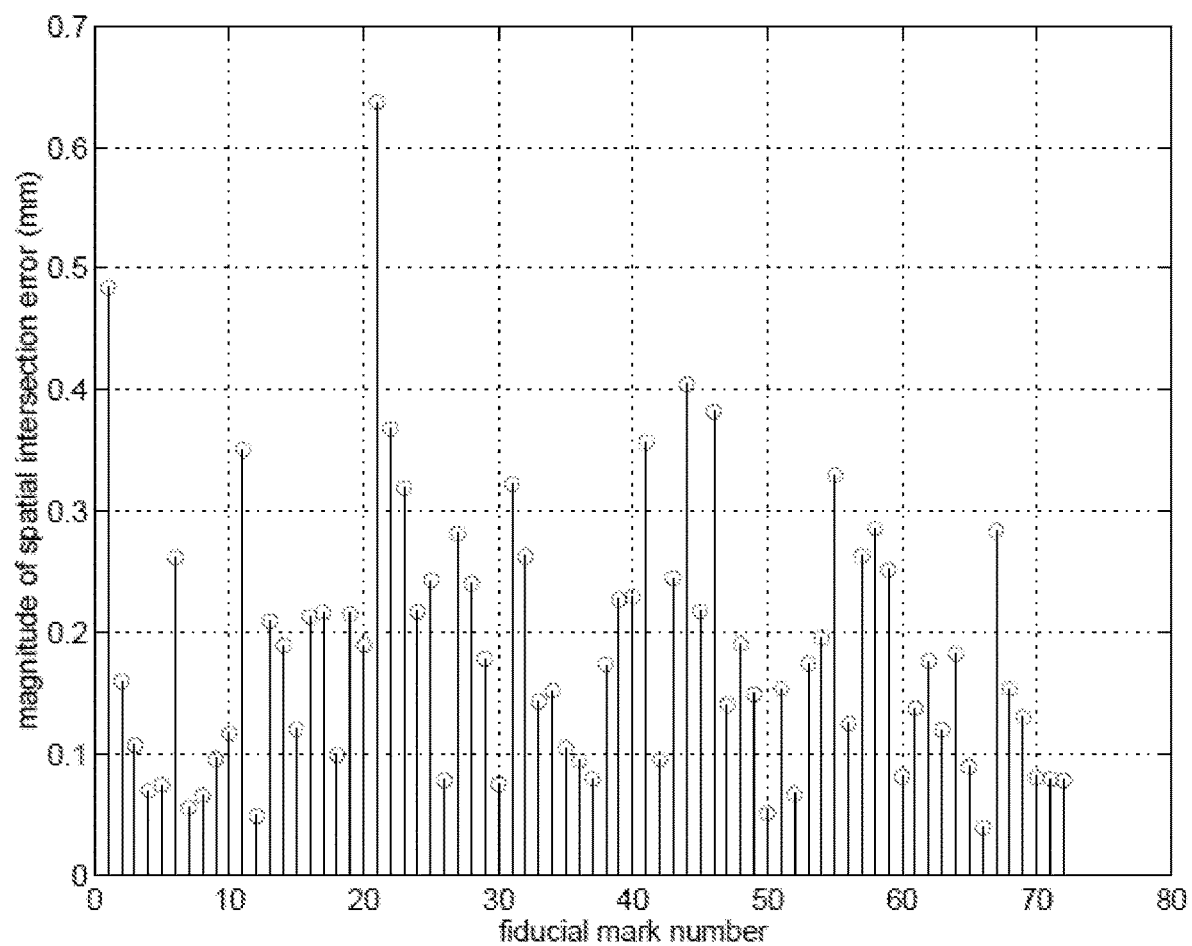
FIG. 21 shows a plot of spatial intersection errors

The estimated pixel coordinates and stripe values are obtained by projecting the world reference coordinates using the calibrated system model. The pixel residuals (FIG. 19) and stripe residuals (FIG. 20) are the difference between the measured and estimated values. The spatial intersection errors (FIG. 21) are the difference between the reference coordinates of the fiducial marks and their coordinates estimated by special intersection. FIGS. 19, 20 and 21 show the pixel residuals, stripe residuals and spatial intersection errors for trial 4. The fiducial mark numbers in FIG. 21 were obtained from an arbitrary ordering of the fiducial marks on the cube.

Table 3 shows the average magnitude of the special intersection errors for each of the calibration trials. Each average was obtained using all 72 fiducial marks. For comparison, Table 4 shows the average errors when radial distortion is neglected for the camera and projector models. Table 5 shows the average errors when no substripe estimation is used. Excluding either radial distortion or substripe estimation increases the error in all trials. On average, over all trials, adding substripe estimation improves the performance by 82% while adding lens distortion improves the performance by only 13%, showing that substripe estimation has the more significant effect.

TABLE 3

Average magnitude of the spatial intersection error for calibration trials.

| | Trial | | | | | | |
|---|---|---|---|---|---|---|---|
| | 1 | 2 | 3 | 4 | 5 | 6 | 7 |
| average error (mm) | 0.154 | 0.245 | 0.296 | 0.187 | 0.280 | 0.246 | 0.233 |

TABLE 4

Average magnitude of the spatial intersection error for calibration trials if radial distortion is neglected.

| | Trial | | | | | | |
|---|---|---|---|---|---|---|---|
| | 1 | 2 | 3 | 4 | 5 | 6 | 7 |
| average error (mm) | 0.226 | 0.283 | 0.311 | 0.223 | 0.292 | 0.261 | 0.264 |

TABLE 5

Average magnitude of the spatial intersection error for calibration trials with no substripe estimation.

| | Trial | | | | | | |
|---|---|---|---|---|---|---|---|
| | 1 | 2 | 3 | 4 | 5 | 6 | 7 |
| average error (mm) | 1.348 | 1.312 | 1.371 | 1.521 | 1.233 | 1.170 | 1.444 | the values in Table 3. This indicates that the spatial intersection procedure is accurately recovering the coordinates in the world coordinate system. The model fitting errors are largest when the spatial intersection data set is farthest from the calibration data set.

TABLE 6

Average magnitude of the model fitting error (in mm) for each calibration trial (rows) and each measured data set (columns).

| trial | 1 | 2 | 3 | 4 | 5 | 6 | 7 |
|---|---|---|---|---|---|---|---|
| 1 | 0.154 | 0.405 | 0.271 | 0.207 | 0.322 | 0.285 | 0.298 |
| 2 | 0.389 | 0.245 | 0.445 | 0.337 | 0.246 | 0.428 | 0.392 |
| 3 | 0.335 | 0.613 | 0.296 | 0.367 | 0.490 | 0.307 | 0.437 |
| 4 | 0.205 | 0.379 | 0.312 | 0.187 | 0.298 | 0.297 | 0.248 |
| 5 | 0.408 | 0.301 | 0.476 | 0.349 | 0.280 | 0.451 | 0.374 |
| 6 | 0.324 | 0.564 | 0.273 | 0.355 | 0.455 | 0.245 | 0.424 |
| 7 | 0.295 | 0.475 | 0.308 | 0.247 | 0.366 | 0.292 | 0.233 |

Table 7 shows the intrinsic parameters for the system obtained from each trial. The camera scale factors obtained during calibration agree with the nominal value of 2200 pixels/mm. In addition, the camera principal point is consistent with the nominal value of (255,255) pixels. The shear coefficient is small with respect to $s_c^x$ (0.14%), suggesting a very small contribution. The scale factor for the projector is close to the nominal value of 120 stripes/mm.

TABLE 7

The 6 intrinsic parameters for the camera (upper) and the 3 intrinsic parameters for the projector (lower) for each calibration trial.

| | trial | | | | | | |
|---|---|---|---|---|---|---|---|
| | 1 | 2 | 3 | 4 | 5 | 6 | 7 |
| $s_c^x$ | 2411.062 | 2399.667 | 2425.255 | 2418.480 | 2403.901 | 2443.054 | 2408.316 |
| $s_c^y$ | 2412.349 | 2402.982 | 2425.084 | 2421.023 | 2407.875 | 2445.911 | 2410.448 |
| $c_c^x$ | 289.389 | 283.201 | 301.069 | 274.053 | 271.295 | 314.980 | 272.129 |
| $c_c^y$ | 271.802 | 303.288 | 258.478 | 275.559 | 309.616 | 261.080 | 259.293 |
| $k_c$ | 4.211 | 2.316 | 4.308 | 3.285 | 1.938 | 4.006 | 3.136 |
| $K_c$ | 0.464 | 0.176 | 0.449 | 0.439 | 0.200 | 0.219 | 0.035 |
| $s_p^x$ | 899.157 | 1020.565 | 1151.871 | 1015.006 | 1061.455 | 1162.614 | 1059.352 |
| $c_p^x$ | 159.906 | 240.831 | 130.128 | 183.441 | 223.480 | 132.600 | 181.811 |
| $K_p$ | 0.085 | 0.123 | 0.317 | 0.116 | 0.138 | 0.384 | 0.409 |

Given the observed data for a trial and the calibration parameters for that trial (or any other), special intersection can be used to estimate the coordinates of the fiducial marks in the world coordinate system established by the calibration. These can be compared with the reference coordinates by estimating, using (for non-limiting example) a least squares error criterion, the 3D rigid body transformation needed to transform the reference coordinates to the estimated coordinates (model fitting). The model fitting error is the difference between the estimated world coordinates and the transformed reference coordinates. Table 6 shows the average magnitude of the model fitting error for all of the calibration trials and all of the observed data sets. The diagonal entries of Table 6 are very close to, and less than, However, there are significant variations in many of the parameters. An examination of the estimated dispersion matrix for the camera shows some parameters have high variances and there are high correlations between parameters. This can be partially explained by the experimental configuration of the structured light system; with the distance between the camera and the world reference much larger than the diameter of the world reference a weak perspective camera model provides a reasonable explanation of the observed data. Consequently many parameters are correlated. In particular, has a relatively large variance and is highly correlated with $s_c^x$ and $s_c^y$.

The above remarks are also applicable to the projector parameters. However, the situation for eh projector is inherently worse than that for the camera as the projector has nine parameters (compared to 12 for the camera) but only half as many data points are available. As described above, introducing $K_p$ allows $T_p^2$ to be estimated, but, as expected, it has a large variance. Furthermore, when the distance between the projector and the world reference is much larger than the diameter of the world reference, the stripe planes are nearly parallel in the working volume. Hence a component of the rotation is nearly unidentifiable. This gives rise to large variances in the rotation parameters.

It is important to note that the actual values of the camera and projector parameters are incidental in this situation and it is the values of the measured 3D coordinates that are of interest. Therefore, including $T_p^2$ and $K_p$ in the projector model is useful because it improves the accuracy of the spatial data, even though $T_p^2$ is not particularly accurate.

In preferred embodiments, optical fibers are used to transmit the modulated light through the endoscope to the region of interest, so that the effective area of the projector is minimized.

In preferred embodiments, calibration of the system is carried out when the system is produced. Preferably, no recalibration is needed. However, if recalibration is needed, it can be carried out on site, even in the operating theater.

In preferred embodiments, a standard camera can be used, with positioning of the camera field of view controlled by positioning the endoscope.

A further advantage of the system of the present invention is that standard systems can be used to transmit the modulated light to the region of interest, for example, through the endoscope or laparoscope, or through a thoracostomy.

In preferred embodiments of the system, a standard endoscope is used. In preferred embodiments, the light source is a laser; the location from which the light enters the working area can be altered so as to produce the stripe pattern needed for reconstruction disclosed above.

In some embodiments using the reconstruction method disclosed above, the axis of the wide-angle lens is not parallel to the plane formed by the stripe pattern since as described above, reconstruction is not possible when a ray between the camera focal point and the object point (parallel to the axis of the lens) is parallel to the plane originating at the projector focal point and passing through the object point (the plane formed by the stripe pattern).

In some embodiments of the system, in addition to live-streaming the images, the system can capture still images and store them in a database.

In some embodiments, the light source can be at least one spectral range selected from a group consisting of the visible, near infrared, infrared, or ultraviolet spectral regions.

Image transmission can be by using any of wireless communication, transmission of optical signals through fiber optic cables, or transmission of electrical signals through wires or cables.

The light source can be a laser, Light Emitting Diodes (LED's) or any other source known in the art. Preferably the illumination is in substantially the same spectral range as that to which the camera is sensitive.

In some embodiments, display of the 3D scene can be by any conventional 3D display means such as, but not limited to, a 3D screen, 3D glasses, autostereoscopy, holography, a volumetric display, integral imaging, wiggle stereoscopy, an active shutter 3d system, a polarized 3d system, an interference filter system, a color anaglyph systems a Chromadepth system, an over/under format, and any combination thereof.

In preferred embodiments, the operating tools can be detected using depth cues.

In some embodiments, structures such as blood vessels, nerves, or certain limbs can be detected by the system. In preferred variants of such embodiments, the detected structures can be emphasized by any means known in the art such as, but not limited to, virtual reality overlays, color markings, pattern markings, outlines, arrows, and any combination thereof.

In some embodiments, data from other modalities such as, but not limited to, CT, Mill, ultrasound, PET and any combination thereof can be displayed to the surgeon. Preferably, the endoscope image and the image(s) from the other modalit(ies) are matched to and aligned with each other in 3D, so that the display includes all of the image information.

In some embodiments, additional information such as recommendations useful in directing the progress of an operation, information useful in assisting an operator in making a decision, information useful for a record of the operation and any combination thereof can be displayed to the surgeon, either visually or audibly. This additional information can be, but is not limited to, camera pose, body temperature, time, elapsed time since start of operation, patient notes, notes made during the operation, and other information accessible to the system and any combination thereof.

Color Modulation

Figure 22:
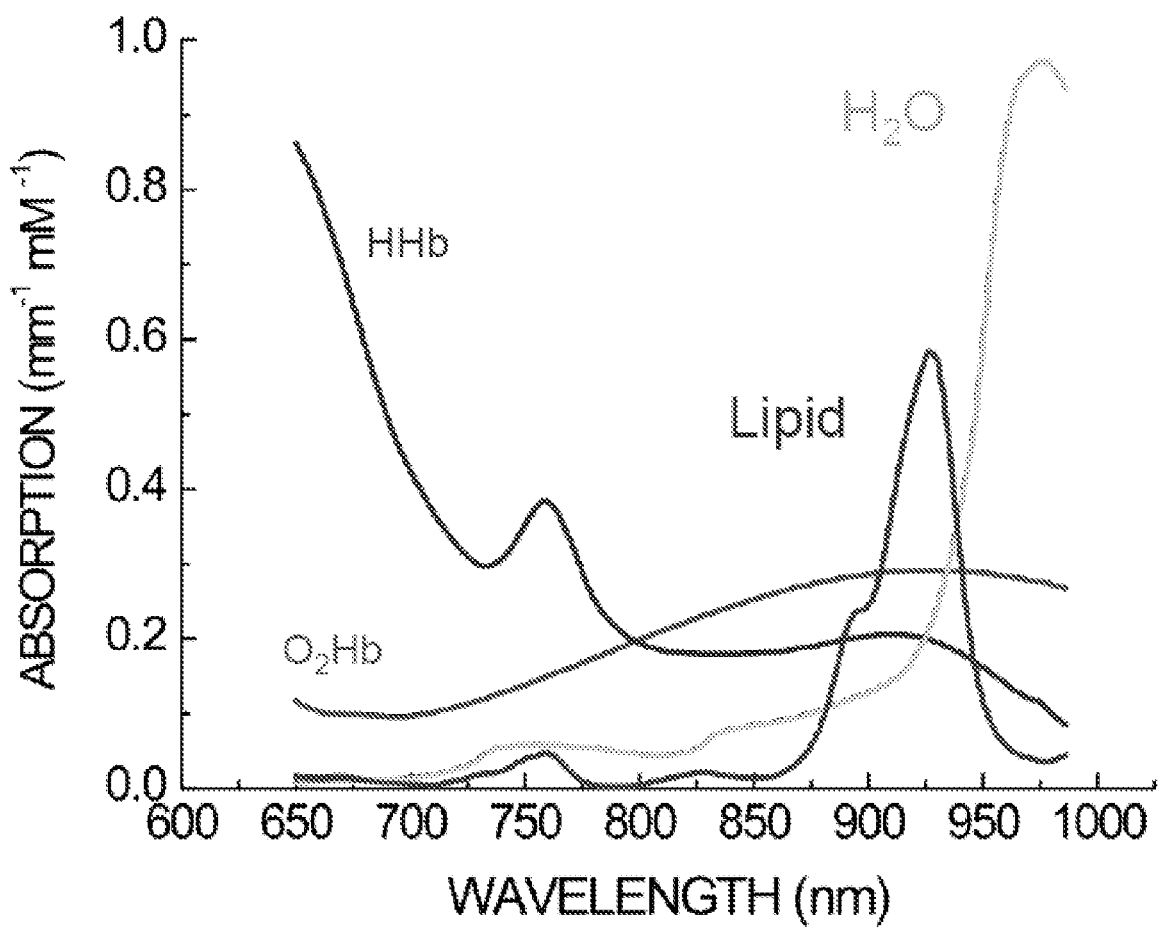
FIG. 22 shows absorption of light by substances found in tissue.

Color modulation can be used to distinguish different types of tissue, since different types of tissue show different patterns of scattering and absorption at different wavelengths due to the different fractions of e.g., lipids, deoxyhemoglobin (HHb), oxyhemoglobin ($O_2$Hb) and water in the tissues. FIG. 22 shows absorption patterns for lipids, deoxyhemoglobin (HHb), oxyhemoglobin ($O_2$Hb) and water as a function of wavelength for wavelengths from about 650 nm to about 1000 nm.

Color modulation can be used to identify hemodynamics and vascular reactivity, aiding in diagnosis of cancerous tissue and vascular disease. For non-limiting example, in vascular disease, the restricted blood flow to the tissue results in ischemia, hypoxia and tissue necrosis, all identifiable by increased HHb and decreased $O_2$Hb.

Figure 23:
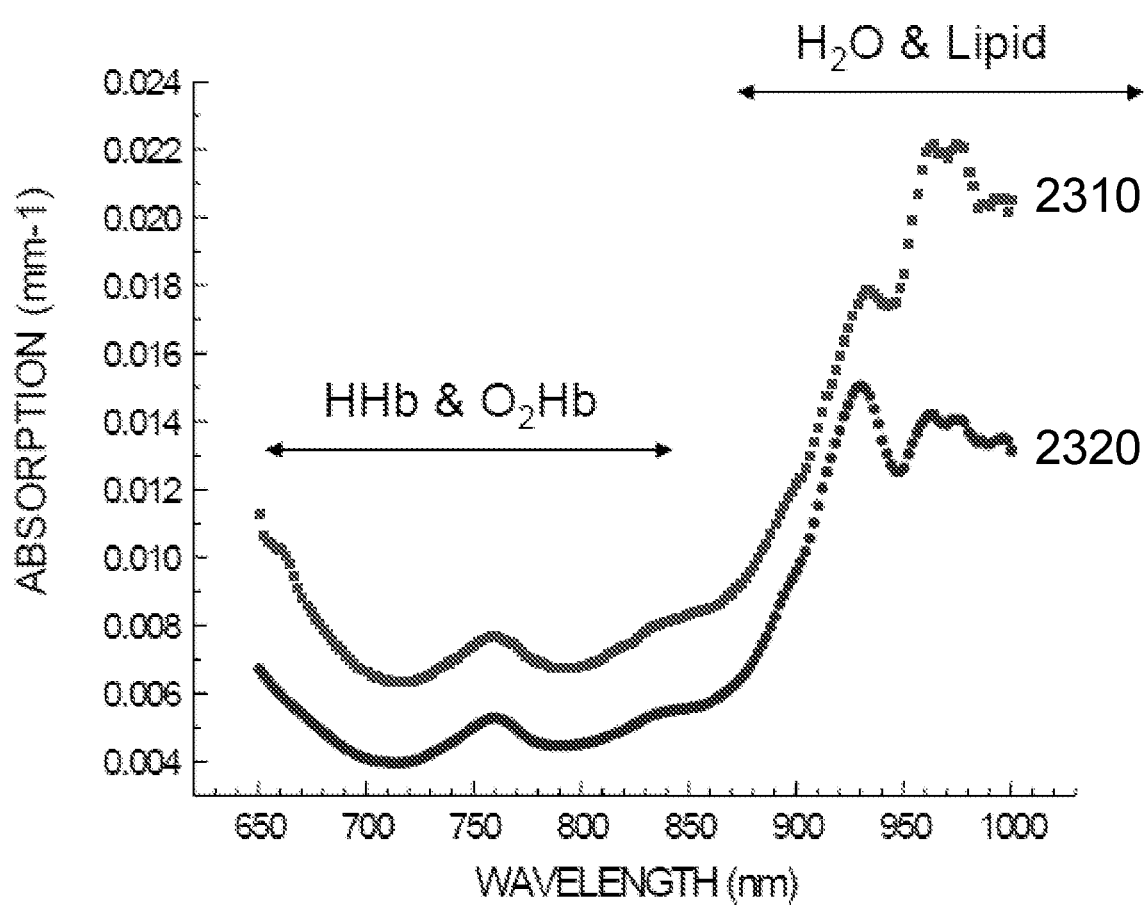
FIGS. 23-25 show absorption of light by tissue at different wavelengths

An example of the difference between normal tissue and cancerous tissue is shown in FIG. 23, in which, for 58 subjects, the absorption pattern for normal (2320) and cancerous (2310) breast tissue is compared. The absorption pattern between about 650 nm and 850 nm is primarily due to HHb and $O_2$Hb, whereas the absorption pattern between about 850 nm and about 1000 nm is primarily due to $H_2O$ and lipids.

Figure 24:
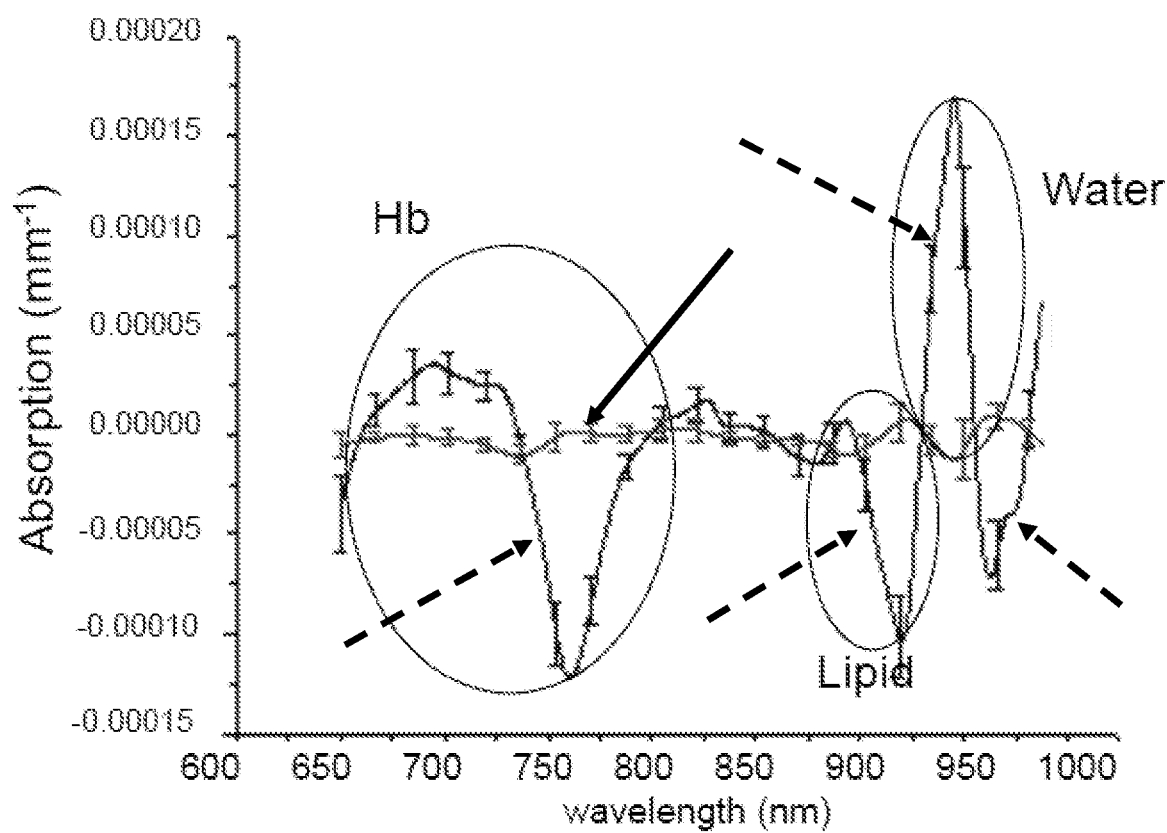

FIG. 24 shows the difference between cancerous (dashed arrows) and normal tissue (solid arrows) for 65 subjects. The curve for the normal subjects is nearly flat, while the curve for the cancerous tissue shows a peak and trough characteristic of Hb, a lipid trough and water peak.

Figure 25:
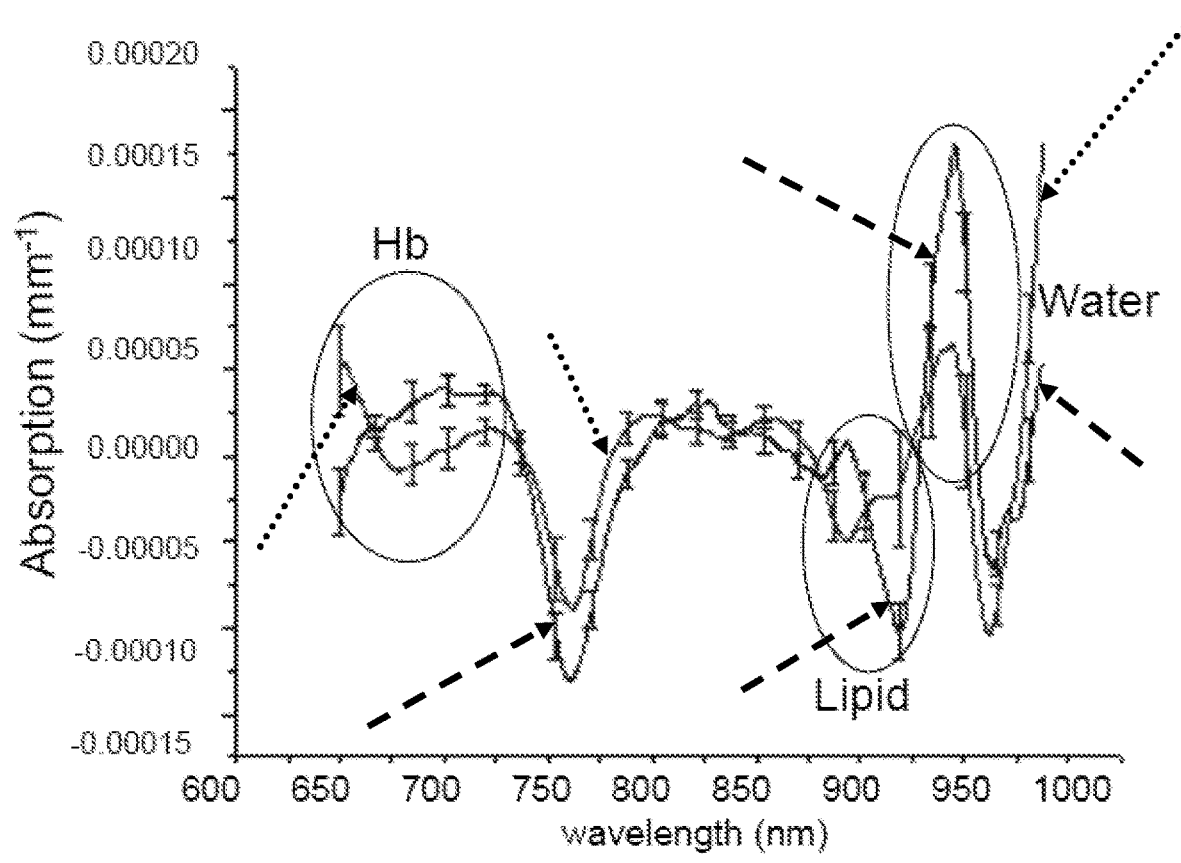

FIG. 25 shows the difference between cancerous (dashed arrows) and fibroadenomous tissue (dotted arrows) for 40 subjects. The peak and trough characteristic of Hb, the lipid trough and the water peak are significantly larger for the cancerous than the fibroadenomous tissue.

Control of the Field of View

In preferred embodiments of the present system, the system comprises all the mechanisms required to control fully the movement of both the movement of and the articulation of an articulated endoscope so that the position of the endoscope and the position and angle of the tip of the endoscope are fully under control.

In preferred embodiments, movement of the endoscope and control of the articulation of the endoscope are fully automatic; the surgeon indicates a desired location and/or field of view and the endoscope movements and articulation changes needed to achieve the desired location and/or field of view are carried out, while avoiding collisions with the tools and\or the tissue, without need for further input from the operator.

Such control can be by means of a touchscreen, a joystick, voice commands, eye movements, hand movements, or other control means under the command of a surgeon.

Figure 26A:
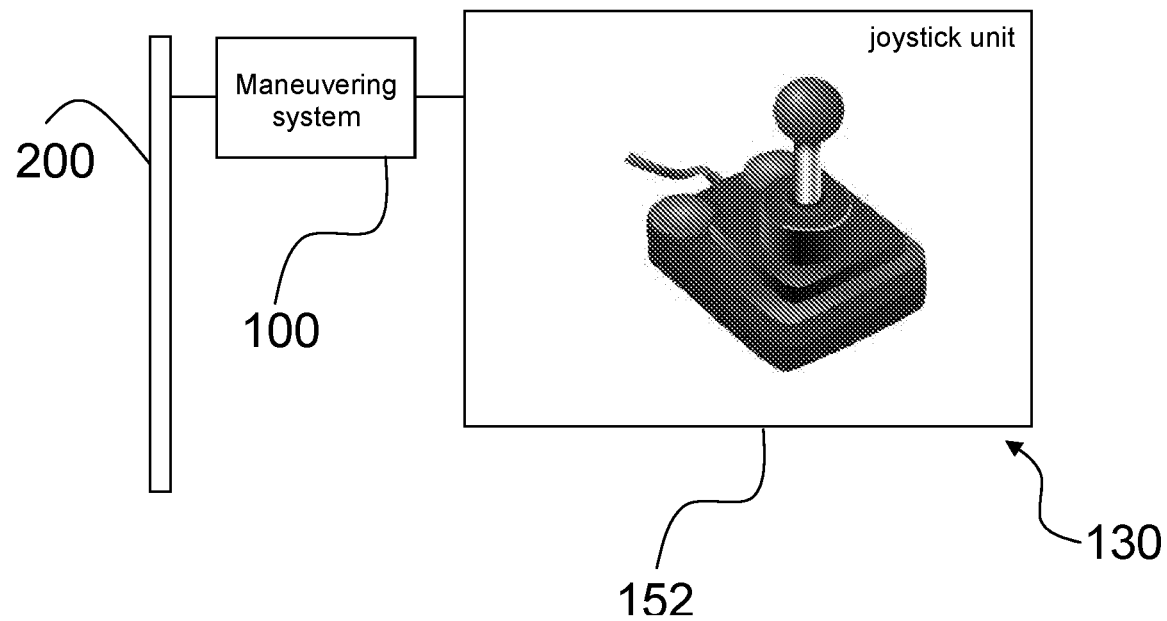
FIGS. 26-27 schematically illustrate joystick units.
Figure 26B:
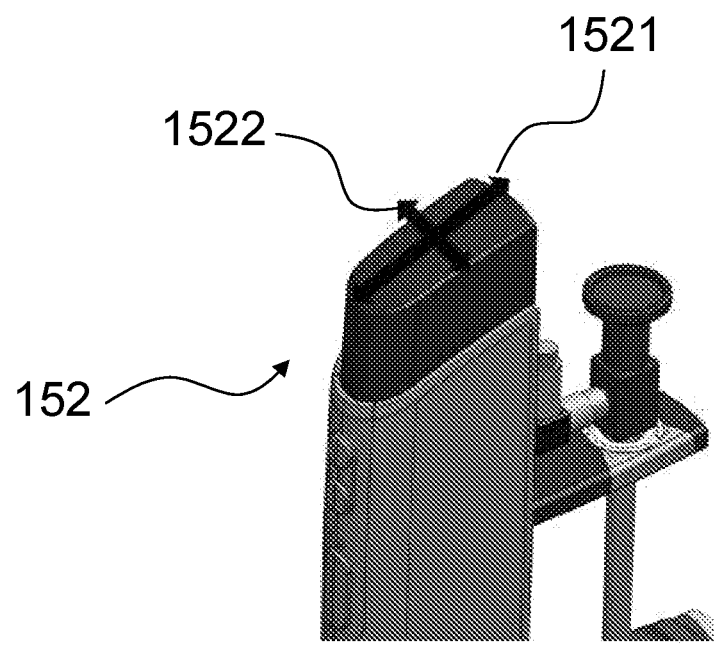

Reference is now made to FIGS. 26a and 26b, which present in a non-limiting manner a system for maneuvering an endoscope (SFME) 130 according to the present invention.

The system for maneuvering an endoscope 130 comprises at least one joystick unit 152 and at least one communication means. At least one of the at least one communication means is adapted to connect at least one joystick unit 152 to any standard maneuvering system 100 for maneuvering an endoscope 200. Different joystick units can control different aspects of the endoscope's motion. For non-limiting example, a joystick unit to control lateral movement of the endoscope, a joystick unit to control zooming and a joystick unit to control articulation of the endoscope tip. Preferably, a single joystick controls all aspects of motion.

The communication means can comprise a wireless communication means, a wired communication means and any combination thereof.

The connection between the joystick unit 152 and the maneuvering system 100 (or other control system) enables control of the maneuvering system 100 by the joystick unit 152, thereby enabling an operator to control the movement of the endoscope 200 by controlling the joystick unit 152.

Furthermore, the communication means is adapted to disconnect the joystick unit 152 from the maneuvering system 100, thereby preventing the endoscope 200 from being moved by the joystick unit 152. Disconnection of the joystick unit 152 prevents the situation of unwanted movement of the endoscope 200 due to inadvertent joystick unit 152 motion. Thus, in such a situation, movement of the joystick unit 152 will not result in movement of the endoscope 120.

FIG. 26b illustrates a closer view of the joystick unit 152. Upon pressing the joystick unit 152 in the direction of arrow 1521, the endoscope moves forward or backward. Upon pressing the joystick unit 152 in the direction of arrow 1522, the endoscope moves left or right.

In preferred embodiments, movement of the endoscope is proportional to movement of the joystick unit, unless the speed of the endoscope tip in a given direction would be above a predetermined value. In these embodiments, movement of the endoscope at speeds greater than the predetermined value is prevented. In these variants of the preferred embodiments, if a speed above the predetermined value is commanded, the endoscope will continue moving, but with a speed at or just below the predetermined value. In some embodiments, if a speed above the predetermined value is commanded, movement of the endoscope is prevented.

According to some embodiments of the present invention, the SFME 130 can be wearable, either by a user or by an instrument. Reference is now made to FIGS. 27a-27d which depict, in a non-limiting manner, a wearable operator. FIGS. 27a and 27b depict the at least one joystick unit 152 mounted in a operator 150, here a ring wearable by a user, while FIG. 27c depicts the at least one joystick unit 152 mounted on a operator 150 attached to an exemplary surgical instrument and FIG. 27d depicts a operator 150 to be held in the hand. The operator 150 can be attached to any surgical instrument, can be attached to or mounted on the endoscope, or, as shown in FIG. 27d, can be a free-standing unit which can sit on, for example, the operating table, a side table or stand, or on a hospital bed.

Referring again to FIGS. 27a-d, FIGS. 27a and 27c depict embodiments of operator 150 with a single joystick unit 152, while FIGS. 27b and 27d depict embodiments of the operator with two joystick units 152. In preferred embodiments of devices such as FIGS. 27a and 27c with a single joystick unit, the joystick unit 152 controls maneuvering of the endoscope. In less-preferred embodiments, the joystick unit controls zoom of the endoscope. In embodiments of the operator 150 such as FIGS. 27b and 27d with two joystick units, one joystick unit 152 controls maneuvering of the endoscope, while the other joystick unit 152 controls zoom of the endoscope.

Referring again to FIGS. 27a-27b, according to some embodiments, the wearable operator 150 is adjustable by means of flexible and stretchable silicone and/or rubber strip 154 and a loop-closing means 156. The loop-closing means 156 is adapted to close a loop with the flexible and stretchable strip. Together, the flexible and stretchable strip and the loop-closing means are provided so as to fit the wearable operator to at least one selected from a group consisting of (a) said predetermined location of said different instruments; (b) said predetermined body part of said surgeon, each of which is characterized by a different size and shape.

As will be disclosed hereinafter, the loop-closing means 156 can be e.g., a unidirectional catch, a rack, a peg or any other mechanism known in the art.

According to some embodiments, the silicone and/or rubber strip 154 is passed through a unidirectional catch (e.g., ratchet 156), such that, when the physician wears the wearable operator 150, he adjusts the same by pulling the silicone and/or rubber strip 154 through the ratchet 156.

According to some embodiments, the silicone and/or rubber strip 154 is rotated around rack or peg 156 such that, when the physician wears the wearable operator 150, he adjusts the same by pulling the silicone and/or rubber strip 154 around the peg 156.

According to this embodiment, the silicone and/or rubber strip 154 is characterized by a varied width along its length. More specifically, at least a portion of the silicone and/or rubber strip 154 is characterized by a greater width, such that when the same is twisted/rotated around peg 156 and reaches the wider portion, the same is fixedly secured to the wearable operator 150.

According to some embodiments, the silicone and/or rubber strip 154 is characterized by different surface roughnesses along its length. More specifically, at least a portion of the silicone and/or rubber strip 154 is characterized by e.g., an abrasive or rough surface such that when the same is twisted/rotated around peg 156 and reaches the rougher portion, the same is fixedly secured to the wearable operator 150.

Referring again to FIG. 27c illustrating an embodiment of the wearable operator 150 attached to a surgical tool via fastener 155. Some embodiments of fastener 155 are shown in FIGS. 27e-27i.

According to the embodiment shown in FIG. 27e, the wearable operator 150 comprises a unidirectional coupling (e.g., ratchet 1510).

Once the wearable operator 150 is secured to the surgical tool, the wearable operator 150 is adjusted to the size and dimensions of the surgical tool by means of a unidirectional catch (e.g., ratchet 1510).

According to some embodiments, the wearable operator 150 comprises a body having at least two portions 1520 and 1521 (see FIG. 27*f*). Said portions are adapted to 'grasp' the surgical tool such that when the wearable operator 150 is coupled to the surgical tool, fine-tuned movement of the two body portions is obtainable so as to provide said tight-fit coupling between said two portions and said instrument.

According to some embodiments (FIG. 27*g*), one of the two portions (either 1520 or 1521) is rotationally movable relative to the other, such that when said wearable operator is coupled to said instrument, fine-tuned movement of said two body portions is obtainable so as to provide said tight-fit coupling between said two portions and said instrument.

According to some embodiments (FIG. 27*h*), the two portions (1521 and 1520) are rotationally movable relative to each other, such that when the wearable operator is coupled to said instrument, fine-tuned movement of said two body portions is obtainable so as to provide said tight-fit coupling between said two portions and said instrument.

In reference to FIG. 27*h*, the movement of either portion 1520 or portion 1521 relative to the other is obtained by fixating the position of either portion 1520 or portion 1521 and coupling the other portion to e.g., a unidirectional catch (e.g., ratchet) 1510 or a two-way directional catch 1510 on the body of the wearable operator.

Figure 27I:
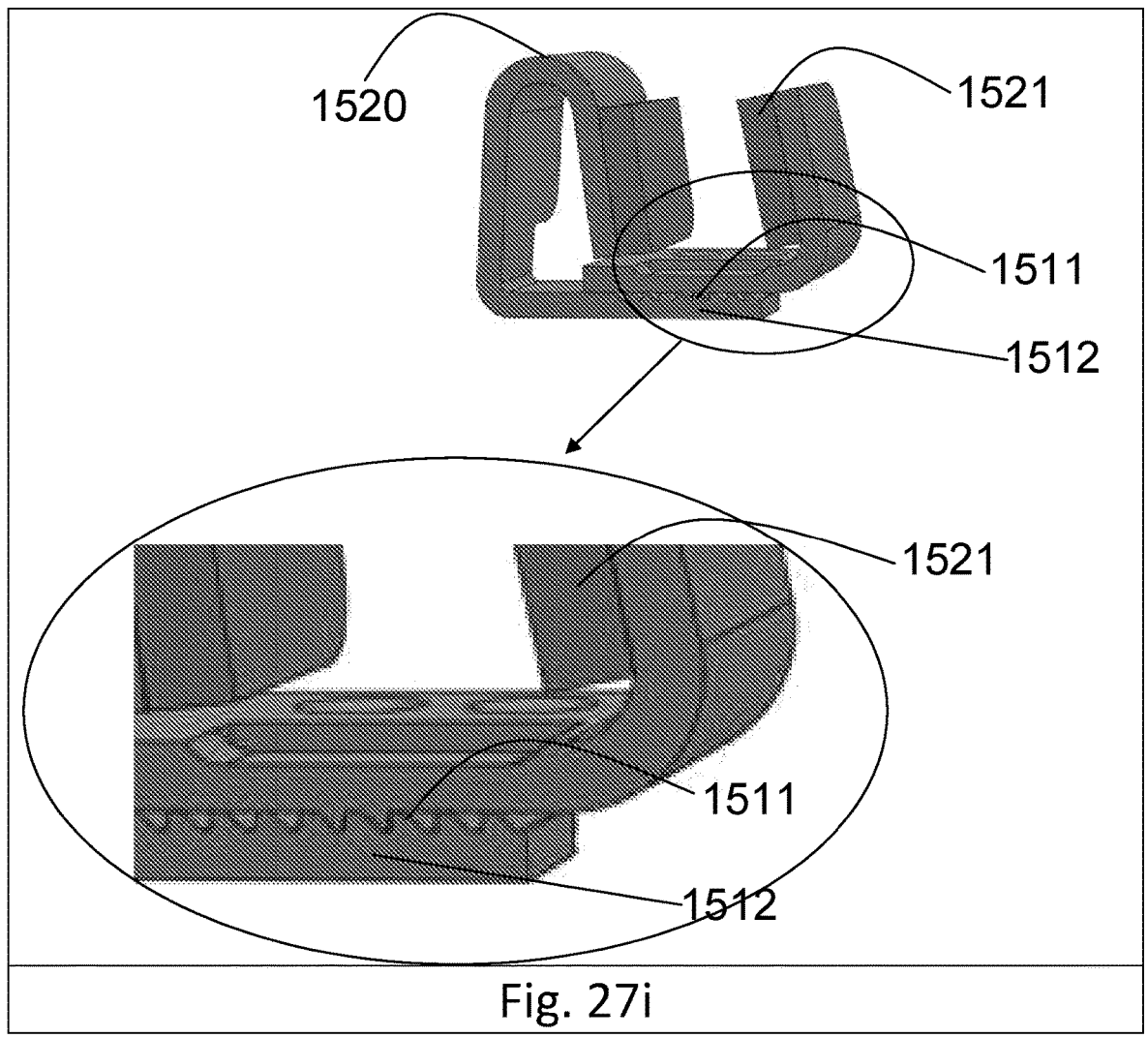

According to some embodiments, the movement of either portion 1520 or portion 1521 relative to the other is obtained by providing one portion, e.g., portion 1521 with cog-like teeth 1511 and the body of the wearable operator with cog-like teeth 1512 matching with cog-like teeth 1511 (see FIG. 27*i*). In such a way portion 1521 can be linearly moved relative to portion 1520.

Referring again to FIG. 27*d*, this embodiment of operator 150 depicts joystick unit 152*a*, which controls maneuvering of the endoscope, comprising a force joystick, while joystick unit 152*b*, which controls zooming, comprises a pressable button. Button 156 is an emergency off button; pressing button 156 quickly stops all motion. Light 158 is a fault light, illuminating when a fault is detected in the system.

In some embodiments, a single control is used for both lateral maneuvering of the endoscope and zooming of the endoscope. In some variants of these embodiments, lateral movement of the joystick unit or lateral movement of a hand on the joystick unit is translated into lateral maneuvering of the endoscope, for non-limiting example, as described above for FIG. 26*b*, while pressure on the joystick unit, either continuous pressure or clicking the joystick unit, is translated into zooming of the endoscope, as described hereinbelow.

In some embodiments, two joystick units are used, one for lateral maneuvering of the endoscope, and one for zooming.

In some embodiments, two joystick units are used, one for maneuvering, both lateral maneuvering and zoom, and the other for directing the endoscope to focus on a desired tool. In these embodiments, on the display screen showing the field of view of the endoscope, a symbol indicates the tool on which the endoscope is focused. This symbol can be a shape or it can be highlighting. When a user clicks on the second joystick unit, the new tool to be focused on is indicated, either by moving the symbol or highlighting to the new tool, or by a second symbol or a second color of highlighting. The user can repeat clicking until the desired tool is indicated. In some embodiments, ceasing to click on the second joystick unit indicates that the current tool is the desired tool; in some embodiments, a longer pressure on the second joystick unit indicates that the current tool is the desired tool. Once the desired too has been selected, the endoscope redirects to the desired tool.

Operation of the zoom mechanism can be by clicking on a joystick unit or by a continuous pressure on a joystick unit. Some non-limiting examples of embodiments of methods of zoom control include:

1. A single click to select zoom in, a double click to select zoom out, and continuous pressure to zoom at a predetermined rate in the selected direction.
2. A double click to select zoom in, a single click to select zoom out, and continuous pressure to zoom in the selected direction.
3. A single click to change the direction of zoom and continuous pressure to zoom at a predetermined rate in the selected direction.
4. A single click to change the direction of the zoom, a double click to zoom by a predetermined amount in the selected direction.
5. A double click to change the direction of the zoom, a single click to zoom by a predetermined amount in the selected direction.
6. A single click to change the direction of zoom and a double click to zoom by a predetermined amount in the selected direction.
7. A single click to change the direction of zoom, a double click to zoom by a predetermined amount in the selected direction, and continuous pressure to zoom at a predetermined rate in the selected direction.

In embodiments in which continuous pressure is used to zoom in the selected direction, in some variants of these embodiments, continuous pressure above a predetermined minimum pressure (a minimum which can be zero) zooms the endoscope at a predetermined zoom rate. In other variants of embodiments in which continuous pressure is used to zoom in the selected direction, if the pressure is above a predetermined minimum pressure, which can be zero, the greater the pressure, the greater the zoom rate, until a predetermined maximum rate is reached, above which the zoom rate is the predetermined maximum rate.

In embodiments wearable by the user, the operator 150 can be worn as a ring on a finger; as a wristband on the wrist; an armband on an arm; on the chest, either supported around the chest or supported around the neck; or on the head, supported by a headband, by a helmet or by a helmet frame.

The communication means connecting the maneuvering system to the operator 150 can be a wireless communication means, a wired communication means, and any combination thereof.

In some embodiments of the current invention, SFME 130 additionally comprises, in a non-limiting manner, means for controlling movement of endoscope 200 adapted to restrain the endoscope's velocity.

In some embodiments of the current invention, SFME 130 additionally comprises, in a non-limiting manner, n sensors, where n is an integer greater than or equal to one. The sensors may be adapted to activate in case of power failure or to activate when connected to power. The sensors are selected in a non-limiting manner from a group consisting, for example, of motion sensors, heat sensors, electric sensors, sound sensors, pressure sensors, optical sensors, and any combination thereof.

In some embodiments of the current invention, joystick unit 152 is characterized in a non-limiting manner by an external surface.

In some embodiments of the current invention, at least one motion sensor detects motion of joystick unit 152. Furthermore, detection of motion is used for deactivation of the motion of endoscope 200 if the requested speed of the motion is above a predetermined threshold.

In some embodiments of the current invention, at least one motion sensor detects, in a non-limiting manner, motion on the external surface of joystick unit 152. Furthermore, endoscope 200 then moves in response to the motion on the external surface of joystick unit 152. Additionally, detection of motion above a predetermined threshold speed on joystick unit 152 will deactivate motion of endoscope 200.

In some embodiments of the current invention, at least one heat sensor is adapted in a non-limiting manner to sense temperatures in the range of about 35 to about 42 degrees. The at least one heat sensor is adapted to sense whether a human hand/fingers are activating (i.e., touching) the joystick unit 152.

Furthermore, at least one heat sensor enables in a non-limiting manner the activation of SFME 130 when the at least one heat sensor senses temperatures in the range of about 35 to about 42 degrees.

Additionally, at least one heat sensor is adapted in a non-limiting manner to provide a thermal image, where the at least one heat sensor is coupled to a processing unit adapted to provide the endoscope user with the thermal image, and a processing unit enables the activation of SFME 130 upon analysis of the image and detection of human hand.

In some embodiments of the current invention, at least one electric sensor is adapted in a non-limiting manner to detect, for example, a power failure, the electric conductivity of the subject's body, and any combination thereof. Additionally, the conductivity of the subject's body sensed by the at least one electric sensor enables the activation of the SFME.

In some embodiments of the current invention, at least one sound sensor is adapted in a non-limiting manner to sense predetermined sound patterns. Furthermore, the predetermined sound patterns sensed by the at least one sound sensor enables the activation of SFME 130.

Additionally, at least one sound sensor is used to operate endoscope 200 according to predetermined sound patterns (e.g., the human voice, predetermined movement commands).

In some embodiments of the current invention, at least one pressure sensor is adapted in a non-limiting manner to sense pressure applied to SFME 130.

Additionally, in some embodiments, the pressure sensed by the at least one pressure sensor is used to activate SFME 130. In some embodiments, when the pressure sensed by the at least one pressure sensor is above a predetermined threshold, SFME 130 is activated. In some embodiments, when the pressure sensed by the at least one pressure sensor is below a predetermined threshold, SFME 130 is de-activated. In some embodiments, when the pressure sensed by the at least one pressure sensor is below a predetermined threshold, SFME 130 is activated.

An example of pressure above a pre-determined threshold activating SFME 130 is a pressure sensor in the joystick unit, which is activated when the pressure of a hand or fingers or an appropriated implement is sensed. SFME 130 would be deactivated if the above pressure was below a pre-determined threshold.

An example of pressure above a pre-determined threshold de-activating SFME 130 is a joystick unit where pressure is used to set the speed of motion of a scalpel. If the pressure is above the pre-determined threshold, the scalpel would move too rapidly, so SFME 130 is de-activated if pressures above the pre-determined threshold are sensed. SFME 130 would then be activated if pressures are below a pre-determined threshold.

In some embodiments of the current invention, at least one optical sensor is adapted in a non-limiting manner to sense visual changes according to predetermined visual patterns. Furthermore, the at least one optical sensor enables the activation of SFME 130 according to predetermined visual patterns. Additionally, at least one optical sensor is used to operate endoscope 200 according to predetermined visual patterns.

In some embodiments, SFME 130 is adapted to sense power failure by any means known in the art, including the sensors described herein. In some embodiments, SFME 130 responds to power failure by instructing the maneuvering system to keep the endoscope and any other controlled instruments in the position and at the angle held by them immediately before the power failure. In some embodiments, the system further comprises means by which the endoscope can be manually switched to manual control in the event of power failure, so that the operation can continue safely with an operating assistant maneuvering the endoscope during the period of power failure.

In some embodiments, the system comprises battery backup such that, in the event of power failure, the system switches automatically to battery power, enabling the SFME to continue to control movement of the endoscope during power outages.

In some embodiments, a standard articulating endoscope, such as the Stryker™ articulating endoscope is used. In some embodiments, an integral articulating endoscope is used.

According to some embodiments of the present invention, the surgical controlling system comprises the following components:
  a. at least one surgical tool adapted to be inserted into a surgical environment of a human body for assisting a surgical procedure, at least one said tool being an articulating tool;
  b. at least one location estimating means adapted to real-time estimate/locate the location (i.e., the 3D spatial position) of the at least one surgical tool at any given time t;
  c. at least one movement detection means communicable with a movement-database and with said location estimating means; said movement-database is adapted to store said 3D spatial position of said at least one surgical tool at time $t_f$ and at time $t_0$; where $t_f > t_0$; said movement detection means is adapted to detect movement of said at least one surgical tool if the 3D spatial position of said at least one surgical tool at time $t_f$ is different than said 3D spatial position of said at least one surgical tool at time $t_0$; and,
  d. a controller having a processing means communicable with a database, the controller adapted to control the spatial position of the at least one surgical tool.

The initial time $t_0$ can be the beginning of the surgical procedure, it can be the time at which the tool entered the body, it can be the time at the beginning of the current movement, or it can be the previous timestep in the current maneuver. In preferred embodiments, the processor will reset to as necessary during the surgical procedure. For non-limiting example, the difference in position between the location of the tool at the previous timestep and its location at the current timestep can be used to calculate the tool's current velocity while the difference in position between its current position and its position at the start of the current maneuver can be used to calculate the tool's overall direction of motion.

The location of the tool can be the location of the tool's tip, the location of a predetermined point on the tool's body, or the location of a predetermined point on the tool's handle. The position defining the location of the tool can be changed as needed, e.g., from the location of the body to the location of the tip.

In some embodiments, the surgical controlling system additionally comprises a touchscreen adapted to accept input of a location within the body, that location indicated by pressure on the portion of the touchscreen showing the image of the location.

In order to facilitate control, a number of motion control rules have been implemented, as described hereinbelow.

It is within the scope of the present invention that the database is adapted to store a predetermined set of rules according to which ALLOWED and RESTRICTED movements of the at least one surgical tool are determined, such that the spatial position of the at least one surgical tool is controlled by the controller according to the ALLOWED and RESTRICTED movements. In other words, each detected movement by said movement detection means of said at least one surgical tool is determined as either an ALLOWED movement or as a RESTRICTED movement according to said predetermined set of rules.

Thus, the present invention stores the 3D spatial position of each surgical tool at a current at time $t_f$ and at time $t_0$; where $t_f > t_0$. If the 3D spatial position of said at least one surgical tool at time $t_f$ is different than said 3D spatial position of said at least one surgical tool at time $t_0$ movement of the tool is detected. Next the system analyses said movement according to said set of rule and process whether said movement is ALLOWED movement or RESTRICTED movement.

According to one embodiment of the present invention, the system prevents said movement, if said movement is a RESTRICTED movement. Said movement prevention is obtained by controlling a maneuvering system which prevents the movement of said surgical tool.

According to one embodiment of the present invention, the system does not prevent said movement, (if said movement is a RESTRICTED movement), but merely signals/alerts the user (i.e., the physician) of said RESTRICTED movement.

According to some embodiments of the present invention, said surgical tool is an endoscope.

According to some embodiments of the present invention, the controller may provide a suggestion to the operator as to which direction the surgical tool has to move to or may be moved to.

Thus, according to a preferred embodiment of the present invention, the present invention provides a predetermined set of rules which define what is an "ALLOWED movement" of any surgical tool within the surgical environment and what is a "RESTRICTED movement" of any surgical tool within the surgical environment.

According to some embodiments the system of the present invention comprises a maneuvering subsystem communicable with the controller, the maneuvering subsystem is adapted to spatially reposition the at least one surgical tool during surgery according to the predetermined set of rules.

According to some embodiments, the controller may provide instructions to a maneuvering subsystem for spatially repositioning the location of the surgical tool. According to these instructions, only ALLOWED movements of the surgical tool will be performed. Preventing RESTRICTED movements is performed by: detecting the location of the surgical tool; processing all current rules; analyzing the movement of the surgical tool and preventing the movement if the tool's movement is a RESTRICTED movement.

According to some embodiments, system merely alerts the physician of a RESTRICTED movement of at least one surgical tool (instead of preventing said RESTRICTED movement).

Alerting the physician of RESTRICTED movements (or, alternatively preventing a RESTRICTED movement) is performed by: detecting the location of the surgical tool; processing all current rules; analyzing the movement of the surgical tool and informing the surgeon (the user of the system) if the tool's movement is an ALLOWED movement or a RESTRICTED movement.

Thus, according to a preferred embodiment of the present invention, if RESTRICTED movements are prevented, the same process (of detecting the location of the surgical tool; processing all current rules and analyzing the movement of the surgical tool) is followed except for the last movement, where the movement is prevented if the tool's movement is a RESTRICTED movement. The surgeon can also be informed that the movement is being prevented.

According to some embodiment, the above (alerting the physician and/or preventing the movement) is performed by detecting the location of the surgical tool and analyzing the surgical environment of the surgical tool. Following analysis of the surgical environment and detection of the location of the surgical tool, the system may assess all the risks which may follow a movement of the surgical tool in the predetermined direction. Therefore, each location in the surgical environment has to be analyzed so that any possible movement of the surgical tool will be classified as an ALLOWED movement or a RESTRICTED movement.

According to one embodiment of the present invention, the location of each tool is determined using image processing means and determining in real-time what is the 3D spatial location of each tool. It should be understood that the above mentioned "tool" may refer to the any location on the tool. For example, it can refer to the tip of the same, the body of the same and any combination thereof.

In some embodiments, avoidance of body organs is facilitated by means of a proximity sensor on the circumference of at least one tool. In these embodiments, if the distance between the tool and another object in the surgical environment, such as, but not limited to, an organ or another tool, is less than a predetermined distance, the proximity sensor activates, thereby notifying the control system that at least one tool is too close to another object in the surgical environment.

In some variants of embodiments with proximity sensors, the proximity sensor not only determined whether an object is within a predetermined distance of the sensor, it also determines, for objects within the predetermined distance, the distance between the sensor and the object.

Hereinbelow, determination of the 3D location of each tool includes determination by means of a proximity sensor as well as determination by means of image processing.

The predetermined set of rules which are the essence of the present invention are adapted to take into consideration all the possible factors which may be important during the surgical procedure. The predetermined set of rules may comprise the following rules or any combination thereof:

a. a route rule;
b. an environment rule;

c. an operator input rule;
d. a proximity rule;
e. a collision prevention rule;
f. a history based rule;
g. a tool-dependent ALLOWED and RESTRICTED movements rule.
h. a most used tool rule;
i. a right tool rule;
j. a left tool rule;
k. a field of view rule;
l. a no fly zone rule;
m. a preferred volume zone rule;
n. a preferred tool rule;
o. a movement detection rule, and
p. a tagged tool rule.

Thus, for example, the collision prevention rule defines a minimum distance below which two or more tools should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a RESTRICTED movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to any skilled in the art (e.g., image processing, optical means etc.).

The following provides explanations for each of the above mentioned rules and its functions:

According to some embodiments, the route rule comprises a predefined route in which the at least one surgical tool is adapted to move within the surgical environment; the ALLOWED movements are movements in which the at least one surgical tool is located within the borders of the predefined route, and the RESTRICTED movements are movements in which the at least one surgical tool is located out of the borders of the predefined route. Thus, according to this embodiment, the route rule comprises a communicable database storing at least one predefined route in which the at least one surgical tool is adapted to move within the surgical environment; the predefined route comprises n 3D spatial positions of the at least one surgical tool in the route; n is an integer greater than or equal to 2; ALLOWED movements are movements in which the at least one surgical tool is located substantially in at least one of the n 3D spatial positions of the predefined route, and RESTRICTED movements are movements in which the location of the at least one surgical tool is substantially different from the n 3D spatial positions of the predefined route.

In other words, according to the route rule, each of the surgical tool's courses (and path in any surgical procedure) is stored in a communicable database. ALLOWED movements are defined as movements in which the at least one surgical tool is located substantially in at least one of the stored routes; and RESTRICTED movements are movements in which the at least one surgical tool is in a substantially different location than any location in any stored route.

According to some embodiments, the environmental rule is adapted to determine ALLOWED and RESTRICTED movements according to hazards or obstacles in the surgical environment as received from an endoscope or other sensing means. Thus, according to this embodiment, the environmental rule comprises a comprises a communicable database; the communicable database is adapted to received real-time images of the surgical environment and is adapted to perform real-time image processing of the same and to determine the 3D spatial position of hazards or obstacles in the surgical environment; the environmental rule is adapted to determine ALLOWED and RESTRICTED movements according to hazards or obstacles in the surgical environment, such that RESTRICTED movements are movements in which at least one surgical tool is located substantially in at least one of the 3D spatial positions, and ALLOWED movements are movements in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. RESTRICTED movements are defined as movements in which the at least one surgical tool is located substantially in the same location as that of the hazards or obstacles; and the ALLOWED movements are movements in which the location of the at least one surgical tool is substantially different from that of all of the hazards or obstacles.

According to some embodiments, hazards and obstacles in the surgical environment are selected from a group consisting of tissues, surgical tools, organs, endoscopes and any combination thereof.

According to some embodiments, the operator input rule is adapted to receive an input from the operator of the system regarding the ALLOWED and RESTRICTED movements of the at least one surgical tool. In other words, the operator input rule receives instructions from the operator of the system as to what can be regarded as ALLOWED movements and what are RESTRICTED movements.

According to some embodiments, the input comprises n 3D spatial positions; n is an integer greater than or equal to 2; wherein at least one of which is defined as an ALLOWED location and at least one of which is defined as a RESTRICTED location, such that the ALLOWED movements are movements in which the at least one surgical tool is located substantially in at least one of the n 3D ALLOWED spatial positions, and the RESTRICTED movements are movements in which the location of the at least one surgical tool is substantially different from the n 3D ALLOWED spatial positions.

According to some embodiments, the input comprises at least one rule according to which ALLOWED and RESTRICTED movements of the at least one surgical tool are determined, such that the spatial position of the at least one surgical tool is controlled by the controller according to the ALLOWED and RESTRICTED movements.

According to some embodiments, the operator input rule can convert an ALLOWED movement to a RESTRICTED movement and a RESTRICTED movement to an ALLOWED movement.

According to some embodiments, the proximity rule is adapted to define a predetermined distance between the at least one surgical tool and at least one another surgical tool; the ALLOWED movements are movements which are within the range or out of the range of the predetermined distance, and the RESTRICTED movements which are out of the range or within the range of the predetermined distance; the ALLOWED movements and the RESTRICTED movements are defined according to different ranges. Thus, according to this embodiment, the proximity rule is adapted to define a predetermined distance between at least two surgical tools. In a preferred embodiment, the ALLOWED movements are movements which are within the range of the predetermined distance, while the RESTRICTED movements which are out of the range of the predetermined distance. In another preferred embodiment, the ALLOWED movements are movements which are out of the range of the predetermined distance, while the RESTRICTED movements are within the range of the predetermined distance It should be pointed out that the above mentioned distance can be selected from the following:
- (a) the distance between the tip of the first tool and the tip of the second tool;
- (b) the distance between the body of the first tool and the tip of the second tool;
- (c) the distance between the body of the first tool and the body of the second tool; and
- (d) the distance between the tip of the first tool and the body of the second tool; and any combination thereof.

According to some embodiments, the proximity rule is adapted to define a predetermined angle between at least three surgical tools; ALLOWED movements are movements which are within the range or out of the range of the predetermined angle, and RESTRICTED movements are movements which are out of the range or within the range of the predetermined angle.

According to some embodiments, the collision prevention rule is adapted to define a predetermined distance between the at least one surgical tool and an anatomical element within the surgical environment (e.g. tissue, organ, another surgical tool or any combination thereof); the ALLOWED movements are movements which are in a range that is larger than the predetermined distance, and the RESTRICTED movements are movements which is in a range that is smaller than the predetermined distance.

According to some embodiments, the anatomical element is selected from a group consisting of tissue, organ, another surgical tool or any combination thereof.

According to some embodiments, the surgical tool is an endoscope. The endoscope is adapted to provide real-time images of the surgical environment.

According to some embodiments, the right tool rule is adapted to determine the ALLOWED movement of the endoscope according to the movement of a surgical tool in a specified position in relation to the endoscope, preferably positioned to right of the same. According to this rule, the tool which is defined as the right tool is constantly tracked by the endoscope. According to some embodiments, the right tool is defined as the tool positioned to the right of the endoscope; according to some embodiments, any tool can be defined as the right tool. An ALLOWED movement, according to the right tool rule, is a movement in which the endoscope field of view is moved to a location substantially the same as the location of the right tool, thereby tracking the right tool. A RESTRICTED movement, according to the right tool rule, is a movement in which the endoscope field of view is moved to a location substantially different from the location of the right tool.

According to some embodiments, the left tool rule is adapted to determine the ALLOWED movement of the endoscope according to the movement of a surgical tool in a specified position in relation to the endoscope, preferably positioned to left of the same. According to this rule, the tool which is defined as the left tool is constantly tracked by the endoscope. According to some embodiments, the left tool is defined as the tool positioned to the left of the endoscope; according to some embodiments, any tool can be defined as the left tool. An ALLOWED movement, according to the left tool rule, is a movement in which the endoscope field of view is moved to a location substantially the same as the location of the left tool. A RESTRICTED movement, according to the left tool rule, is a movement in which the endoscope field of view is moved to a location substantially different from the location of the left tool.

According to some embodiments, the field of view rule is adapted to define a field of view and maintain that field of view. The field of view rule is defined such that if the endoscope is adapted to track a predetermined set of tools in a desired field of view, when one of those tools is no longer in the field of view, the rule instructs the endoscope to zoom out so as to reintroduce the tool into the field of view. Thus, according to this embodiment, the field of view rule comprises a communicable database comprising n 3D spatial positions; n is an integer greater than or equal to 2; the combination of all of the n 3D spatial positions provides a predetermined field of view; the field of view rule is adapted to determine the ALLOWED movement of the endoscope within the n 3D spatial positions so as to maintain a constant field of view, such that the ALLOWED movements are movements in which the endoscope is located substantially in at least one of the n 3D spatial positions, and the RESTRICTED movements are movements in which the location of the endoscope is substantially different from the n 3D spatial positions.

Thus, according to some embodiments of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spatial locations of the same, where m is an integer greater than or equal to 1 and where a tool can be a surgical tool, an anatomical element and any combination thereof. The combination of all of the n 3D spatial positions provides a predetermined field of view. The field of view rule is adapted to determine ALLOWED movement of the endoscope such that the m 3D spatial positions of the tools comprise at least one of the n 3D spatial positions of the field of view, and RESTRICTED movements are movements in which the 3D spatial position of at least one tool is substantially different from the n 3D spatial positions of the field of view.

According to some embodiments, the preferred volume zone rule comprises a communicable database comprising n 3D spatial positions; n is an integer greater than or equal to 2; the n 3D spatial positions provides the preferred volume zone; the preferred volume zone rule is adapted to determine the ALLOWED movement of the endoscope within the n 3D spatial positions and RESTRICTED movement of the endoscope outside the n 3D spatial positions, such that the ALLOWED movements are movements in which the endoscope is located substantially in at least one of the n 3D spatial positions, and the RESTRICTED movements are movements in which the location of the endoscope is substantially different from the n 3D spatial positions. In other words, the preferred volume zone rule defines a volume of interest (a desired volume of interest), such that an ALLOWED movement, according to the preferred volume zone rule, is a movement in which the endoscope (or any surgical tool) is moved to a location within the defined preferred volume. A RESTRICTED movement, according to the preferred volume zone rule, is a movement in which the endoscope (or any surgical tool) is moved to a location outside the defined preferred volume.

According to some embodiments, the preferred tool rule comprises a communicable database, the database stores a preferred tool; the preferred tool rule is adapted to determine the ALLOWED movement of the endoscope according to the movement of the preferred tool. In other words, the preferred tool rule defines a preferred tool (i.e., a tool of interest) that the user of the system wishes to track. An ALLOWED movement, according to the preferred tool rule, is a movement in which the endoscope is moved to a location substantially the same as the location of the preferred tool. A RESTRICTED movement is a movement in which the endoscope is moved to a location substantially different from the location of the preferred tool. Thus, according to the preferred tool rule the endoscope constantly tracks the preferred tool, such that the field of view, as seen from the endoscope, is constantly the preferred tool. It should be noted that the user may define in said preferred tool rule to constantly track the tip of said preferred tool or alternatively, the user may define in said preferred tool rule to constantly track the body or any location on the preferred tool.

According to some embodiments, the no fly zone rule is adapted to define a RESTRICTED zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is adapted to determine a RESTRICTED movement if the movement is within the no fly zone and an ALLOWED movement if the movement is outside the no fly zone, such that RESTRICTED movements are movements in which the at least one surgical tool is located substantially in at least one of the n 3D spatial positions, and the ALLOWED movements are movements in which the location of the at least one surgical tool is substantially different from the n 3D spatial positions.

According to some embodiments, the most used tool rule is adapted to define (either real-time, during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is adapted to constantly position the endoscope to track the movement of the surgical tool with the largest number of movements. In some embodiments of the most used tool rule, the communicable database measures the amount of movement of each of the surgical tools; the most used tool rule is adapted to constantly position the endoscope to track the movement of the surgical tool with the largest amount of movement.

According to some embodiments, the system is adapted to alert the physician of a RESTRICTED movement of at least one surgical tool. The alert can be audio signaling, voice signaling, light signaling, flashing signaling and any combination thereof.

According to some embodiments, an ALLOWED movement is one permitted by the controller and a RESTRICTED movement is one denied by the controller.

According to some embodiments, the history-based rule is adapted to determine the ALLOWED and RESTRICTED movements according to historical movements of the at least one surgical tool in at least one previous surgery. Thus, according to this embodiment, the history-based rule comprises a communicable database storing each 3D spatial position of each of the surgical tools, such that each movement of each surgical tool is stored; the history-based rule is adapted to determine ALLOWED and RESTRICTED movements according to historical movements of the at least one surgical tool, such that the ALLOWED movements are movements in which the at least one surgical tool is located substantially in at least one of the 3D spatial positions, and the RESTRICTED movements are movements in which the location of the at least one surgical tool is substantially different from the n 3D spatial positions.

According to some embodiments, the tool-dependent ALLOWED and RESTRICTED movements rule is adapted to determine ALLOWED and RESTRICTED movements according to predetermined characteristics of the surgical tool, where the predetermined characteristics of the surgical tool are selected from a group consisting of: physical dimensions, structure, weight, sharpness, and any combination thereof. Thus, according to this embodiment, the tool-dependent ALLOWED and RESTRICTED movements rule comprises a communicable database; the communicable database is adapted to store predetermined characteristics of at least one of the surgical tools; the tool-dependent ALLOWED and RESTRICTED movements rule is adapted to determine ALLOWED and RESTRICTED movements according to the predetermined characteristics of the surgical tool.

According to these embodiments, the user can define, e.g., the structure of the surgical tool he wishes the endoscope to track. Thus, according to the tool-dependent ALLOWED and RESTRICTED movements rule the endoscope constantly tracks the surgical tool having predetermined characteristics as defined by the user.

According to some embodiments of the present invention, the movement detection rule comprises a communicable database comprising the real-time 3D spatial positions of each surgical tool; said movement detection rule is adapted to detect movement of at least one surgical tool. When a change in the 3D spatial position of that surgical tool is received, ALLOWED movements are movements in which the endoscope is re-directed to focus on the moving surgical tool.

According to some embodiments of the present invention, the tagged tool rule comprises means of tagging at least one surgical tool within the surgical environment such that, by maneuvering the endoscope, the endoscope is constantly directed to the tagged surgical tool. Thus, according to the tagged tool rule, the endoscope constantly tracks the preferred (i.e., tagged) tool, such that the field of view, as seen from the endoscope, is constantly maintained on the preferred (tagged) tool. It should be noted that the user can define the tagged tool rule to constantly track the tip of the preferred (tagged) tool, the body of the preferred (tagged) tool, or any other location on the preferred (tagged) tool.

According to some embodiments of the present invention, the system further comprises a maneuvering subsystem communicable with the controller. The maneuvering subsystem is adapted to spatially reposition the at least one surgical tool during a surgery according to the predetermined set of rules.

According to some embodiments, the at least one location estimating means is at least one endoscope adapted to acquire real-time images of a surgical environment within the human body for the estimation of the location of at least one surgical tool.

According to some embodiments, the location estimating means comprise at least one selected from a group consisting of optical imaging means, radio frequency transmitting and receiving means, at least one mark on at least one surgical tool and any combination thereof.

According to some embodiments, the at least one location estimating means is an interface subsystem between a surgeon and at least one surgical tool, the interface subsystem comprising (a) at least one array comprising N regular light sources or N pattern light sources, where N is a positive integer; (b) at least one array comprising M cameras, where M is a positive integer; (c) optional optical markers and means for attaching the optical markers to at least one surgical tool; and (d) a computerized algorithm operable via the controller, the computerized algorithm adapted to record images received by each camera of each of the M cameras and to calculate therefrom the position of each of the tools, and further adapted to provide automatically the results of the calculation to the human operator of the interface.

It is well known that surgery is a highly dynamic procedure with a constantly changing environment which depends on many variables. A non-limiting list of these variables includes, for example: the type of the surgery, the working space (e.g., with foreign objects, dynamic uncorrelated movements, etc), the type of tools used during the surgery, changing background, relative movements, dynamic procedures, dynamic input from the operator and the history of the patient. Therefore, there is need for a system which is able to integrate all the variables by weighting their importance and deciding to which spatial position the endoscope should be relocated.

The present invention can be also utilized to improve the interface between the operators (e.g., the surgeon, the operating medical assistant, the surgeon's colleagues, etc.). Moreover, the present invention can be also utilized to control and/or direct an automated maneuvering subsystem to focus the endoscope on an instrument selected by the surgeon, or to any other region of interest. This may be performed in order to estimate the location of at least one surgical tool during a surgical procedure.

The present invention also discloses a surgical tracking system which is adapted to guide and relocate an endoscope to a predetermined region of interest in an automatic and/or a semi-automatic manner. This operation is assisted by an image processing algorithm(s) which is adapted to analyze the received data from the endoscope in real time, and to assess the surgical environment of the endoscope.

According to an embodiment, the system comprises a "smart" tracking subsystem, which receives instructions from a maneuvering function f(t) (t is the time) as to where to direct the endoscope and which instructs the maneuvering subsystem to relocate the endoscope to the required area.

The maneuvering function f(t) receives, as input, output from at least two instructing functions $g_i(t)$, analyses their output and provides instruction to the "smart" tracking system (which eventually re-directs the endoscope).

The instructing functions $g_i(t)$ of the present invention are functions which are configured to assess the environment of the endoscope and the surgery, and to output data which guides the tracking subsystem for controlling the spatial position of the maneuvering subsystem and the endoscope. The instructing functions $g_i(t)$ may be selected from a group consisting of:

a. a tool detection function $g_4(t)$;
b. a movement detection function $g_2(t)$;
c. an organ detection function $g_3(t)$;
d. a collision detection function $g_4(t)$;
e. an operator input function $g_5(t)$;
f. a prediction function $g_6(t)$;
g. a past statistical analysis function $g_7(t)$;
h. a most used tool function $g_8(t)$;
i. a right tool function $g_9(t)$;
j. a left tool function $g_{10}(t)$;
k. a field of view function $g_{11}(t)$;
l. a preferred volume zone function $g_{12}(t)$;
m. a no fly zone function $g_{13}(t)$;
n. a proximity function $g_{14}(t)$;
o. a tagged tool function $g_{15}(t)$;
p. a preferred tool function $g_{16}(t)$.

According to some embodiments, each instructing function $g_i(t)$ is also given a weighting function, $\alpha_i(t)$. The purpose of the weighting function is to enable the system to select the instructing function to be executed, if more than one instructing function is activatable at one time.

Thus, for non-limiting example, the maneuvering function f(t) receives input from two instructing functions: the collision detection function $g_4(t)$ (the function providing information whether the distance between two elements is smaller than a predetermined distance) and from the most used tool function $g_8(t)$ (the function counts the number of times each tool is moved during a surgical procedure and provides information as to whether the most moved or most used tool is currently moving). The output given from the collision detection function $g_4(t)$ is that a surgical tool is dangerously close to an organ in the surgical environment. The output given from the most used tool function $g_8(t)$ is that the tool identified statistically as the most moved tool is currently moving.

The maneuvering function f(t) then assigns each of the instructing functions with weighting functions $\alpha_i(t)$. For the above example, the most used tool function $g_8(t)$ is assigned with a greater weight than the weight assigned to the collision detection function $g_4(t)$.

After the maneuvering function f(t) analyses the information received from the instructing functions $g_i(t)$ and the weighting functions $\alpha_i(t)$ of each, the maneuvering function f(t) outputs instructions to the maneuvering subsystem to re-direct the endoscope. (In the above example, the endoscope would be redirected to focus on the moving tool rather than on the tool approaching dangerously close to the organ).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

According to some embodiments, the surgical tracking subsystem comprises:
a. at least one endoscope adapted to acquire real-time images of a surgical environment within the human body;
b. a maneuvering subsystem adapted to control the spatial position of the endoscope during the laparoscopic surgery; and,
c. a tracking subsystem in communication with the maneuvering subsystem, adapted to control the maneuvering subsystem so as to direct and modify the spatial position of the endoscope to a region of interest.

According to this embodiment, the tracking subsystem comprises a data processor. The data processor is adapted to perform real-time image processing of the surgical environment and to instruct the maneuvering subsystem to modify the spatial position of the endoscope according to input received from a maneuvering function f(t); the maneuvering function f(t) is adapted to (a) receive input from at least two instructing functions $g_i(t)$, where i is 1, ..., n and n≥2 and where t is time; i and n are integers; and (b) to output instructions to the maneuvering subsystem based on the input from the at least two instructing functions $g_i(t)$, so as to spatially position the endoscope to the region of interest.

According to one embodiment, the tool detection function $g_1(t)$ is adapted to detect tools in the surgical environment. According to this embodiment, the tool detection function is adapted to detect surgical tools in the surgical environment and to output instructions to the tracking subsystem to instruct the maneuvering subsystem to direct the endoscope to the detected surgical tools.

According to some embodiments, the functions $g_i(t)$ may rank the different detected areas in the surgical environment according to a ranking scale (e.g., from 1 to 10) in which prohibited areas (i.e., areas which are defined as area to which the surgical tools are forbidden to 'enter') receive the lowest score (e.g., 1) and preferred areas (i.e., areas which are defined as area in which the surgical tools should be maintained) receive the highest score (e.g., 10).

According to a preferred embodiment, one function $g_i(t)$ is adapted to detect tools in the surgical environment and inform the maneuvering function f(t) if they are in preferred areas or in prohibited areas.

According to some embodiments, the movement detection function $g_2(t)$ comprises a communicable database comprising the real-time 3D spatial positions of each of the surgical tools in the surgical environment; means to detect movement of the at least one surgical tool when a change in the 3D spatial positions is received, and means to output instructions to the tracking subsystem to instruct the maneuvering subsystem to direct the endoscope to the moved surgical tool.

According to some embodiments, the organ detection function $g_3(t)$ is adapted to detect physiological organs in the surgical environment and to classify the detected organs as prohibited areas or preferred areas. For example, if the operator instructs the system that the specific surgery is kidney surgery, the organ detection function $g_3(t)$ will classify the kidneys (or one kidney, if the surgery is specified to be on a single kidney) as a preferred area and other organs will be classified as prohibited areas. According to some embodiments, the organ detection function is adapted to detect organs in the surgical environment and to output instructions to the tracking subsystem to instruct the maneuvering subsystem to direct the endoscope to the detected organs. According to some embodiments, the right tool function is adapted to detect surgical tool positioned to right of the endoscope and to output instructions to the tracking subsystem to instruct the maneuvering system to constantly direct the endoscope on the right tool and to track the right tool.

According to some embodiments, the left tool function is adapted to detect surgical tool positioned to left of the endoscope and to output instructions to the tracking subsystem to instruct the maneuvering system to constantly direct the endoscope on the left tool and to track the left tool.

According to some embodiments, the collision detection function $g_4(t)$ is adapted to detect prohibited areas within the surgical environment so as to prevent collisions between the endoscope and the prohibited areas. For example, if the endoscope is located in a narrow area in which a precise movement of the same is preferred, the collision detection function $g_4(t)$ will detect and classify different areas (e.g., nerves, veins, walls of organs) as prohibited areas. Thus, according to this embodiment, the collision prevention function is adapted to define a predetermined distance between the at least one surgical tool and an anatomical element within the surgical environment; and to output instructions to the tracking subsystem to instruct the maneuvering subsystem to direct the endoscope to the surgical tool and the anatomical element within the surgical environment if the distance between the at least one surgical tool and an anatomical element is less than the predetermined distance. According to one embodiment of the present invention the anatomical element is selected from a group consisting of tissue, organ, another surgical tool and any combination thereof.

According to some embodiments, the operator input function $g_5(t)$ is adapted to receive an input from the operator. The input can be, for example: an input regarding prohibited areas in the surgical environment, an input regarding allowed areas in the surgical environment, or an input regarding the region of interest and any combination thereof. The operator input function $g_5(t)$ can receive instructions from the operator before or during the surgery, and respond accordingly. According to some embodiments, the operator input function may further comprise a selection algorithm for selection of areas selected from a group consisting of: prohibited areas, allowed areas, regions of interest, and any combination thereof. The selection may be performed via an input device (e.g., a touch screen).

According to some embodiments, the operator input function $g_5(t)$ comprises a communicable database; the communicable database is adapted to receive an input from the operator of the system; the input comprising n 3D spatial positions; n is an integer greater than or equal to 2; and to output instructions to the tracking subsystem to instruct the maneuvering subsystem to direct the endoscope to the at least one 3D spatial position received.

According to some embodiments, the prediction function $g_6(t)$ is adapted to provide data regarding a surgical environment at a time $t_f > t_0$, wherein $t_0$ is the present time and $t_f$ is a future time. The prediction function $g_6(t)$ may communicate with a database which stores data regarding the environment of the surgery (e.g., the organs in the environment). This data may be used by the prediction function $g_6(t)$ for the prediction of expected or unexpected events or expected or unexpected objects during the operation. Thus, according to this embodiment, the prediction function $g_6(t)$ comprises a communicable database storing each 3D spatial position of each of surgical tool within the surgical environment, such that each movement of each surgical tool is stored; the prediction function is adapted to (a) to predict the future 3D spatial position of each of the surgical tools (or each object); and, (b) to output instructions to the tracking subsystem to instruct the maneuvering subsystem to direct the endoscope to the future 3D spatial position.

According to some embodiments, the past statistical analysis function $g_7(t)$ is adapted to provide data regarding the surgical environment or the laparoscopic surgery based on past statistical data stored in a database. The data regarding the surgical environment may be for example: data regarding prohibited areas, data regarding allowed areas, data regarding the region of interest and any combination thereof. Thus, according to this embodiment, the past statistical analysis function $g_6(t)$ comprises a communicable database storing each 3D spatial position of each of surgical tool within the surgical environment, such that each movement of each surgical tool is stored; the past statistical analysis function $g_6(t)$ is adapted to (a) perform statistical analysis on the 3D spatial positions of each of the surgical tools in the past; and, (b) to predict the future 3D spatial position of each of the surgical tools; and, (c) to output instructions to the tracking subsystem to instruct the maneuvering subsystem to direct the endoscope to the future 3D spatial position. Thus, according to the past statistical analysis function $g_7(t)$, the past movements of each tool are analyzed and, according to this analysis, a prediction of the tool's next move is provided.

According to some embodiments, the most used tool function $g_8(t)$ comprises a communicable database counting the amount of movement of each surgical tool located within the surgical environment; the most used tool function is adapted to output instructions to the tracking subsystem to instruct the maneuvering subsystem to direct the endoscope to constantly position the endoscope to track the movement of the most moved surgical tool. The amount of movement of a tool can be defined as the total number of movements of that tool or the total distance the tool has moved.

According to some embodiments, the right tool function $g_9(t)$ is adapted to detect at least one surgical tool in a specified position in relation to the endoscope, preferably positioned to right of the endoscope and to output instructions to the tracking subsystem to instruct the maneuvering subsystem to constantly direct the endoscope to the right tool and to track the same. According to preferred embodiments, the right tool is defined as the tool positioned to the right of the endoscope; according to some embodiments, any tool can be defined as the right tool.

According to some embodiments, the left tool function $g_{10}(t)$ is adapted to detect at least one surgical tool in a specified position in relation to the endoscope, preferably positioned to left of the endoscope and to output instructions to the tracking subsystem to instruct the maneuvering subsystem to constantly direct the endoscope to the left tool and to track the same. According to preferred embodiments, the left tool is defined as the tool positioned to the left of the endoscope; according to other embodiments, any tool can be defined as the left tool.

According to some embodiments, the field of view function $g_{11}(t)$ comprises a communicable database comprising n 3D spatial positions; n is an integer greater than or equal to 2; the combination of all of the n 3D spatial positions provides a predetermined field of view; the field of view function is adapted to output instructions to the tracking subsystem to instruct the maneuvering subsystem to direct the endoscope to at least one 3D spatial position substantially within the n 3D spatial positions so as to maintain a constant field of view.

According to some embodiments, the preferred volume zone function $g_{12}(t)$ comprises a communicable database comprising n 3D spatial positions; n is an integer greater than or equal to 2; the n 3D spatial positions provide the preferred volume zone; the preferred volume zone function $g_{12}(t)$ is adapted to output instructions to the tracking subsystem to instruct the maneuvering subsystem to direct the endoscope to at least one 3D spatial position substantially within the preferred volume zone.

According to some embodiments, the no fly zone function $g_{13}(t)$ comprises a communicable database comprising n 3D spatial positions; n is an integer greater than or equals to 2; the n 3D spatial positions define a predetermined volume within the surgical environment; the no fly zone function $g_{13}(t)$ is adapted to output instructions to the tracking subsystem to instruct the maneuvering subsystem to direct the endoscope to at least one 3D spatial position substantially different from all the n 3D spatial positions.

According to some embodiments, the proximity function $g_{14}(t)$ is adapted to define a predetermined distance between at least two surgical tools; and to output instructions to the tracking subsystem to instruct the maneuvering subsystem to direct the endoscope to the two surgical tools if the distance between the two surgical tools is less than or if it is greater than the predetermined distance.

According to some embodiments, the proximity function $g_{14}(t)$ is adapted to define a predetermined angle between at least three surgical tools; and to output instructions to the tracking subsystem to instruct the maneuvering subsystem to direct the endoscope to the three surgical tools if the angle between the two surgical tools is less than or if it is greater than the predetermined angle.

According to some embodiments, the preferred volume zone function comprises a communicable database comprising n 3D spatial positions; n is an integer greater than or equals to 2; the n 3D spatial positions provides the preferred volume zone; the preferred volume zone function is adapted to output instructions to the tracking subsystem to instruct the maneuvering system to direct the endoscope to the preferred volume zone.

According to some embodiments, the field of view function comprises a communicable database comprising n 3D spatial positions; n is an integer greater than or equals to 2; the combination of all of the n 3D spatial positions provides a predetermined field of view; the field of view function is adapted to output instructions to the tracking subsystem to instruct the maneuvering system to direct the endoscope to at least one 3D spatial position substantially within the n 3D spatial positions so as to maintain a constant field of view.

According to some embodiments, the no fly zone function comprises a communicable database comprising n 3D spatial positions; n is an integer greater than or equals to 2; the n 3D spatial positions define a predetermined volume within the surgical environment; the no fly zone function is adapted to output instructions to the tracking subsystem to instruct the maneuvering system to direct the endoscope to at least one 3D spatial position substantially different from all the n 3D spatial positions.

According to some embodiments, the most used tool function comprises a communicable database counting the amount of movement of each surgical tool located within the surgical environment; the most used tool function is adapted to output instructions to the tracking subsystem to instruct the maneuvering system to direct the endoscope to constantly position the endoscope to track the movement of the most moved surgical tool.

According to some embodiments, the prediction function $g_6(t)$ is adapted to provide data regarding a surgical environment in a time $t_f > t$, wherein t is the present time and $t_f$ is the future time. The prediction function $g_6(t)$ may communicate with a database which stores data regarding the environment of the surgery (e.g., the organs in the environment). This data may be used by the prediction function $g_6(t)$ for the prediction of expected or unexpected events or object during the operation. Thus, according to this embodiment, the prediction function comprises a communicable database storing each 3D spatial position of each of surgical tool within the surgical environment, such that each movement of each surgical tool is stored; the prediction function is adapted to (a) to predict the future 3D spatial position of each of the surgical tools; and, (b) to output instructions to the tracking subsystem to instruct the maneuvering system to direct the endoscope to the future 3D spatial position.

According to some embodiments, the past statistical analysis function $g_7(t)$ is adapted to provide data regarding the surgical environment or the laparoscopic surgery based on past statistical data stored in a database. The data regarding the surgical environment may be for example: data regarding prohibited areas, data regarding allowed areas, data regarding the region of interest. Thus, according to this embodiment, the past statistical analysis function comprises a communicable database storing each 3D spatial position of each of surgical tool within the surgical environment, such that each movement of each surgical tool is stored; the past statistical analysis function is adapted to (a) statistical analyze the 3D spatial positions of each of the surgical tools in the past; and, (b) to predict the future 3D spatial position of each of the surgical tools; and, (c) to output instructions to the tracking subsystem to instruct the maneuvering system to direct the endoscope to the future 3D spatial position. Thus, according to the past statistical analysis function $g_7(t)$, the past movements of each tool are analyzed and according to this analysis a future prediction of the tool's next move is provided.

According to some embodiments, preferred tool function comprises a communicable database, the database stores a preferred tool; the preferred tool function is adapted to output instructions to the tracking subsystem to instruct the maneuvering system to constantly direct the endoscope to the preferred tool, such that said endoscope constantly tracks said preferred tool.

Thus, according to the preferred tool function the endoscope constantly tracks the preferred tool, such that the field of view, as seen from the endoscope, is constantly maintained on said preferred tool. It should be noted that the user may define in said preferred tool function to constantly track the tip of said preferred tool or alternatively, the user may define in said preferred tool function to constantly track the body or any location on the preferred tool.

According to some embodiments, the tagged tool function $g_{15}(t)$ comprises means adapted to tag at least one surgical tool within the surgical environment and to output instructions to the tracking subsystem to instruct the maneuvering subsystem to constantly direct the endoscope to the tagged surgical tool. Thus, according to the tagged tool function, the endoscope constantly tracks the preferred (i.e., tagged) tool, such that the field of view, as seen from the endoscope, is constantly maintained on the preferred (tagged) tool. It should be noted that the user can define the tagged tool function to constantly track the tip of the preferred (tagged) tool, the body of the preferred (tagged) tool, or any other location on the preferred (tagged) tool.

According to some embodiments, the means are adapted to constantly tag at least one surgical tool within the surgical environment.

According to some embodiments, the preferred tool function $g_{16}(t)$ comprises a communicable database. The database stores a preferred tool; and the preferred tool function is adapted to output instructions to the tracking subsystem to instruct the maneuvering subsystem to direct the endoscope to the preferred tool.

According to some embodiments, the system further comprises means adapted to re-tag the at least one of the surgical tools until a desired tool is selected.

According to some embodiments, the system further comprises means adapted to toggle the surgical tools. According to some embodiments, the toggling is performed manually or automatically.

According to some embodiments of the present invention, the weighting functions $\alpha_i(t)$ are time-varying functions (or constants), the value of which is determined by the operator or the output of the instructing functions $g_i(t)$. For example, if a specific function $g_i(t)$ detected an important event or object, its weighting functions $\alpha_i(t)$ may be adjusted in order to elevate the chances that the maneuvering function f(t) will instruct the maneuvering subsystem to move the endoscope towards this important event or object.

According to some embodiments of the present invention, the tracking subsystem may implement various image processing algorithms which may also be algorithms that are well known in the art. The image processing algorithms may be for example: image stabilization algorithms, image improvement algorithms, image compilation algorithms, image enhancement algorithms, image detection algorithms, image classification algorithms, image correlations with the cardiac cycle or the respiratory cycle of the human body, smoke reduction algorithms, vapor reduction algorithms, steam reduction algorithms and any combination thereof. Smoke, vapor and steam reduction algorithms may be needed as it is known that, under certain conditions, smoke, vapor or steam may be emitted by or from the endoscope. The image processing algorithm may also be implemented and used to analyze 2D or 3D representations which may be rendered from the real-time images of the surgical environment.

According to some embodiments, the endoscope may comprise an image acquisition device selected from a group consisting of: a camera, a video camera, an electromagnetic sensor, a computer tomography imaging device, a fluoroscopic imaging device, an ultrasound imaging device, and any combination thereof.

According to some embodiments, the system may also comprise a display adapted to provide input or output to the operator regarding the operation of the system. The display may be used to output the acquired real-time images of a surgical environment with augmented reality elements. The display may also be used for the definition of the region of interest by the operator.

According to some embodiments, the endoscope may be controlled be an endoscope controller for performing operations such as: acquiring the real-time images and zooming-in to a predetermined area. For example, the endoscope controller may cause the endoscope to acquire the real-time images in correlation with the cardiac cycle or the respiratory cycle of a human body.

According to some embodiments, the data processor of the present invention may operate a pattern recognition algorithm for assisting the operation of the instructing functions $g_i(t)$. The pattern recognition algorithm may be used as part of the image processing algorithm.

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

Reference is made now to FIG. 28, which is a general schematic view of an embodiment of a surgical tracking system 100. In this figure are illustrated surgical instruments 17b and 17c and an endoscope 21 which may be maneuvered by means of maneuvering subsystem 19 according to the instructions received from a tracking subsystem operable by computer 15.

According to one embodiment of the present invention as defined in the above, the user may define the field of view function as constantly monitoring at least one of surgical instruments 17b and 17c.

According to this embodiment, the surgical tracking system 100 may also comprise one or more button operated wireless transmitters 12a, which transmit, upon activation, a single code wave 14 through aerial 13 to connected receiver 11 that produces a signal processed by computer 15, thereby directing and modifying the spatial position of endoscope 21 to the region of interest, as defined by the field of view function.

Alternatively, according to the proximity rule, if the distance between the surgical instruments 17b and 17c is smaller than a predetermined distance (as defined by the collision prevention rule), the system alerts the user that any movement of either one of the surgical instruments 17b and 17c that will reduce the distance is a RESTRICTED movement.

FIGS. 29a-b show an embodiment wherein the fine control means is a control mechanism (1830) which attaches to the endoscope (1810). The fine control mechanism attaches to the manual controls (1820) for the articulating endoscope via a connector (1840). In a preferred embodiment, the connector can connect any endoscope control means with any articulating endoscope. FIG. 29a shows the fine control mechanism (1830) before it is attached to the articulating endoscope (1810), while FIG. 29b shows the control mechanism (1830) attached to the articulating endoscope (1810), with the endoscope manual control (1840) connected to the fine control mechanism via the connector (1830).

In some embodiments, such as that shown in FIG. 29, hardware control of the articulation is used, with the current system in effect replacing the surgeon by moving the controls of the articulating tool. In some embodiments, software control is used, with the current system in effect replacing the controls of the articulating tool so that the tool articulates based on commands coming directly from the current system rather than via the tool's manual controls.

Figure 30:
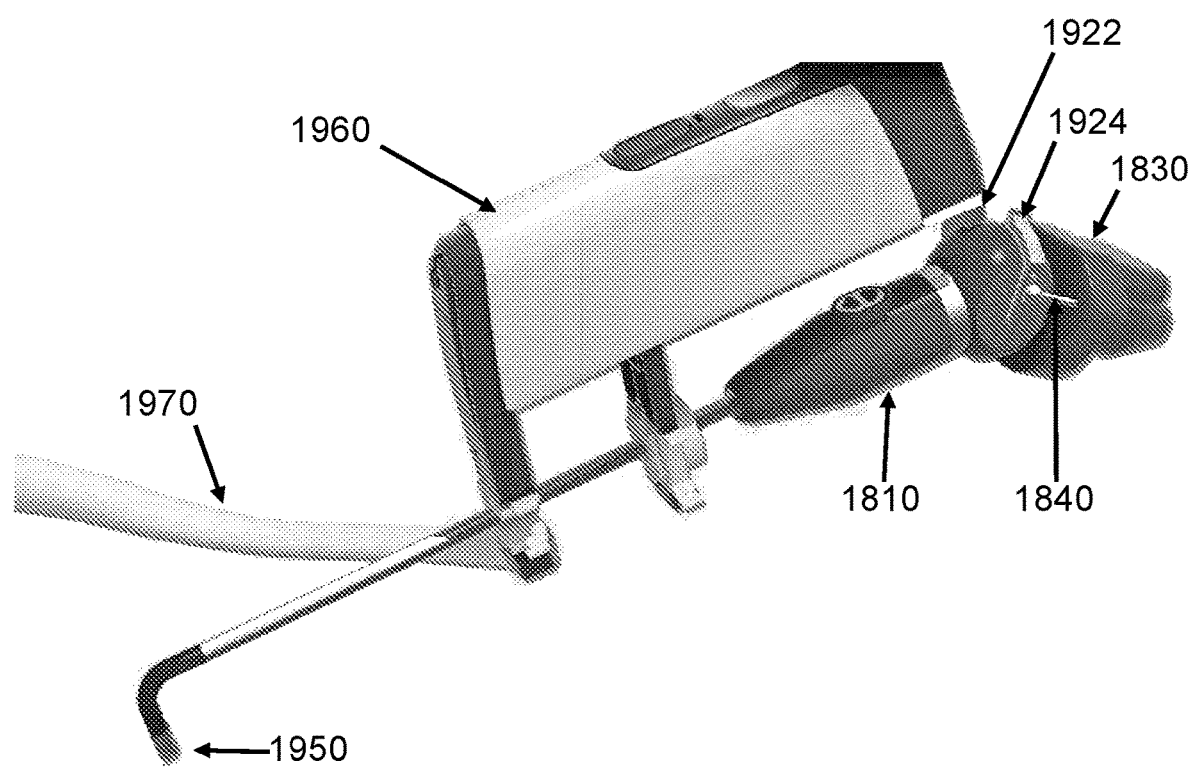
FIG. 30 illustrates the use of the endoscope articulation control.

FIG. 30 shows an embodiment of the articulating endoscope (1810) in use. The endoscope (1810) is attached to the zoom mechanism of the coarse control system (1960), which is attached to the articulating arm (1970) of the coarse control system. The fine control mechanism (1830) is attached to the articulating endoscope (1810) and also enabled to be controlled (either in a wired manner or wirelessly) either automatically by the control system or manually by the endoscope operator. The fine control mechanism (1840) is also connected to the manual controls (1922, 1924) of the articulating endoscope. In this example, one control (1922) is forward and one (1924) is backward, turning the endoscope tip (1950) toward the right of the figure.

Figure 31C:
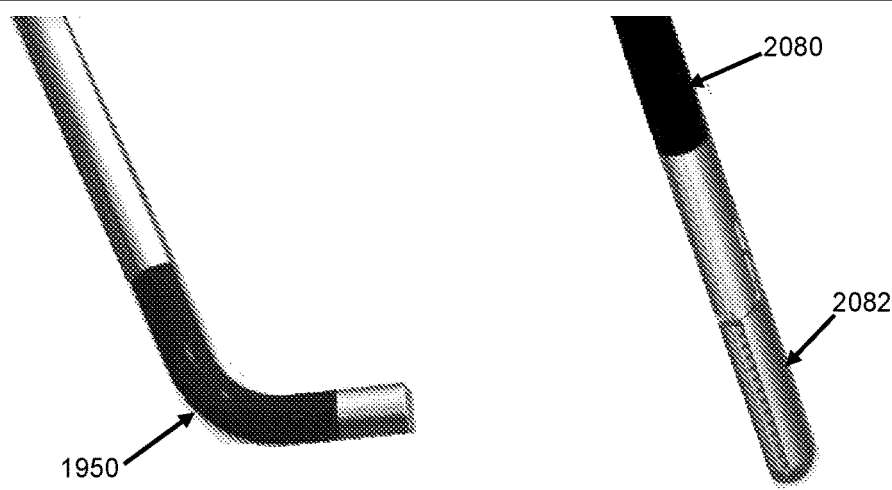
FIG. 31 illustrates articulation of the endoscope.

FIG. 31a-d shows articulation of an embodiment of the articulating endoscope. FIG. 31a illustrates the flexibility of the articulating tip, showing it in typical positions—bent forwards, out of the plane of the paper (1952), to the right (1954), downward (1956), and to the left and backward, into the plane of the paper (1958).

Figure 31D:
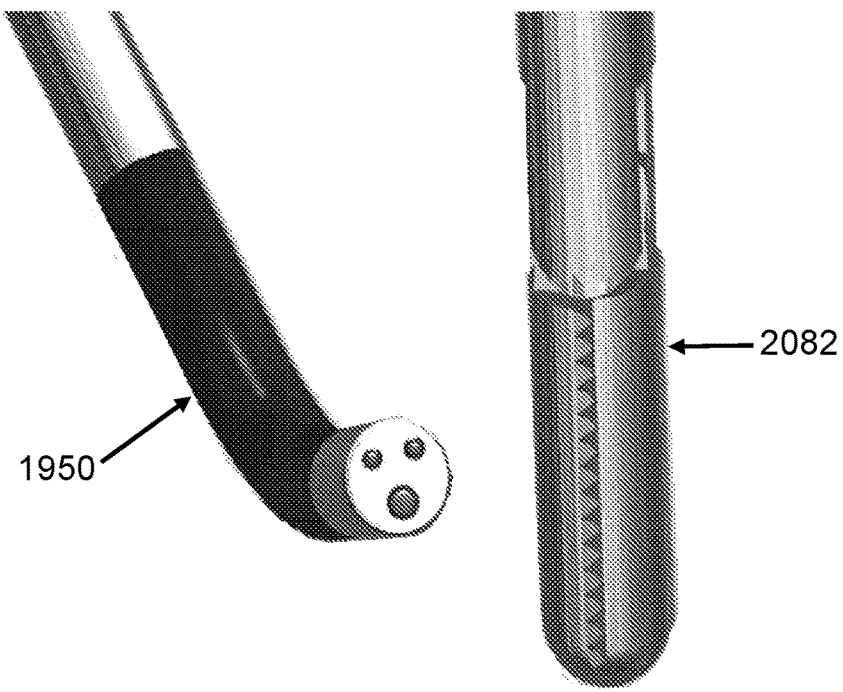

FIGS. 31b-d illustrate the articulating tip (1950) in use, following the movements of the tip (2082) of a medical instrument (2080). In FIG. 31b, the endoscope tip (1950) is straight; it is not yet following the tip of the instrument (2082). In FIG. 31c, the instrument tip (2082) has moved to the right and the tip of the endoscope (1950) has turned right to follow the tip (2082) of the instrument. It can be seen from the angle of the endoscope (1950) that the pivoting point of the endoscope has not changed, although the field of view of the endoscope (1950) has changed significantly. In FIG. 31d, the instrument tip (2082) has moved towards the endoscope and forward, out of the plane of the paper. The tip of the endoscope (1950) has rotated to follow the movement of the instrument tip (2082), but the pivoting point of the endoscope has not changed. It is clear from FIGS. 31a-31d that use of the articulating endoscope allows the surgeon a much larger field of view than would be possible with only movement of an endoscope around the pivoting point. Use of an articulating endoscope also minimizes movement of the whole endoscope relative to the pivoting point, which has the possibility of causing unwanted movement of the pivoting point and, therefore, unwanted movement of the field of view.

EXAMPLES

Examples are given in order to demonstrate embodiments of present invention. The examples describe the manner and process of embodiments of the present invention and set forth the best mode contemplated by the inventors for carrying out the invention, but are not to be construed as limiting the invention.

In the examples below, similar numbers refer to similar parts in all of the figures.

In FIGS. 32-45 in the examples below, for simplicity and clarity, a rigid tool has been illustrated although the rules are equally applicable to both rigid and articulating tools.

Example 1—Tracking System with Collision Avoidance System

One embodiment of such a rule-based system will comprise the following set of commands:
Detection (denoted by Gd):
Gd1 Tool location detection function
Gd2 Organ (e.g. Liver) detection function
Gd3 Movement (vector) calculation and estimation function
Gd4 Collision probability detection function
Tool Instructions (denoted Gt):
Gt1 Move according to manual command
Gt2 Stop movement
The scenario—manual move command by the surgeon:
Locations Gd1(t) and Gd2(t) are calculated in real time at each time step (from an image or location marker).

Tool movement vector Gd3(t) is calculated from Gd1(t) as the difference between the current location and at least one previous location (probably also taking into account previous movement vectors).

The probability of collision—Gd4(t)—is calculated, for example, from the difference between location Gd1 and location Gd2 (the smaller the distance, the closer the proximity and the higher the probability of collision), from movement vector Gd3(t) indicating a collision, etc.

Tool Instructions Gt1 Weight function $\alpha_1(t)=1$ If Gt1(t)<a predetermined threshold and 0 otherwise.

Tool Instructions Gt2 Weight function $\alpha_2(t)=1$ If Gt2(t)>a predetermined threshold and 0 otherwise.

Tool Instructions=$\alpha_1(t)*Gt1+\alpha_2(t)*Gt2(t)$.

In the examples given hereinbelow, the liver will be used as an exemplary organ. The rules can be applied in a similar manner to any identifiable organ or structure in the body.

In reference to FIG. 32, which shows, in a non-limiting manner, an embodiment of a tracking system and collision avoidance system. The system tracks a tool 310 and an organ, in this case a liver 320, in order to determine whether a collision between the tool 310 and the organ 320 is possible within the next time step. FIGS. 32a and 32b show how the behavior of the system depends on the distance 330 between the tool 310 and the organ 320, while FIGS. 32c and 32d show how movement of the tool 310 affects the behavior. In FIG. 32a, the distance 330 between the tool 310 and the organ 320 is large enough that a collision is not possible in that time step. Since no collision is possible, no movement of the tool is commanded. In FIG. 32b, the distance 330 between the tool 310 and the organ 320 is small enough that a collision is likely. In the embodiment illustrated, a movement 340 is commanded to move the tool 310 away from the organ 320. In some embodiments, the system prevents movement 350, but does not command movement 340; in such embodiments, the tool 310 will remain close to the organ 320. In some embodiments, the system warns/signals the operator that the move is RESTRICTED, but does not restrict movement 350 or command movement 340 away from the organ (320). Such a warning/signaling can be visual or aural, using any of the methods known in the art.

Figure 32A:
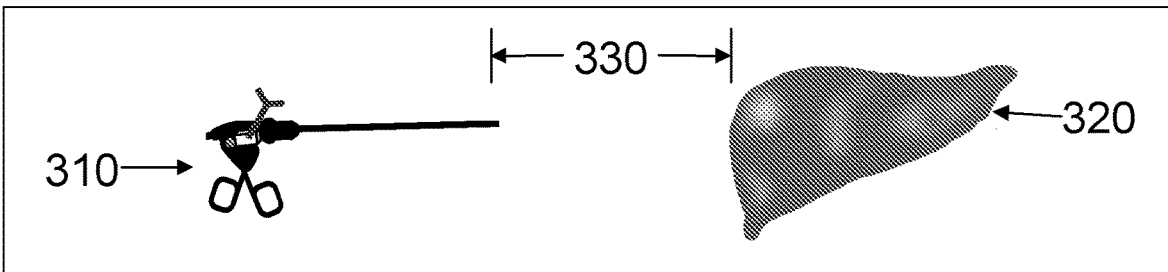
FIG. 32A-D schematically illustrates operation of an embodiment of a tracking system with collision avoidance system.
Figure 32B:
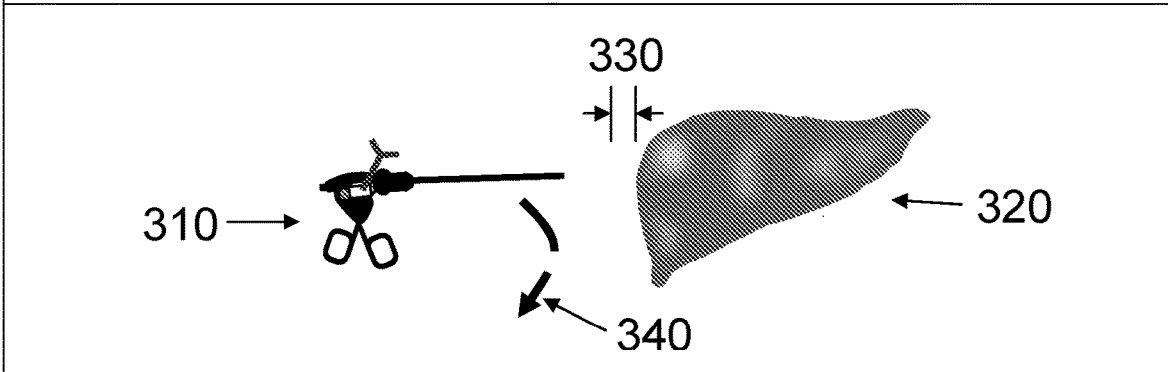
Figure 32C:
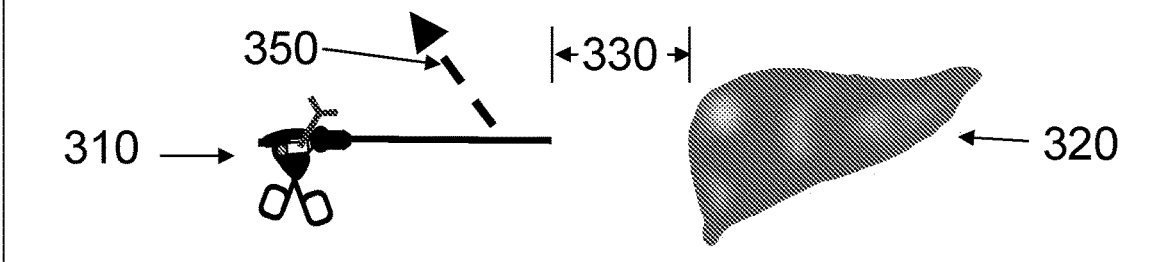
Figure 32D:
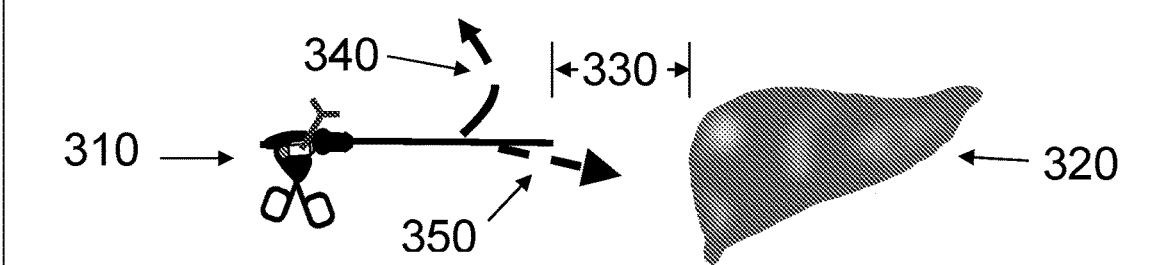

FIGS. 32c and 32d illustrate schematically the effect of the movement of tool 310 on the collision avoidance system. In FIGS. 32c and 32d, the tool 310 is close enough to the organ 320 that a collision between the two is possible. If the system tracked only the positions of the tool 310 and the organ 320, then motion of the tool 310 away from the organ 320 would be commanded. FIG. 32c illustrates the effect of a movement 350 that would increase the distance between tool 310 and organ 320. Since the movement 350 is away from organ 320, no collision is possible in this time step and no movement of the tool 310 is commanded.

In FIG. 32d, tool 310 is the same distance from organ 320 as in FIG. 32c. However, in FIG. 32d, the movement 350 of the tool 310 is toward the organ 320, making a collision between tool 310 and organ 320 possible. In some embodiments, a movement 340 is commanded to move the tool 310 away from the organ 320. In some embodiments, the system prevents movement 350, but does not command movement 340; in this embodiment the tool 310 will remain close to the organ 320. In some embodiments, the system warns the operator that move is RESTRICTED, but does not restrict movement 350 or command movement 340 away from the organ (320). Such a warning can be visual or aural, using any of the methods known in the art.

As a non-limiting example, in an operation on the liver, the collision detection function can warn the operator that a collision between a tool and the liver is likely but not prevent the collision; in an operation on the liver, a collision between the tool and the liver may be desired in order to remove tissue therefrom.

In another non-limiting example, in an operation on the gall bladder, the collision detection function can prevent a collision between the tool and the liver, either by preventing the movement or by commanding a movement redirecting the tool away from the liver.

Example 2—Tracking System with Soft Control—Fast Movement when Nothing is Nearby, Slow Movement when Something is Close One embodiment of such rule-based system comprises the following set of commands:

Detection (denoted by Gd):

Main Tool location detection function (denoted by GdM);

Gd-tool1-K—Tool location detection function;

Gd-organ2-L—Organ (e.g. Liver) detection function;

Gd3 Main Tool Movement (vector) calculation and estimation function;

Gd4 Proximity probability detection function;

Tool Instructions (denoted Gt):

Gt1 Movement vector (direction and speed) according to manual command

The scenario—manual move command by the surgeon:

Locations GdM(t), Gd-tool1-K(t) and Gd-organ2-L(t) are calculated in real time at each time step (from image or location marker).

Main Tool Movement Vector Gd3(t) is calculated per GdM (t) as the difference between the current location and at least one previous location (probably also taking into account previous movement vectors)

The proximity of the main tool to other tools—Gd4(t)—is calculated, for example, as the smallest of the differences between the main tool location and the other tools' locations.

Tool Instructions Gt1 Weight function $\alpha_t(t)$ is proportional to tool proximity function Gd4(t), the closer the tool the slower the movement so that, for example $\alpha_2(t)$=Gd4/maximum(Gd4)

or $\alpha_2(t)$=log (Gd4/maximum(Gd4)) where maximum(Gd4) is the maximum distance which is likely to result in a collision given the distances, the speed of the tool and the movement vector.

Tool Instructions=$\alpha_t(t)*Gt1$.

Example 3—Tracking System with No-Fly Rule/Function

In reference to FIG. 33a-d, which shows, in a non-limiting manner, an embodiment of a tracking system with no-fly rule. The system tracks a tool 310 with respect to a no-fly zone (460), in order to determine whether the tool will enter the no-fly zone (460) within the next time step. In this example, the no-fly zone 460 surrounds the liver.

Figure 33A:
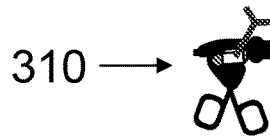
FIG. 33A-D schematically illustrates operation of an embodiment of a tracking system with no fly zone rule/function.
Figure 33A:
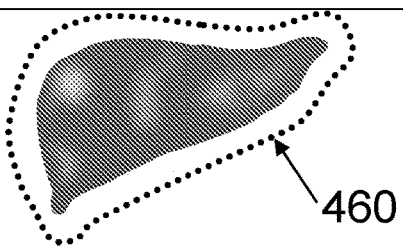
Figure 33B:
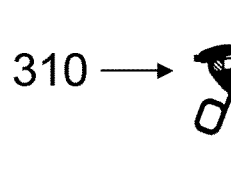
Figure 33B:
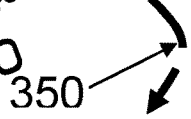
Figure 33C:
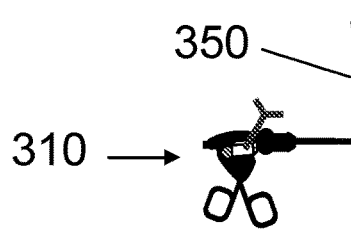
Figure 33C:
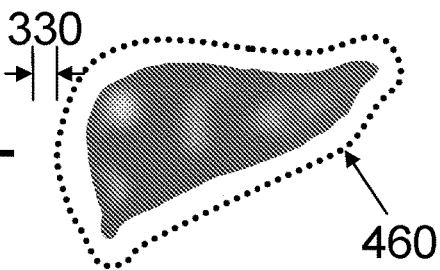
Figure 33D:
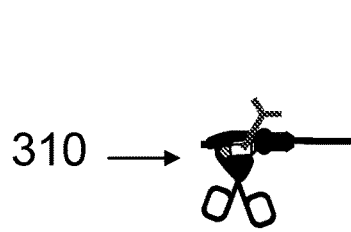
Figure 33D:
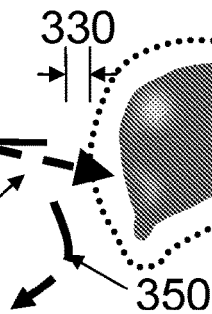

FIGS. 33a and 33b show how the behavior of the system depends on the location of the tool tip with respect to the no-fly zone, while FIGS. 33c and 33d show how movement of the tool affects the behavior.

In FIG. 33a, the tool 310 is outside the no-fly zone rule/function 460 and no movement of the tool is commanded. In FIG. 33b, the tool 310 is inside the no-fly zone 460.

The no-fly zone rule/function performs as follows:

In the embodiment illustrated, a movement 350 is commanded to move the tool 310 away from the no-fly zone 460. In some embodiments, the system prevents movement further into the no-fly zone (refers as movement 340, see FIG. 33c), but does not command movement 340; in such embodiments, the tool 310 will remain close to the no-fly zone 460.

In some embodiments, the system warns/signals the operator that the move is RESTRICTED, but does not restrict movement further into the no-fly zone or command movement 340 away from the no-fly zone 460. Such a warning/signaling can be visual or aural, using any of the methods known in the art.

FIGS. 33*c* and 33*d* illustrate schematically the effect of the tool's movement on operation of the no-fly zone rule/function. In FIGS. 33*c* and 33*d*, the tool 310 is close enough to the no-fly zone 460 (distance 330 is small enough) that it is possible for the tool to enter the no-fly zone during the next time step. FIG. 33*c* illustrates the effect of a movement 340 that would increase the distance between tool 310 and no-fly zone 460. Since the movement 340 is away from no-fly zone 460, no collision is possible in this time step and no movement of the tool 310 is commanded.

In FIG. 33*d*, tool 310 is the same distance from no-fly zone 460 as in FIG. 33*c*. However, in FIG. 33*d*, the movement 340 of the tool is toward no-fly zone 460, making it possible for tool 310 to enter no-fly zone 460. In the embodiment illustrated, a movement 350 is commanded to move the tool 310 away from the no-fly zone 460. In some embodiments, the system prevents movement 340, but does not command movement 350; in such embodiments, the tool 310 will remain close to the no-fly zone 460. In some embodiments, the system warns/signals the operator that the move is RESTRICTED, but does not restrict movement 340 or command movement 350 away from the no-fly zone rule/function 460. Such a warning/signaling can be visual or aural, using any of the methods known in the art.

Example 4—Tracking System with Preferred Volume Zone Rule/Function

In reference to FIG. 34*a-d*, which shows, in a non-limiting manner, an embodiment of a tracking system with a preferred volume zone function/rule.

The system tracks a tool 310 with respect to a preferred volume zone (570), in order to determine whether the tool will leave the preferred volume (570) within the next time step.

Figure 34A:
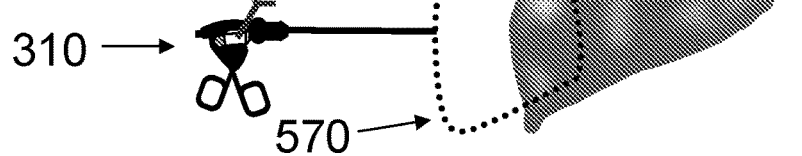
FIG. 34A-D schematically illustrates operation of an embodiment of a tracking system with preferred volume zone rule/function.
Figure 34B:
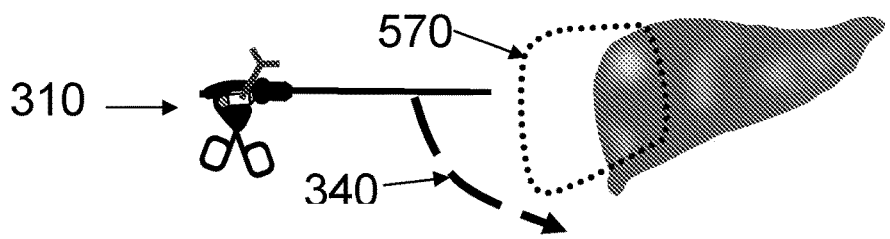

In this example, the preferred volume zone 570 extends over the right lobe of the liver. FIGS. 34*a* and 34*b* show how the behavior of the system depends on the location of the tool tip with respect to the preferred volume zone 570, while FIGS. 34*c* and 34*d* show how movement of the tool affects the behavior (i.e., the preferred volume zone rule/function).

In FIG. 34*a*, the tool 310 is inside the preferred volume zone 570 and no movement of the tool is commanded. In FIG. 34*b*, the tool 310 is outside the preferred volume zone 570.

In the embodiment illustrated, a movement 340 is commanded to move the tool 310 away from the preferred volume zone 570. In some embodiments, the system prevents movement 340; in such embodiments, the tool 310 will remain close to the preferred volume zone 570. In some embodiments, the system warns/signals the operator that the move 340 is RESTRICTED. Such a warning/signaling can be visual or aural, using any of the methods known in the art.

Figure 34C:
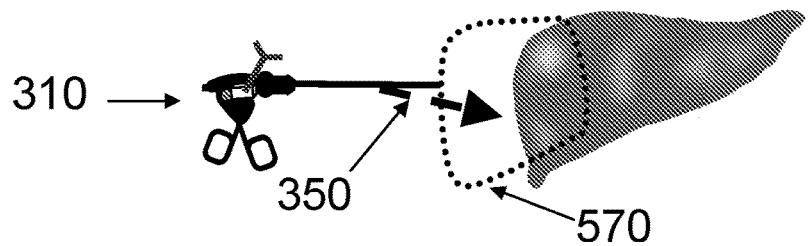
Figure 34D:
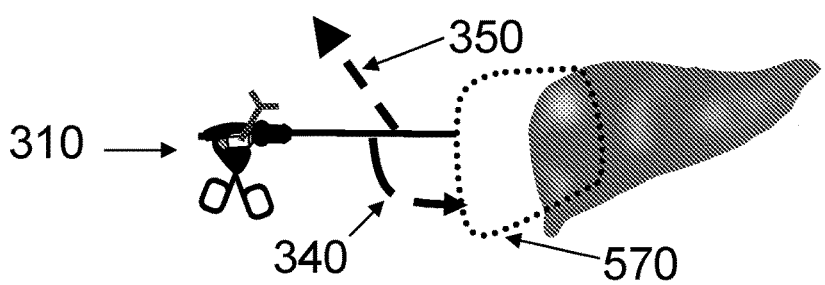

FIGS. 34*c* and 34*d* illustrate schematically the effect of the tool's movement on operation of the preferred volume rule/function. In FIGS. 34*c* and 34*d*, the tool 310 is close enough to the edge of preferred volume zone 570 that it is possible for the tool to leave the preferred volume zone during the next time step.

FIG. 34*c* illustrates the effect of a movement 350 that would take the tool 310 deeper into preferred volume zone 570. Since the movement 350 is into preferred volume 570, said movement is an allowed movement.

In FIG. 34*d*, the movement 350 of the tool is out of the preferred volume 570, making it possible for tool 310 to leave preferred volume 570.

According to one embodiment illustrated, a movement 340 is commanded to move the tool 310 into the preferred volume zone 570. In some embodiments, the system prevents movement 350, but does not command movement 340; in such embodiments, the tool 310 will remain close to the preferred volume zone 570. In some embodiments, the system warns/signals the operator that the move is RESTRICTED, but does not restrict movement 350 or command movement 340 away from the preferred volume zone 570. Such a warning/signaling can be visual or aural, using any of the methods known in the art.

Example 5—Organ/Tool Detection Function

Figure 35:
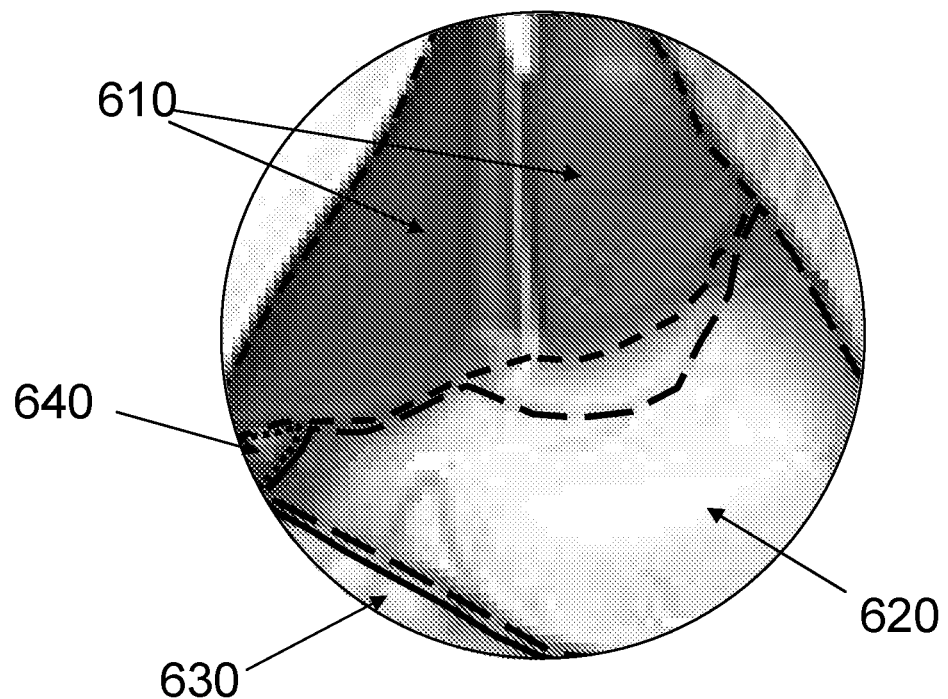
FIG. 35 schematically illustrates operation of an embodiment of the organ detection function/rule.

In reference to FIG. 35, which shows, in a non-limiting manner, an embodiment of an organ detection system (however, it should be noted that the same is provided for detection of tools, instead of organs).

For each organ, the 3D spatial positions of the organs stored in a database. In FIG. 35, the perimeter of each organ is marked, to indicate the edge of the volume of 3D spatial locations stored in the database.

In FIG. 35, the liver 610 is labeled with a dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 36:
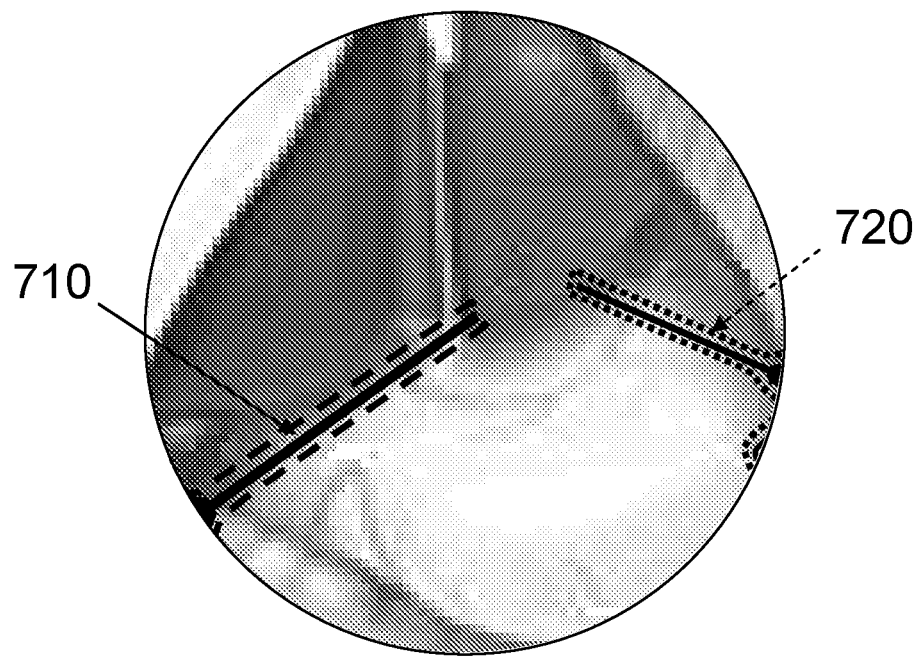
FIG. 36 schematically illustrates operation of an embodiment of the tool detection function/rule.

In reference to FIG. 36, which shows, in a non-limiting manner, an embodiment of a tool detection function. For each tool, the 3D spatial positions of the tools stored in a database. In FIG. 36, the perimeter of each tool is marked, to indicate the edge of the volume of 3D spatial locations stored in the database. In FIG. 36, the left tool is labeled with a dashed line while the right tool is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 37A:
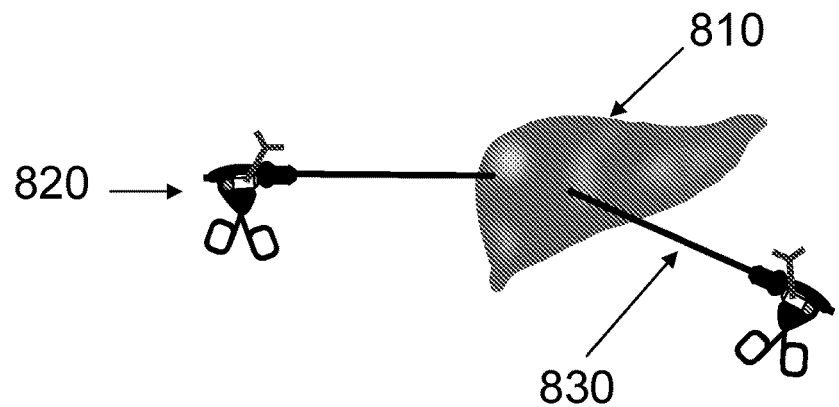
FIG. 37A-B schematically illustrates operation of an embodiment of the movement detection function/rule.
Figure 37B:
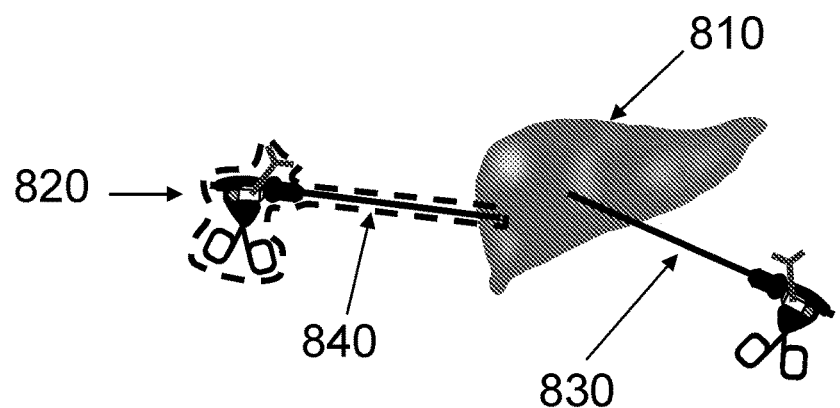

In reference to FIG. 37*a-b*, which shows, in a non-limiting manner, an embodiment of a movement detection function/rule. FIG. 37*a* schematically illustrates a liver 810, a left tool 820 and a right tool 830 at a time t. FIG. 37*b* schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 37*b* by a dashed line around left tool 820.

Example 8—Prediction Function

In reference to FIG. 38*a-d*, which shows, in a non-limiting manner, an embodiment of the above discussed prediction function.

Figure 38A:
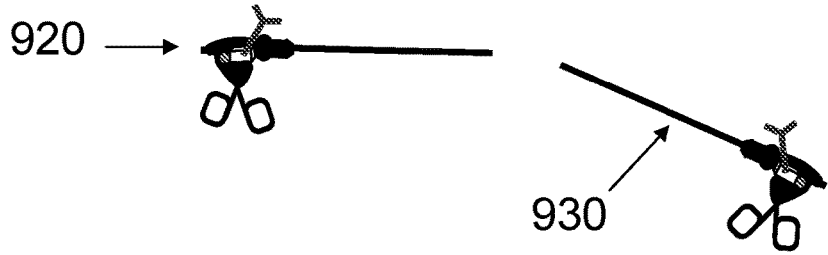
FIG. 38A-D schematically illustrates operation of an embodiment of the prediction function/rule.

FIG. 38*a* shows a left tool 920 and a right tool 930 at a time t.

Figure 38B:
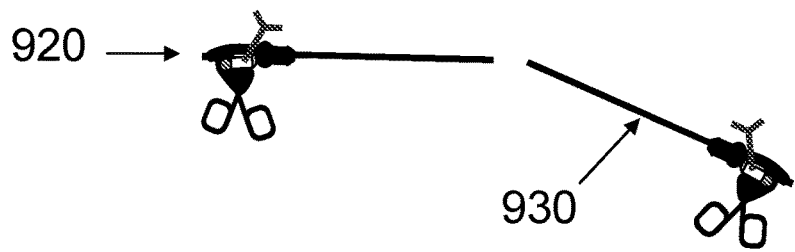
Figure 38C:
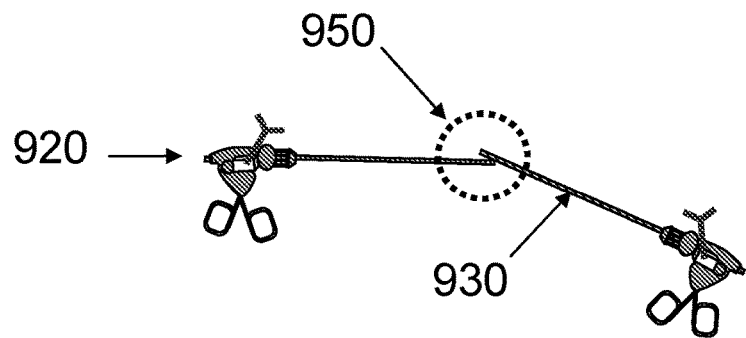
Figure 38D:
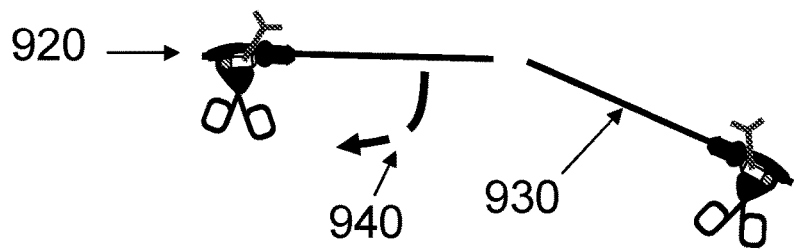

FIG. 38*b* shows the same tools at a later time t+Δt, where Δt is a small time interval. Left tool 920 is moving to the right and downward, while right tool 930 is moving to the left and upward. If the motion continues (shown by the dashed line in FIG. 38*c*), then by the end of the next time interval, in other words, at some time between time t+Δt and time t+2Δt, the tools will collide, as shown by tool tips within the dotted circle 950 in FIG. 38*c*.

In this embodiment, the system automatically prevents predicted collisions and, in this example, the system applies a motion 940 to redirect left tool 920 so as to prevent the collision.

In some embodiments, the system warns/signals the operator that a collision is likely to occur, but does not alter the movement of any tool. Such a warning/signaling can be visual or aural, using any of the methods known in the art.

In some embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 39:
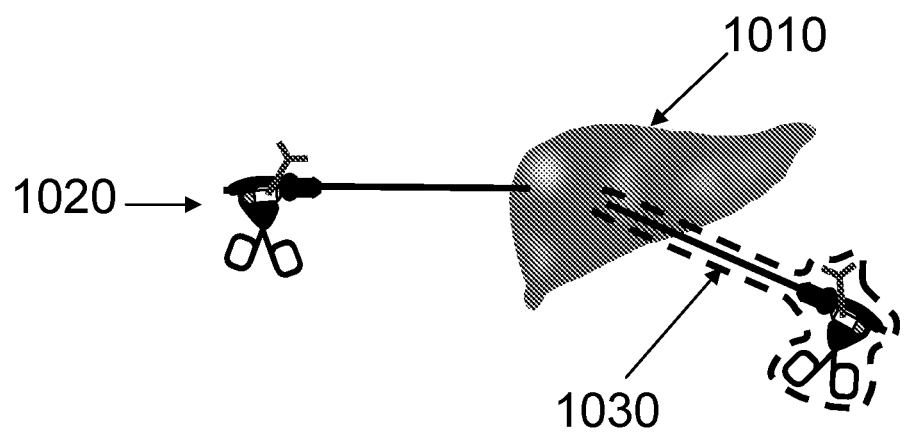
FIG. 39 schematically illustrates operation of an embodiment of the right tool function/rule.

In reference to FIG. 39, which shows, in a non-limiting manner, an embodiment of a right tool function. FIG. 39 schematically illustrates a liver 1010, a left tool 1020 and a right tool 1030. The right tool, illustrated schematically by the dashed line 1040, is labeled and its 3D spatial location is constantly and real-time stored in a database. Now, according to the right tool function/rule the endoscope constantly tracks the right tool.

It should be pointed out that the same rule/function applies for the left tool (the left tool function/rule).

Example 10—Field of View Function/Rule

Figure 40A:
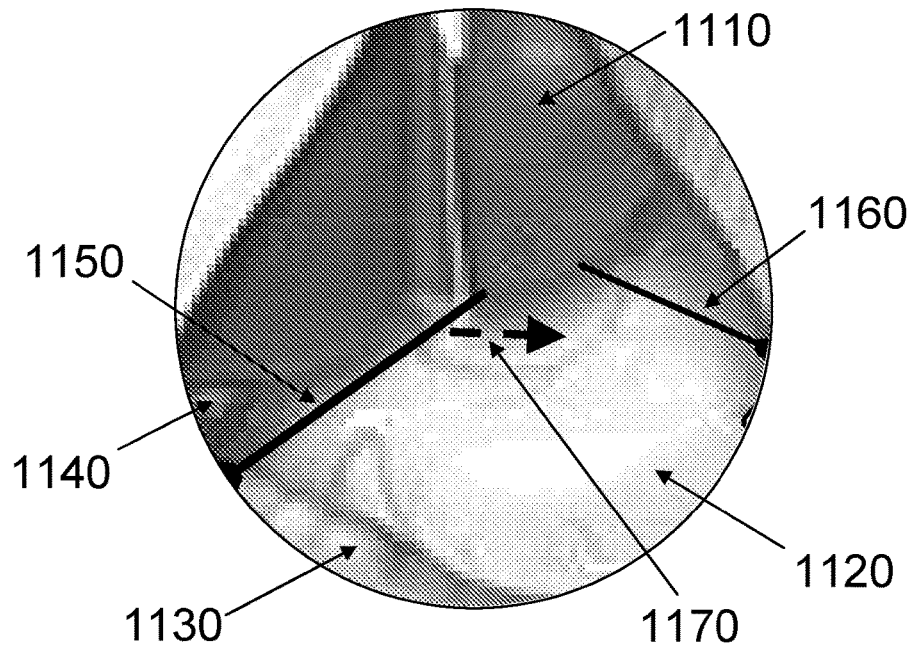
FIG. 40A-B schematically illustrates operation of an embodiment of the field of view function/rule.
Figure 40B:
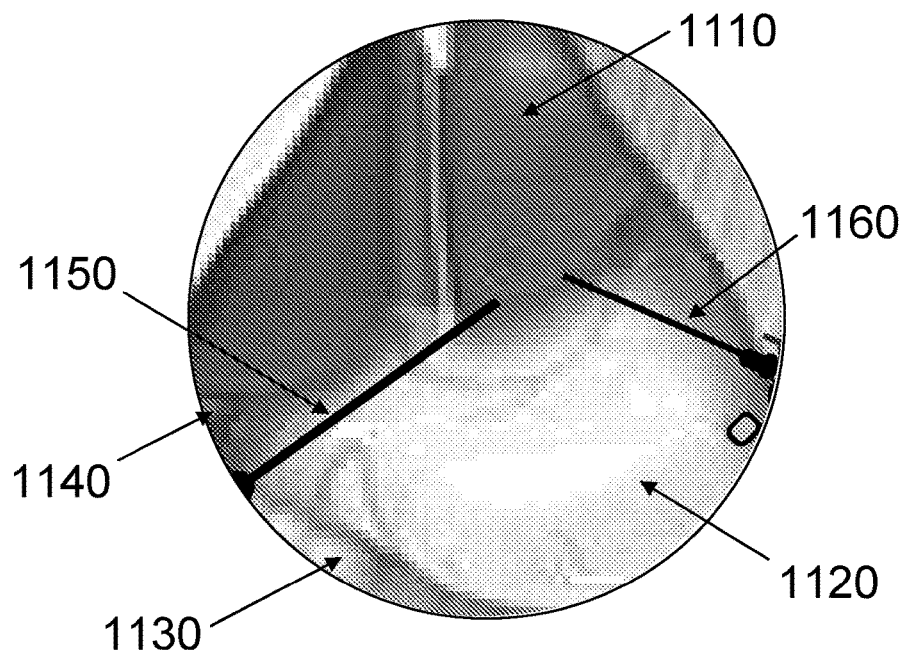

In reference to FIG. 40*a-b*, which shows, in a non-limiting manner, an embodiment of a field of view function/rule.

FIG. 40*a* schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

FIG. 40*b* shows the field of view at time t+Δt. The field of view has moved to the right so that the tip of left tool 1150 is still nearly at the center of the field of view. It can be seen that much less of gall bladder 1140 is visible, while more of right tool 1160 has entered the field of view.

The field of view function/rule can be set to follow a selected tool, as in this example or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 41:
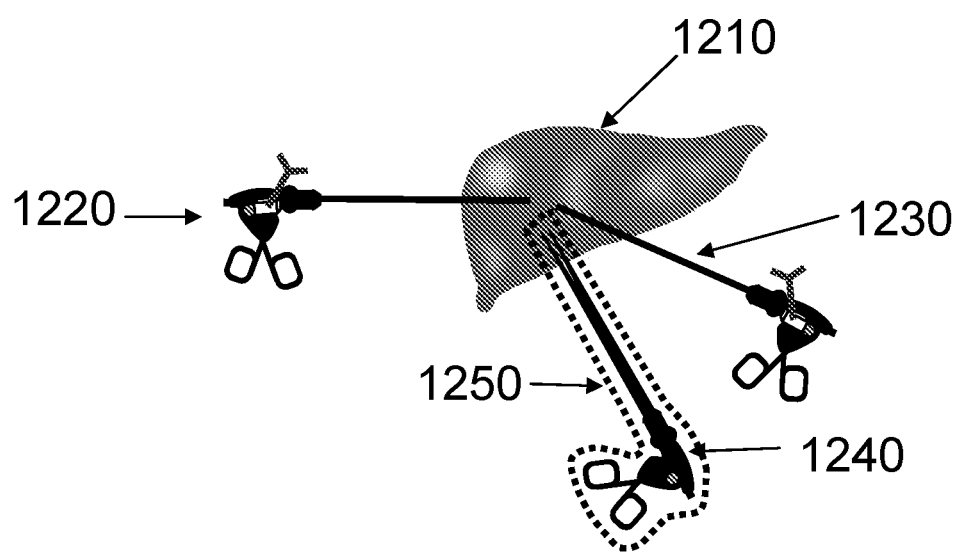
FIG. 41 schematically illustrates operation of an embodiment of the tagged tool function/rule.

In reference to FIG. 41, which shows, in a non-limiting manner, an embodiment of a tagged tool function/rule.

FIG. 41 shows three tools (1220, 1230 and 1240) in proximity to the organ of interest, in this example, the liver 1210.

The tool most of interest to the surgeon, at this point during the operation, is tool 1240. Tool 1240 has been tagged (dotted line 1250); the 3D spatial location of tool 1240 is constantly stored in a database and this spatial location has been labeled as one of interest.

The system can use this tagging for many purposes, including, but not limited to, keeping tool 1240 in the center of the field of view, predicting its future motion, keeping it from colliding with other tools or keeping other tools from colliding with it, instructing the endoscope to constantly monitor and track said tagged tool 1250 and so on.

It should be noted that in the preferred tool rule, the system tags one of the tools and performs as in the tagged tool rule/function.

Example 12—Proximity Function/Rule

Figure 42A:
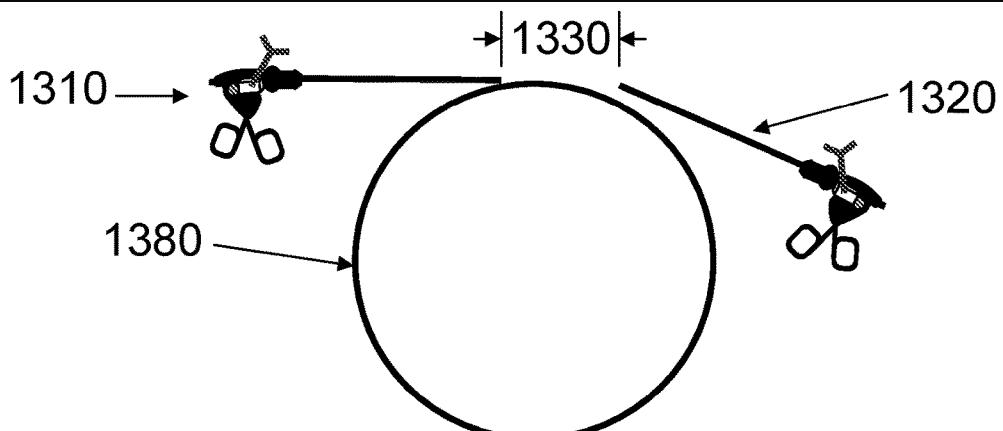
FIG. 42A-C schematically illustrates operation of an embodiment of the proximity function/rule.
Figure 42B:
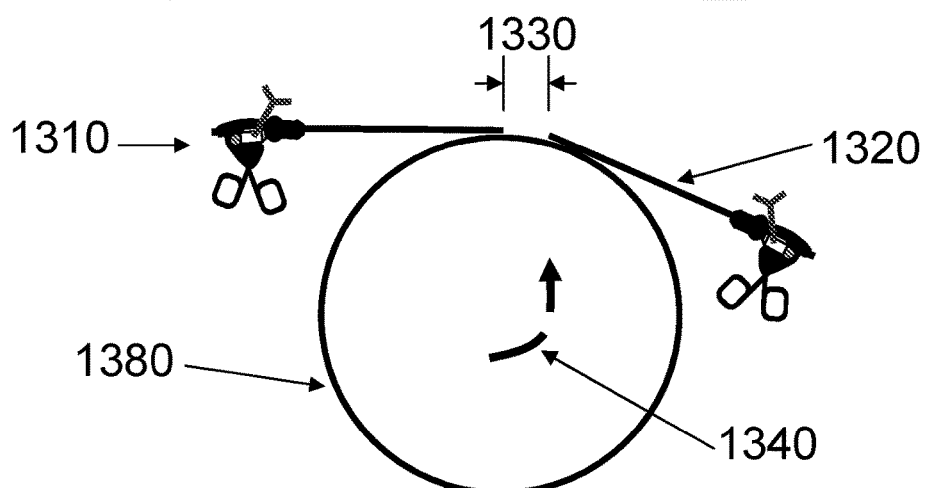
Figure 42C:
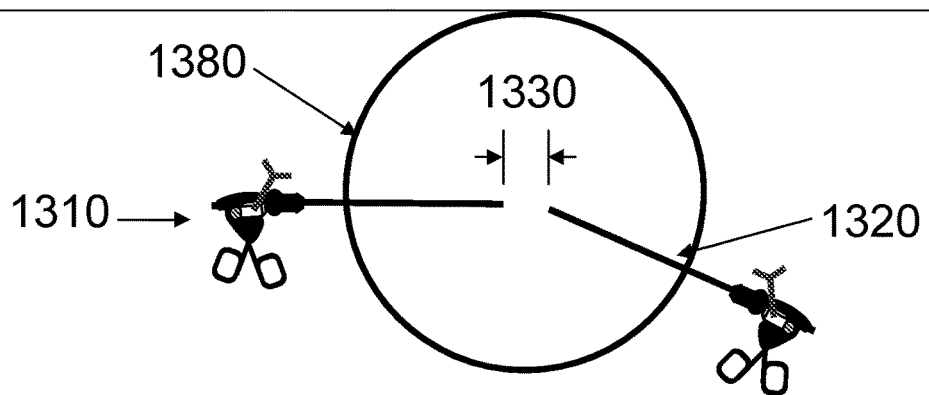

In reference to FIG. 42*a-c*, which shows, in a non-limiting manner, an embodiment of a proximity function/rule.

FIG. 42*a* schematically illustrates two tools (1310 and 1320) separated by a distance 1330 which is greater than a predefined proximity distance. Since tool 1310 is not within proximity of tool 1320, the field of view (1380) does not move.

FIG. 42*b* schematically illustrates two tools (1310 and 1320) separated by a distance 1330 which is less than a predefined proximity distance.

Since tool 1310 is within proximity of tool 1320, the field of view 1380 moves upward, illustrated schematically by arrow 1340, until the tips of tool 1310 and tool 1320 are in the center of field of view 1380 (FIG. 42*c*).

Alternatively the once the distance 1330 between the two tool 1320 and 1310 is smaller than a predetermined distance, the system alerts the user of said proximity (which might lead to a collision between the two tools). Alternatively, the system moves one of the tools away from the other one.

Example 13—Operator Input Function/Rule

Figure 43A:
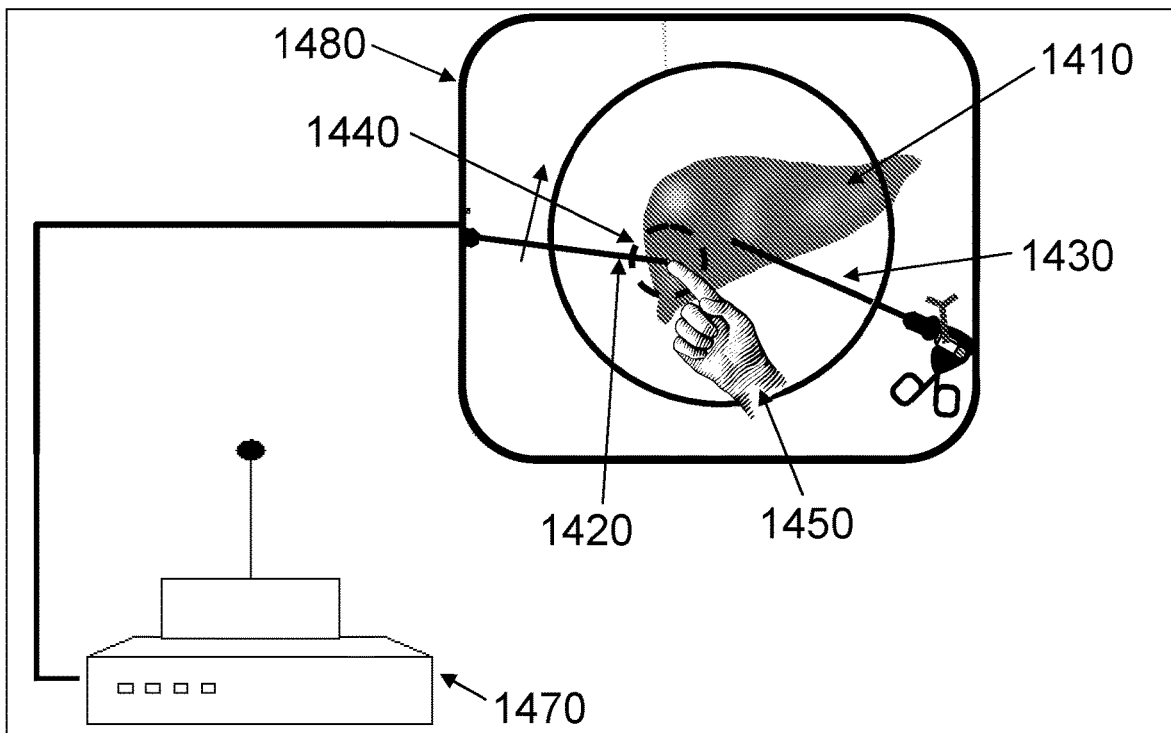
FIG. 43A-B schematically illustrates operation of an embodiment of the operator input function/rule.
Figure 43B:
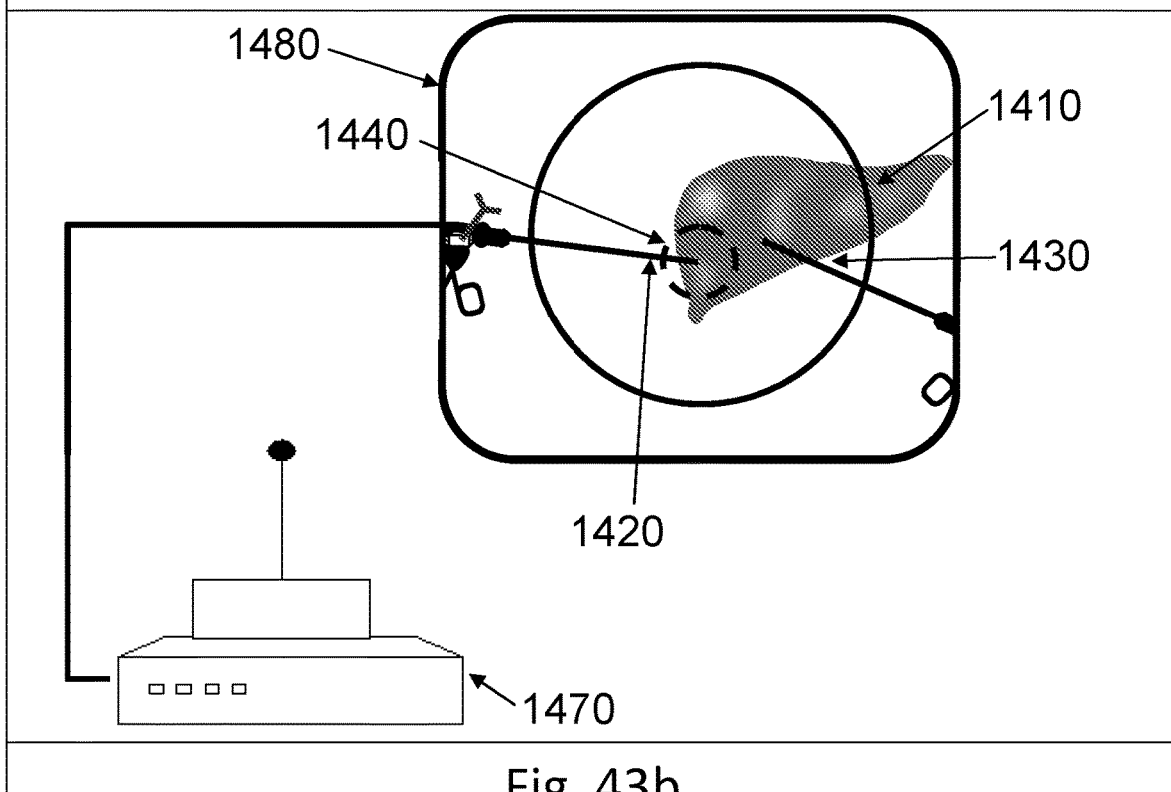

In reference to FIG. 43a-b, which shows, in a non-limiting manner, an embodiment of an operator input function/rule. According to this embodiment, input is received from the operator.

In the following example, the input received from the operator is which tool to track.

FIG. 43a schematically illustrates an endoscope with field of view 1480 showing a liver 1410 and two tools 1420 and 1430. Operator 1450 first selects the tip of the left tool as the region of interest, preferably by touching the tool tip on the screen, causing the system to tag (1440) the tip of the left tool.

As illustrated in FIG. 43b, the system then directs and modifies the spatial position of the endoscope so that the tagged tool tip 1440 is in the center of the field of view 1480.

Another example of the operator input function/rule is the following:

If a tool has been moved closely to an organ in the surgical environment, according to the proximity rule or the collision prevention rule, the system will, according to one embodiment, prevent the movement of the surgical tool.

According to one embodiment of the present invention, once the surgical tool has been stopped, any movement of said tool in the direction is interpreted as input from the operator to continue the movement of said surgical tool in said direction.

Thus, according to this embodiment, the operator input function/rule receives input from the operator (i.e., physician) to continue the move of said surgical tool (even though it is "against" the collision prevention rule). Said input is simply in the form of the continued movement of the surgical tool (after the alert of the system or after the movement prevention by the system).

Example 14—Constant Field of View Rule/Function

In reference to FIGS. 44a-d, which shows, in a non-limiting manner, an embodiment of a tracking system with a constant field of view rule/function.

In many endoscopic systems, the tip lens in the camera optics is not at a right angle to the sides of the endoscope. Conventionally, the tip lens angle is described relative to the right angle, so that a tip lens at right angles to the sides of the endoscope is described as having an angle of 0. Typically, angled endoscope tip lenses have an angle of 30° or 45°. This tip lens angle affects the image seen during zooming. FIG. 44 illustrates, in an out-of-scale manner, for a conventional system, the effect of zooming in the field of view in an endoscope with tip lens set straight in the end (FIGS. 44a and 44b) vs. the effect of zooming in the field of view in an endoscope with angled tip lens (FIGS. 44c and 44d).

Figure 44A:
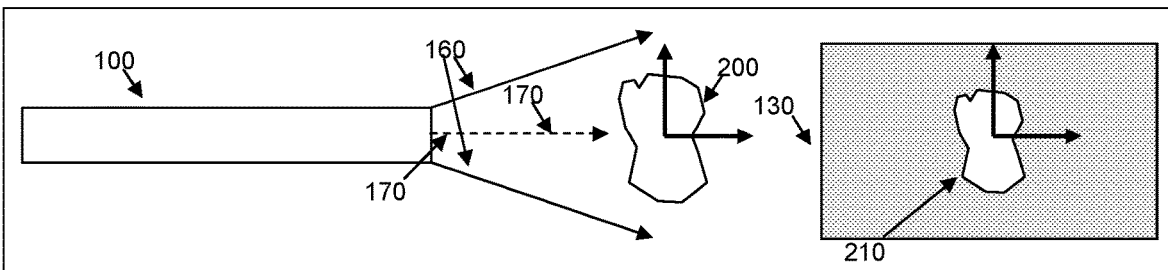
FIGS. 44A-D schematically illustrate an embodiment of a tracking system with a constant field of view rule/function.
Figure 44B:
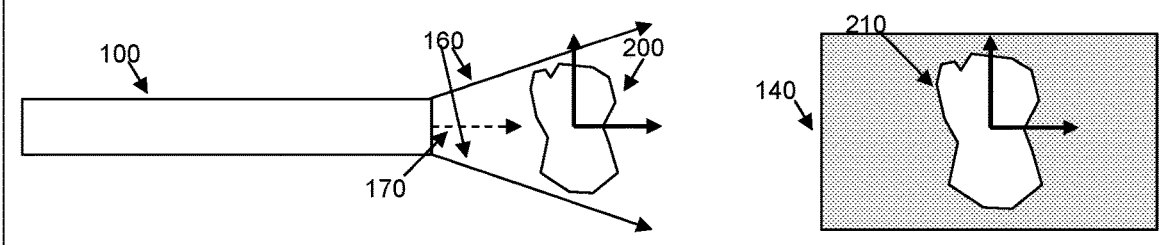
Figure 44C:
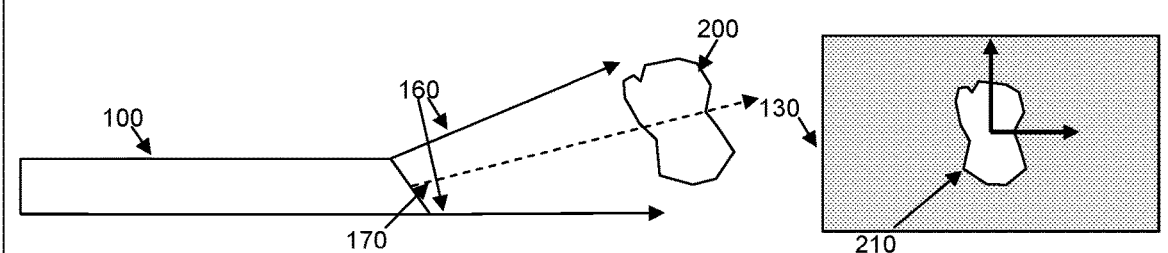
Figure 44D:
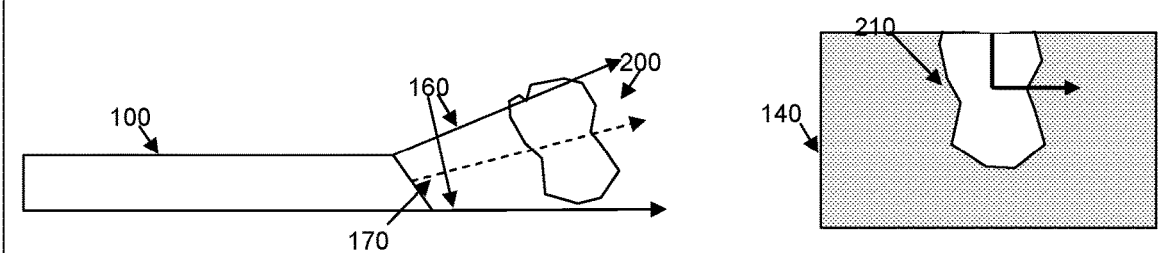

FIGS. 44a and 44c illustrate the endoscope (100), the object it is viewing (200) and the image seen by the endoscope camera (130) before the zoom. The solid arrows (160) show the limits of the FOV and the dashed arrow (170), the center of the field of view (FOV); since the object is in the center of the FOV, an image of the object (210) is in the center of the camera image (130). FIGS. 44b and 44d illustrate the endoscope (100), the object it is viewing (200) and the image seen by the endoscope camera (130) after the zoom. The solid arrows (160) show the limits of the FOV and the dashed arrow (170), the center of the field of view.

If the tip lens is set straight in the end of the endoscope (FIGS. 44a and 44b), an object (200) in the center of the field of view will be in the center of the field of view (FOV) (and the camera image) (130) both before (FIG. 44a) and after (FIG. 44b) the zoom. However, if the tip lens is set at an angle in the end of the endoscope (FIGS. 44c and 44d), then an object that is in the center of the FOV (and the camera image) before the zoom (FIG. 44c) will not be in the center of the FOV (or the camera image) after the zoom (FIG. 44d) since the direction of motion of the endoscope is not the direction in which the center of the field of view (170) points.

In an embodiment of the system of the present invention, unlike in conventional systems, the controlling means maintains the center of the field of view (FOV) during zoom independent of the tip lens angle. An advantage of controlling the zoom of the endoscope via a data processing system is that the tip lens angle does not need to be input to the data processing system, obviating a possible source of error.

According to one embodiment of the present invention, the endoscope's movement will be adjusted in order to maintain a constant field of view.

Example 15—Misalignment Rule/Function

According to some embodiments of the present invention, the system can inform the user of any misalignment of the same system.

Misalignment of the system may cause parasitic movement of the endoscope tip, where the endoscope tip does not move exactly in the expected direction. According to one embodiment of the system, the system comprises sensors (e.g., gyroscopes, accelerometers and any combination thereof) that calculate/estimates the position of the pivot point in real time in order to (a) inform the user of misalignment; or (b) calculate the misalignment so that the system can adjust its movement to prevent parasitic movement.

Example 16—Change of Speed Rule/Function

Figure 45:
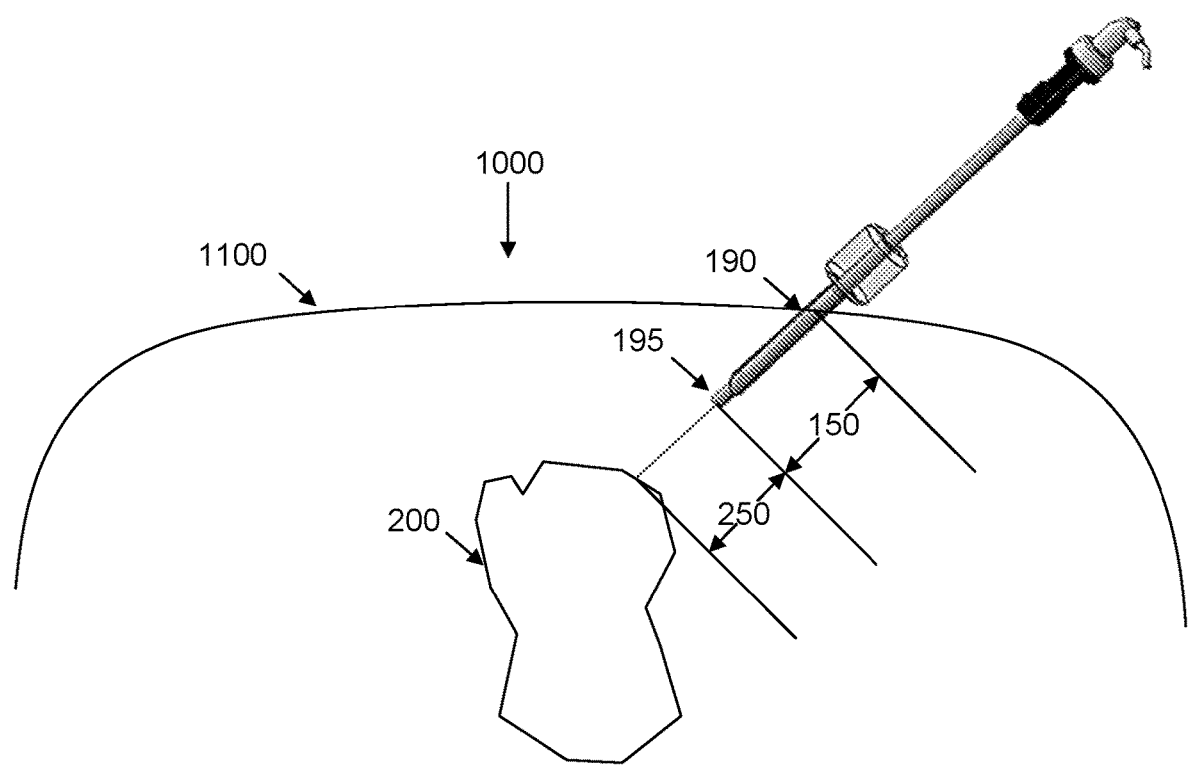
FIG. 45 schematically illustrates an embodiment of a tracking system with a change of speed rule/function.

In reference to FIG. 45, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves. In this embodiment, as shown in FIG. 45, measurements are made of the distance X (150) from the tip (195) of the endoscope (100) to the pivot point of the endoscope (190), where said pivot point is at or near the surface of the skin (1100) of a patient (1000). Measurements are also made of the distance Y (250) from the tip of the endoscope (195) to the object in the center of the scene of view (200). From a predetermined velocity $V_p$, the actual velocity of the tip of the endoscope at a given time, $V_{act}$, is calculated from $$V_{act} \propto \frac{Y}{X} V_p$$

Therefore, the closer to the object at the center of the scene of view, the more slowly the endoscope moves, making it possible to use automatic control of even fine adjustments, and reducing the probability that the endoscope will come in contact with tissue or instruments.

Example 17—Articulation of Tool

In reference to FIG. 46a-b, a non-limiting example of movement of an articulating tool (310), here an endoscope, is shown schematically.

In FIG. 46a-b, the endoscope (310) is moved so that, instead of viewing the outer side of the liver (320) from the right, it views the inner side of the liver (320) from the left.

FIG. 46a shows the endoscope (310) at the beginning of the movement. It is fully extended and its tip (318) is positioned about halfway up the outer side of the liver. The dashed line shows the movement of the base (312) of the endoscope, which will move in a straight line from its starting position (FIG. 46a) to its final position (FIG. 20b). The dotted line shows the movement of the endoscope tip (318)—the tip (318) moves upward, over the top of the liver (320), and then down the inner side of the liver (320), to allow imaging of the left (inner) side of the liver from between the liver (320) and the lungs (1790).

In FIG. 46b, the movement has been completed. The endoscope tip (318) now points rightward; the articulating section (316) being curved so that the endoscope (310) views the right side of the liver (310), with the endoscope tip (318) being between the liver (320) and the lungs (1790) while its base (312) remains on the right side of the body.

Example 18—Articulation of Tool

In reference to FIG. 47, a non-limiting example of flexion of an articulating tool (310), here an endoscope, is shown schematically.

In FIG. 47, portions of the small intestine (1795) are shown schematically. The endoscope enters the body from the body's right side (body not shown), and views a portion of the small intestine (1795F) from the left and below. The articulating section of the endoscope (316) bypasses a loop of small intestine (1795A), passes between two portions of small intestine (1795B, 1795C), and over other portions of small intestine (1795D, 1795E) so that the endoscope's tip (318) views the desired portion of the small intestine (1795F) from the desired direction.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A structured-light based system for providing a 3D image of at least one object within a field of view within a body cavity, comprising:
   at least one endoscope having at least one lens in the endoscope's distal end;
   at least one camera located in the endoscope, configured to real-time provide at least one 2D image of at least a portion of said field of view by means of said at least one lens;
   at least one light source, configured to real-time illuminate at least a portion of said at least one object within at least a portion of said field of view with at least one time and space varying predetermined light pattern; and,
   at least one sensor configured to detect light reflected from said field of view;
   a computer program which, when executed by a data processing apparatus, is configured to calculate 3D locations of points on a surface of said object and to generate a 3D image of said field of view;
   wherein said predetermined light pattern is a structured light pattern; wherein said 3D image is constructable, and said 3D locations are determined, from said detected light reflected from said field of view and said structured light pattern;
   at least one location estimating means configured to real-time locate the 3D spatial position at any given time t of at least one of the endoscope and a surgical tool;
   wherein the system is operable in accordance with a collision prevention rule to generate a user alert if a distance between the surface and said at least one of the endoscope and surgical tool, as determined using the 3D spatial position, falls below a predetermined distance.

2. The system of claim 1, additionally comprising at least one maneuvering system, configured to maneuver said endoscope in at least two degrees of freedom (DOF).

3. The system of claim 1, wherein said endoscope is an articulating endoscope.

4. The system of claim 1, wherein said construction of said 3D image is by means of calculating world coordinates of at least one point on said at least one object.

5. The system of claim 4, wherein said world coordinates of at least one point on said at least one object can be calculated from the following equation:

$$\tilde{\alpha} = \frac{n^T \tilde{x}_p}{n^T R_p v_c}.$$

where $n^T$ is the transpose of the normal to the plane defined by the stripe ID $x_p$, $\tilde{x}_p = x_p + [\delta x_p, 0, f_p]^T$ is the perturbed stripe ID $x_p$, $R_p$ is the rotation matrix defining the transformation between the world coordinate system and the projector coordinate system and $v_c$ is the direction of the ray between the stripe ID and the object point.

6. The system of claim 1, wherein, for any point $X_w$ in world coordinate system, the coordinate $X_c$ of the same point in the camera coordinate system is calculated according to the following equation:

$$X_c = C_c X_w,$$

where $C_c$, the camera perspective projection matrix, is of the form $$C_c = \alpha \begin{bmatrix} f_x & kf_y & x_c^0 \\ 0 & f_y & y_c^0 \\ 0 & 0 & 1 \end{bmatrix} [R_c \ t_c].$$

where $\alpha$ is a proportion coefficient, fx and fy are the camera focal length scaled to each of the camera image dimensions, k is the shear of the camera coordinate system, $x_c^0$ and $y_c^0$ are the origin of Xc in image coordinates, and $R_c$ and $t_c$ define the transformation between the world coordinate system and the light source's coordinate system, with $R_c$ being a rotation matrix and $t_c$ a translation matrix.

7. The system of claim 6, wherein $x_p^0$ is the x-coordinate of the intersection of the optical axis and the projector.

8. The system of claim 1, wherein, for any point $X_w$ in world coordinate system, the coordinate $X_p$ of the same point in the light source coordinate system is calculated according to the following equation:

$$Xp = CpXw,$$

where Cp, the light source perspective projection matrix, is of the form $$C_p = \alpha \begin{bmatrix} f_p & 0 & x_p^0 \\ 0 & 0 & 1 \end{bmatrix} [R_p \ t_p]$$

where $\alpha$ is a proportion coefficient, $f_p$ is the light source focal length scaled to projector dimensions, $x_p^0$ is the origin of Xp in projector coordinates, and $R_p$ and $t_p$ define the transformation between the world coordinate system and the light source's coordinate system, with $R_p$ being a rotation matrix and $t_p$ a translation matrix.

9. The system of claim 1, wherein world coordinates $p_w$ of a point P are calculated according to the following equation:

$$\begin{pmatrix} p_p \\ p_s \end{pmatrix} - \begin{pmatrix} F_c(p_w; \Theta_c) \\ F_p(p_w; \Theta_p) \end{pmatrix} = 0$$

where $p_p = (x_p, y_p)^t$ is the pixel coordinate of said point, $p_x = (x_s)$ is the stripe value of said point P, $F_c(P_w; \Theta_c) = P_p - \in_p$ is the noise-free value of the vector of pixel coordinates, where $P_p$ is the vector of measured pixel coordinates and $\in_p$ is the vector of errors in the pixel coordinates; $F_p(P_w; \Theta_p) = P_s - \in_s$ is the noise-free value of the vector of stripe coordinates, where $P_s$ is the vector of measured stripe coordinates and E s is the vector of errors in the stripe coordinates.

10. The system of claim 9, wherein the world coordinates $p_w$ of a point P are estimated according to the following non-linear least squares (NLLS) equations:

$$\min_{\Theta_c} \|P_p - F_c(P_w; \Theta_c)\|^2$$

-continued $$\min_{\Theta_p} \|P_s - F_p(P_w; \Theta_p)\|^2$$

11. The system of claim 10, wherein said NLLS equations are solvable by means of a NLLS solving algorithm selected from the group consisting of the Gauss-Newton technique, the quasi-Newton technique, and the Levenberg-Marquardt technique.

12. The system of claim 1, wherein a location, in world coordinates, of a kth point on the object is calculated according to the following equation:

$$p_w^k = \frac{C_{1,2,1}^k - x_p C_{3,2,1}^k - y_p C_{1,3,1}^k - x_s C_{1,2,2}^k + x_s x_p C_{3,2,2}^k + x_s y_p C_{1,3,2}^k}{C_{1,2,1}^4 - x_p C_{3,2,1}^4 - y_p C_{1,3,1}^4 - x_s C_{1,2,2}^4 + x_s x_p C_{3,2,2}^4 + x_s y_p C_{1,3,2}^4}$$

where $C_{i,j,l}^k = \det(C_c^i, C_c^j, C_c^l, e_k)$ are constants which depend only on a camera perspective transformation matrix and a projector perspective transformation matrix.

13. The system of claim 1, additionally comprising a calibration object.

14. The system of claim 13, wherein said calibration object is of predetermined shape and size.

15. The system of claim 13, wherein said calibration object comprises fiducial locations of predetermined position.

16. The system of claim 1, wherein said lens is a wide-angle lens.

17. The system of claim 16, wherein said wide-angle lens is selected from the group consisting of a fisheye lens, an omnidirectional lens and any combination thereof.

18. The system of claim 1, wherein said structured light pattern uses at least one of a group consisting of: temporal sequencing, spatial sequencing, wavelength sequencing and any combination thereof.

19. The system of claim 18, wherein cancerous tissue can be differentiated from normal tissue by means of said wavelength sequencing.

20. The system of claim 1, wherein the relationship between a location of a point in said 2D camera image, a location of a point in a light source, and a location of a point in space is known for all said points in said 2D camera image, said points in said light source and said points in space.

21. The system of claim 19, wherein said known relationships are used to generate said 3D image from said 2D camera image.

22. The system of claim 1, wherein said at least one location estimating means comprises:
at least one element selected from the group consisting of optical imaging means, radio frequency transmitting and receiving means, at least one mark on said at least one surgical tool and any combination thereof; and,
at least one surgical instrument spatial location software configured to estimate said 3D spatial position of said at least one surgical tool by means of said element.

23. The system of claim 1, wherein display of said 3D image is by means of a member of the group consisting of: a 3D screen, 3D glasses, autostereoscopy, holography, a volumetric display, integral imaging, wiggle stereoscopy, an active shutter 3d system, a polarized 3d system, an interference filter system, a color anaglyph system, a Chromadepth system, an over/under format, and any combination thereof.

24. The system of claim 1, wherein tools within said field of view are detectable by means of depth cues in said 3D image.

25. The system of claim 1, wherein at least one structure selected from the group consisting of an organ, a blood vessel, a nerve, a limb and any combination thereof is detectable by said system.

26. The system of claim 25, wherein said at least one structure are emphasizable by a member of a group consisting of: virtual reality overlays, color markings, pattern markings, outlines, arrows, and any combination thereof.

27. The system of claim 1, wherein data from at least one other imaging modality is storable in a database.

28. The system of claim 27, wherein said data from said at least one other imaging modality is matchable to and alignable with said 3D image, such that substantially all information from said at least one other imaging modality and said 3D image is viewable as a single 3D image.

29. The system of claim 27 wherein said at least one other imaging modality is selected from the group consisting of: CT, MRI, ultrasound and PET and any combination thereof.

30. The system of claim 1, wherein additional information presentable by said system is selected from the group consisting of: recommendations useful in directing the progress of an operation, information useful in assisting an operator in making a decision, information useful for a record of the operation and any combination thereof.

31. The system of claim 30, wherein said information is presentable visually or audibly.

32. The system of claim 30, wherein said information is selected from the group consisting of: camera pose, body temperature, time, elapsed time since start of operation, patient notes, notes made during the operation, and other information accessible to the system and any combination thereof.

33. A method for providing a 3D image of at least one object within a field of view within a body cavity by means of a structured-light based endoscope, comprising:
  providing a structured-light based system comprising:
    at least one endoscope having at least one lens in the endoscope's distal end;
    at least one camera located in the endoscope, configured to real-time provide at least one 2D image of at least a portion of said field of view by means of said at least one lens;
    at least one light source, configured to real-time illuminate at least a portion of said at least one object within at least a portion of said field of view with at least one time and space varying predetermined light pattern;
    at least one sensor configured to detect light reflected from said field of view;
    a computer program which, when executed by data processing apparatus, is configured to generate a 3D image of said field of view;
  maneuvering said endoscope and controlling the movements of the same;
  illuminating said at least a portion of said field of view with said at least one time and space varying predetermined light pattern;
  detecting said light reflected from said field of view; and,
  from said light reflected from said field of view, generating said 3D image of said field of view and calculating 3D locations of points on a surface of said object;
  wherein said predetermined light pattern is a structured light pattern; further wherein said 3D image is constructable from said detected light reflected from said field of view and said structured light pattern
  causing a location estimating means configured to real-time locate the 3D spatial position at any given time t of at least one of the endoscope and a surgical tool;
  causing the system to generate a user alert if a distance between the surface and said at least one of the endoscope and surgical tool, as determined using the 3D spatial position, falls below a predetermined distance.

34. The method of claim 33, additionally comprising providing at least one maneuvering system, configured to maneuver said endoscope in at least two degrees of freedom (DOF).

35. The method of claim 33, wherein said endoscope is an articulating endoscope.

36. The method of claim 33, comprising constructing said 3D image by calculating world coordinates of at least one point on said at least one object.

37. The method of claim 36, comprising calculating said world coordinates of said at least one point on said at least one object from the following equation:

$$\tilde{\alpha} = \frac{n^T \tilde{x}_p}{n^T R_p v_c}.$$

where $n^T$ is the transpose of the normal to the plane defined by the stripe ID $x_p$, $\tilde{x}_p = x_p + [\delta x_p, 0, f_p]^T$ is the perturbed stripe ID $x_p$, $R_p$ is the rotation matrix defining the transformation between the world coordinate system and the projector coordinate system and $v_c$ is the direction of the ray between the stripe ID and the object point.

38. The method of claim 33, comprising, for any point $X_w$ in world coordinate system, calculating the coordinate $X_c$ of the same point in the camera coordinate system according to the following equation:

$$X_c = C_c X_w,$$

where $C_c$, the camera perspective projection matrix, is of the form $$C_c = \alpha \begin{bmatrix} f_x & k f_y & x_c^0 \\ 0 & f_y & y_c^0 \\ 0 & 0 & 1 \end{bmatrix} [R_c \ t_c].$$

where $\alpha$ is a proportion coefficient, fx and fy are the camera focal length scaled to each of the camera image dimensions, k is the shear of the camera coordinate system, $x_c^0$ and $y_c^0$ are the origin of Xc in image coordinates, and $R_c$ and $t_c$ define the transformation between the world coordinate system and the light source's coordinate system, with $R_c$ being a rotation matrix and $t_c$ a translation matrix.

39. The method of claim 38, comprising defining $x_p^0$ to be the x-coordinate of the intersection of the optical axis and the projector.

40. The method of claim 33, comprising, for any point $X_w$ in world coordinate system, calculating the coordinate $x_p$ of the same point in the light source coordinate system according to the following equation:

$$Xp = CpXw,$$

where Cp, the light source perspective projection matrix, is of the form $$C_p = \alpha \begin{bmatrix} f_p & 0 & x_p^0 \\ 0 & 0 & 1 \end{bmatrix} [R_p \ t_p]$$

where α is a proportion coefficient, $f_p$ is the light source focal length scaled to projector dimensions, $x_p^0$ is the origin of Xp in projector coordinates, and $R_p$ and $t_p$ define the transformation between the world coordinate system and the light source's coordinate system, with $R_p$ being a rotation matrix and $t_p$ a translation matrix.

41. The method of claim 33, comprising calculating the world coordinates $p_w$ of a point P according to the following equation:

$$\begin{pmatrix} p_p \\ p_s \end{pmatrix} - \begin{pmatrix} F_c(p_w; \Theta_c) \\ F_p(p_w; \Theta_p) \end{pmatrix} = 0$$

where $p_p=(x_p,y_p)^t$ is the pixel coordinate of said point, $p_x=(x_s)$ is the stripe value of said point P, $F_c(P_w; \Theta_c)=P_p-\in_p$ is the noise-free value of the vector of pixel coordinates, where $P_p$ is the vector of measured pixel coordinates and $\in_p$ is the vector of errors in the pixel coordinates; $F_P(P_w; \Theta_p)=P_s-\in_s$ is the noise-free value of the vector of stripe coordinates, where $P_s$ is the vector of measured stripe coordinates and $\in_s$ is the vector of errors in the stripe coordinates.

42. The method of claim 41, comprising estimating the world coordinates p w of a point P according to the following non-linear least squares (NLLS) equations:

$$\min_{\Theta_c} \|P_p - F_c(P_w; \Theta_c)\|^2$$

$$\min_{\Theta_p} \|P_s - F_p(P_w; \Theta_p)\|^2.$$

43. The method of claim 42, comprising solving said NLLS equations using a NLLS solving algorithm selected from the group consisting of the Gauss-Newton technique, the quasi-Newton technique, and the Levenberg-Marquardt technique.

44. The method of claim 33, comprising calculating the location, in world coordinates, of a kth point on the object according to the following equation:

$$p_w^k = \frac{C_{1,2,1}^k - x_p C_{3,2,1}^k - y_p C_{1,3,1}^k - x_s C_{1,2,2}^k + x_s x_p C_{3,2,2}^k + x_s y_p C_{1,3,2}^k}{C_{1,2,1}^4 - x_p C_{3,2,1}^4 - y_p C_{1,3,1}^4 - x_s C_{1,2,2}^4 + x_s x_p C_{3,2,2}^4 + x_s y_p C_{1,3,2}^4}$$

where $C_{i,j,l}^k = \det(C_c^i, C_c^j, C_c^l, e_k)$ are constants which depend only on a camera perspective transformation matrix and a projector perspective transformation matrix.

45. The method of claim 33, comprising providing a calibration object.

* * * * *